US012559455B2

(12) United States Patent
Kwon et al.

(10) Patent No.: US 12,559,455 B2
(45) Date of Patent: Feb. 24, 2026

(54) COMPOUND AS A UBR BOX DOMAIN LIGAND

(71) Applicant: AUTOTAC INC., Seoul (KR)

(72) Inventors: Yong Tae Kwon, Seoul (KR); Hyun Tae Kim, Seoul (KR); Jeong Eun Na, Gyeonggi-do (KR); Yu Jin Seo, Gyeonggi-do (KR); Chang Hoon Ji, Seoul (KR); Ha Rim Choi, Seoul (KR); Ji Eun Lee, Seoul (KR); Ah Jung Heo, Gyeonggi-do (KR)

(73) Assignee: AUTOTAC INC., Seoul (KR)

( * ) Notice: Subject to any disclaimer, the term of this patent is extended or adjusted under 35 U.S.C. 154(b) by 633 days.

(21) Appl. No.: 17/921,687

(22) PCT Filed: Apr. 27, 2021

(86) PCT No.: PCT/KR2021/005336

§ 371 (c)(1),
(2) Date: Oct. 27, 2022

(87) PCT Pub. No.: WO2021/221445

PCT Pub. Date: Nov. 4, 2021

(65) Prior Publication Data

US 2023/0174470 A1 Jun. 8, 2023

Related U.S. Application Data

(60) Provisional application No. 63/015,945, filed on Apr. 27, 2020.

(51) Int. Cl.

| | |
|---|---|
| ***C07D 207/12*** | (2006.01) |
| ***C07C 235/16*** | (2006.01) |
| ***C07C 237/42*** | (2006.01) |
| ***C07C 243/36*** | (2006.01) |
| ***C07C 243/38*** | (2006.01) |
| ***C07C 311/39*** | (2006.01) |
| ***C07C 311/49*** | (2006.01) |
| ***C07C 317/28*** | (2006.01) |
| ***C07C 317/36*** | (2006.01) |
| ***C07D 209/08*** | (2006.01) |
| ***C07D 209/30*** | (2006.01) |
| ***C07D 209/34*** | (2006.01) |
| ***C07D 209/42*** | (2006.01) |
| ***C07D 209/44*** | (2006.01) |
| ***C07D 211/54*** | (2006.01) |
| ***C07D 231/18*** | (2006.01) |
| ***C07D 231/56*** | (2006.01) |
| ***C07D 277/36*** | (2006.01) |
| ***C07D 295/135*** | (2006.01) |
| ***C07D 307/68*** | (2006.01) |
| ***C07D 471/04*** | (2006.01) |

(52) U.S. Cl.

CPC .......... *C07C 311/49* (2013.01); *C07C 235/16* (2013.01); *C07C 237/42* (2013.01); *C07C 243/36* (2013.01); *C07C 243/38* (2013.01); *C07C 311/39* (2013.01); *C07C 317/28* (2013.01); *C07C 317/36* (2013.01); *C07D 207/12* (2013.01); *C07D 209/08* (2013.01); *C07D 209/30* (2013.01); *C07D 209/34* (2013.01); *C07D 209/42* (2013.01); *C07D 209/44* (2013.01); *C07D 211/54* (2013.01); *C07D 231/18* (2013.01); *C07D 231/56* (2013.01); *C07D 277/36* (2013.01); *C07D 295/135* (2013.01); *C07D 307/68* (2013.01); *C07D 471/04* (2013.01); *C07C 2602/08* (2017.05)

(58) Field of Classification Search

CPC ........................... C07C 207/12; C07D 311/49

See application file for complete search history.

(56) References Cited

U.S. PATENT DOCUMENTS

| | | | |
|---|---|---|---|
| 5,464,738 | A | 11/1995 | Lynch et al. |
| 6,809,119 | B2 | 10/2004 | Hu et al. |
| 2003/0149110 | A1 | 8/2003 | Hu |
| 2016/0185785 | A1 | 6/2016 | Ioannidis et al. |
| 2018/0222857 | A1 | 8/2018 | Voss et al. |

FOREIGN PATENT DOCUMENTS

| | | | |
|---|---|---|---|
| AU | 2015374170 | A1 | 7/2017 |
| AU | 2016277367 | A1 | 12/2017 |
| CN | 1339485 | A | 3/2002 |
| CN | 104797591 | A | 7/2015 |
| CN | 105189484 | A | 12/2015 |
| CN | 107406451 | A | 11/2017 |
| CN | 109748873 | A | 5/2019 |

(Continued)

OTHER PUBLICATIONS

Leaver, et al. J. Med. Chem. 2019, 62, 7146-7159.*

(Continued)

*Primary Examiner* — Shawquia Jackson

(74) *Attorney, Agent, or Firm* — Harness, Dickey & Pierce, P.L.C.

(57) ABSTRACT

The present specification relates to a compound as a UBR box domain ligand. The present specification provides a small molecule compound that binds to the UBR box domain. Further, the present specification provides a composition for inhibiting UBR box domain substrate binding, including a ligand compound that binds to a UBR box domain, a pharmaceutical composition for treating UBR-related disease, and a use thereof.

10 Claims, 19 Drawing Sheets

(56) References Cited

FOREIGN PATENT DOCUMENTS

| | | | |
|---|---|---|---|
| CN | 110431135 | A | 11/2019 |
| CN | 110914271 | A | 3/2020 |
| JP | 2003-206273 | A | 7/2003 |
| JP | 2015-526433 | A | 9/2015 |
| KR | 10-2015-0080706 | A | 7/2015 |
| KR | 10-2018-0038293 | A | 4/2018 |
| TW | 201639847 | A | 11/2016 |
| WO | WO-01-83481 | A1 | 11/2001 |
| WO | WO-2007/056464 | A1 | 5/2007 |
| WO | WO-2015-102419 | A1 | 7/2015 |
| WO | WO-2018/102419 | A1 | 6/2018 |
| WO | WO-2019/084030 | A1 | 5/2019 |
| WO | WO-2019-108824 | A1 | 6/2019 |

OTHER PUBLICATIONS

Goldfarb. US 20090163545 A1 (abstract); Jun. 25, 2009; Accession No. 2009:846108.*

Chaudhary, et al. Current Computer-Aided Drug Design (2016), 12(4), 282-293(abstract); retrieved from STN; Accession No. 2016:1872926.*

Aurelio, et al. BR 200600674 A (abstract); Oct. 30, 2007; Accession No. 2008:1149937).*

Lima, et al. Journal of the Brazilian Chemical Society (1999), 10 (5), 421-428 (abstract); Accession No. 1999:789199.*

Asis, et al. Acta Farmaceutica Bonaerense (1997), 16 (4), 209-214 (abstract); Accession No. 1998:144326.*

International Search Report from corresponding PCT Application No. PCT/KR2021/005336, dated Aug. 17, 2021.

International Search Report from corresponding PCT Application No. PCT/KR2021/005335, dated Aug. 23, 2021.

Chemical Abstract Compound, STNext, RN: 84907-37-9 (Nov. 16, 1984).

Chemical Abstract Compound, STNext, RN: 24088-30-7 (Nov. 16, 1984).

Chemical Abstract Compound, STNext, RN: 316143-03-0 (Jan. 23, 2001).

Chemical Abstract Compound, STNext, RN 1797947-97-7 (Jul. 9, 2015).

Office Action from corresponding Korean Patent Application No. 10-2022-7037602, issued on Aug. 30, 2024.

Ni, C., et al.; "Access to Thiophene and 1H-Pyrrole via Amine-Initiated (3+2) Annulation and Aromatization Cascade Reaction of β'-Acetoxy Allenoate and 1,2-Bisnucleophile", Org. Lett., 2016, vol. 18, pp. 2240-2243.

Office Action from corresponding Taiwanese Patent Application No. 110115113 issued on Nov. 20, 2024.

Written Opinion of the International Searching Authority from corresponding PCT Application No. PCT/KR2021/005336, dated Aug. 17, 2021.

The Second Office Action of CN Patent Application No. 202180045420.X issued on Jul. 12, 2024.

Japanese Office Action of JP Patent Application No. 2022-563435 issued on May 28, 2024.

Osman, S. A. A., et al., "Synthesis of Sulfanilamido-Naphtoquinones as Potential Antituberculous Agents", Journal of Pharmaceutical Sciences, 1983, 72(1), pp. 68-71.

Guha, P. C., et al., Current Science, Letters to the Editor, 1943, 12, 150.

Ariesan, V., et al,; Farmacia (Bucharest, Romania), 1971, 19(4), pp. 213-218.

Osman et al, XP 971918 A "Synthesis of Sulfanilamido-Naphtoquinones as Potential Antituberculous Agents", Journal of Pharmaceutical Sciences, 1983, 72(1), pp. 68-71.

European Search Report of EP Patentt Application No. 21796989.8 issued on Apr. 24, 2024.

Office Action of CN Patent Application No. 202180044509.4 issued on Nov. 27, 2023.

Mol. Cell. Biochem, 414/ Dec. 31, 2016 / Swamy Jagadish et al, Platelet protective efficacy of 3,4,5 trisubstituted isoxazole analogue by inhibiting ROS-mediated apoptosis and platelet aggregation.

J. Med. Chem, 63, Mar. 2, 2020 / Daniel L. Priebbenow et al, Discovery of Acylsulfonohydrazide-Derived Inhibitors of the Lysine Acetyltransferase, KAT6A, as Potent Senescence-Inducing Anti-Cancer Agents.

STN Registry Aug. 15, 2005 / CAS, 860238-09-1.

Office Action of CN Patent Application No. 202180045420.X issued on Sep. 29, 2023.

Written Opinion from corresponding PCT-KR2021-005335,, dated Aug. 18, 2021.

* cited by examiner

Compound 1

Compound 5

Compound 9

Compound 11

Compound 12

Compound 13

COMPOUND AS A UBR BOX DOMAIN LIGAND

CROSS-REFERENCE TO RELATED APPLICATION

This application is a national phase entry of PCT Application No. PCT/KR2021/005336, filed on Apr. 27, 2021, which claims the benefit and priority of U.S. Provisional Application Ser. No. 63/015,945 filed on Apr. 27, 2020, the disclosures of which are incorporated herein by reference in its entirety.

FIELD

The content disclosed in the present specification relates to a compound as a UBR box domain ligand. The UBR box domain is a domain commonly present in a ubiquitin protein ligase E3 component n-recognin (UBR) protein of the N-end rule pathway. In this case, the UBR box domain is known as a domain to which a substrate binds. The UBR box domain is essential for binding to the N-terminal residue of a substrate to form a multiubiquitin chain in the substrate, and the substrate is known to be degraded through this process.

The present specification relates to a compound that serves as a ligand that binds to the UBR box domain.

BACKGROUND

Cells regulate the amount and function of in vivo proteins by degrading proteins. In this case, in vivo proteins may be degraded depending on the N-terminal residue sequence, and such a degradation pathway is known as an N-end rule pathway.

That is, the N-end rule pathway is a proteolytic system that uses a specific protein N-end as a degradation signal. The N-end rule pathway may include the following proteolytic process.

In the case of eukaryotes, an N-recognin recognizes the N-terminal degradation signal of a protein, and the N-recognin may degrade the protein by allowing ubiquitin to bind to a protein to be degraded. In this case, the N-terminal degradation signal may include those having a residue having a positive charge (type 1: for example, arginine, lysine, and histidine) or a large hydrophobic residue (type 2: phenylalanine, leucine, tryptophan, isoleucine, and tyrosine) at the N-terminal. The present inventors discovered or cloned N-recognins UBR 1, UBR2, UBR3, and UBR5 for the first time, and revealed that the N-recognins have a UBR box domain as a substrate recognition domain (Tasaki et al. 2005). In this case, a ubiquitinated substrate produced by the binding of an N-recognin to an N-end rule ligand is delivered to a proteasome and is degraded into short peptides. In this process, a specific N-terminal residue (Nt-Arg, Nt-His, Nt-Lys, Nt-Trp, Nt-Phe, Nt-Tyr, Nt-Leu, Nt-Leu) provides most of the hydrogen bonds required when an N-recognin targets an N-end rule substrate, and thus is a determinant essential for binding (Sriram and Kwon, 2010).

The UBR is an abbreviation for Ubiquitin protein ligase E3 component n-recognin, and UBR is an N-recognin that recognizes the N-terminal degradation signal of a protein. It is known that at least 7 types of UBRs 1 to 7 are present in mammals. Further, a UBR box domain that UBRs have in common is a zinc finger motif having a size of about 70 residues, and is known as a highly conserved substrate-binding domain. [Kwon et al., 1998; Xie and Varshaysky, 1999; Kwak et al., 2004; Varshaysky, 1996; Varshaysky, 1997; Kwon et al., 2011; and Zenker et al., 2014].

That is, UBR is an N-recognin associated with the N-end rule pathway, which is a proteolytic pathway, and the UBR box domain in UBR is a substrate binding domain. In particular, among the UBRs 1 to 7, UBR1, UBR2, UBR3 and UBR5 are known to act as ubiquitin protein ligase E3 and have a RING domain or a HECT domain. An N-end rule substrate that binds to the UBR is degraded by a ubiquitin proteasome pathway. Specifically, the UBR box domain in the UBR recognizes the N-terminal amino acid of a substrate and ubiquitinates the substrate via the RING domain or the HECT domain, thereby degrading the substrate via the proteasome pathway. For example, when misfolded proteins remain in a cell for an extended period of time, the proteins may be aggregated to block proteasomes or reduce other cell functions, and thus are degraded via the ubiquitin proteasome pathway (Ji and Kwon, 2017).

That is, the UBR box domain plays an important role in an intracellular proteolytic pathway by recognizing an N-terminal degradation signal. Therefore, ligands that bind to the UBR box domain may affect intracellular proteolytic pathways.

As described above, the present specification relates to a compound as a ligand that binds to a UBR box domain associated with an intracellular proteolytic pathway.

DETAILED DESCRIPTION

Technical Problem

The present specification provides a small molecule compound that binds to a UBR box domain. In this case, the UBR box domain includes a UBR box domain in UBR 1 to 7. The small molecule compound may function as a ligand suitable for binding to UBR box domain.

In one embodiment, the present specification provides a composition for inhibition of UBR box domain substrate binding comprising a ligand compound that binds to a UBR box domain.

In one specific embodiment, the present specification provides a pharmaceutical composition for treating UBR-related disease, and a use thereof, and the composition comprises a ligand compound that binds to a UBR box domain.

In a more specific embodiment, the present specification provides a pharmaceutical composition for treating disease including a muscle loss caused by muscular dystrophy (Becker, Congennital, Duchenne, Distal, Emery-Dreifuss, Facioscapulohumeral, Limb-girdle, myotonic, ocuophargyngeal), muscle wasting diseases mediated by muscle loss or degradation including sarcopenia or cancer cachexia, diseases caused by excessive protein degradation including liposarcoma, cystic fibrosis, Johanson-Blizzard syndrome, obstructive urinary tract disease(urethral obstruction sequence), autoimmune pancreatitis or known diseases related to UBR box and UBR protein including Usher syndrome, and a use thereof, and the composition comprises a ligand compound that binds to a UBR box domain.

Technical Solution

The present specification provides a compound having the structure of formula 1 or a salt thereof.

[formula 1]

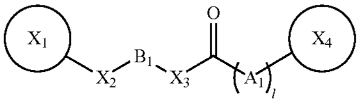

l = 0 or 1 wherein the $X_1$ is an optionally substituted with one or more $R_2$ or unsubstituted phenyl, cycloalkyl or heterocyclyl;

each $R_2$ is independently selected from alkyl, alkoxy, amino, aminoalkyl, —$NO_2$, =O, —$NHC_2H_4OH$, —C(=NH)$NH_2$, —C(=O)$NH_2$, —C(=O)$NHCH_3$, —C(=O)OH, phenyl or heterocycloalkyl;

$X_4$ is an optionally substituted with one or more $R_3$ or unsubstituted phenyl, cycloalkyl or heterocylyl;

each $R_3$ is independently selected from alkyl, alkoxy, amino, halo, hydroxyl, alkylamino, dialkylamino, —$NO_2$, —CONR'R", —$CO_2$R', —NHCOR', phenyl or heterocycloalkyl;

each R' and R" is independently —H or alkyl;

$X_2$ is $SO_2$ or $CR_aR_b$;

$R_a$ and $R_b$ are each independently H or $CH_3$;

$X_3$ is NH or $CH_2$;

$B_1$ is $CH_2$ or NH;

$A_1$ is $CH_2$ or NH.

In this case, as an example, in formula 1,

—X2-B1-X3 is selected from a group consisting of —$SO_2$—NH—NH, —$SO_2$—NH—$CH_2$, —$SO_2$—$CH_2$—NH and —$CH_2$—NH—NH, the $X_1$ is an optionally substituted with one or more $R_2$ or unsubstituted phenyl, cycloalkyl or heterocyclyl;

each $R_2$ is independently selected from alkyl, alkoxy, amino, aminoalkyl, —$NO_2$, =O, —$NHC_2H_4OH$, —C(=NH)$NH_2$, —C(=O)$NH_2$, —C(=O)$NHCH_3$, —C(=O)OH, phenyl or heterocycloalkyl;

the $X_4$ is an optionally substituted with one or more $R_3$ or unsubstituted phenyl, cycloalkyl or heterocylyl;

each $R_3$ is independently selected from alkyl, alkoxy, amino, halo, hydroxyl, alkylamino, dialkylamino, —$NO_2$, —CONR'R", —$CO_2$R', —NHCOR', phenyl or heterocycloalkyl; wherein each R' and R" is independently —H or alkyl;

$A_1$ is $CH_2$ or NH,

I is an integer of 0 or 1.

As a specific example, the each $X_1$ and $X_4$ is independently substituted or unsubstituted phenyl, cycloalkyl or heterocyclyl; wherein each $X_1$ and $X_4$ may be selected from independently substituted or unsubstituted phenyl, cyclohexyl, cyclopentyl, furanyl, thiazolyl, 1H-pyrazolyl, pyrrolidinyl, piperidinyl, piperazinyl, morpholinyl, indolinyl, 1H-indolinyl, 1H-indazolyl, isoindolinyl, indolin-2-only, 2,3-dihydro-1H-indenyl and 1H-pyrrolopyridinyl.

In this case, as an example, the each $R_2$ may be independently selected from methyl, ethyl, amino, aminoalkyl, amino(hydroxyalkyl), methoxy, ethoxy, —C(=NH)$NH_2$, —C(=O)$NH_2$, —C(=O)$NHCH_3$, —C(=O)OH, phenyl, pyrrolidinyl, piperazinyl, piperidinyl and morpholinyl.

In this case, as an example, the each $R_3$ is independently selected from hydroxyl, fluoro, chloro, bromo, amino, methyl, ethyl, isopropyl, methoxy, ethoxy, isopropyloxy, alkylamino, dialkylamino, —$NO_2$, —C(=O)$NH_2$, —$CO_2$R', —NHCOR', —CONR'R" and phenyl;

each R' and R" is independently —H or alkyl.

As an example, the present specification provides a compound a salf thereof wherein the formula 1 is formula 1-1:

[formula 1-1]

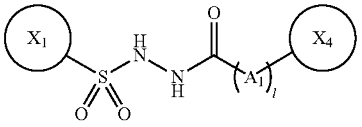

wherein, A1 is CH2 or NH,

I is an integer of 0 or 1.

In this case, as an example, the present specification provides a compound a salf thereof wherein the formula 1 is formula 1-2:

[formula 1-2]

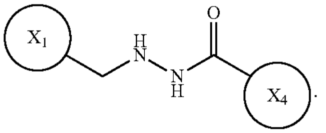

In this case, as an example, the present specification provides a compound a salf thereof wherein the formula 1 is formula 1-3:

[formula 1-3]

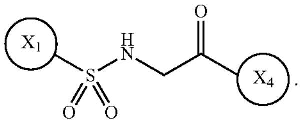

In this case, as an example, the present specification provides a compound or a salf thereof wherein the formula 1 is formula 1-4:

[formula 1-4]

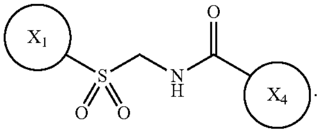

In this case, in formula 1-1, 1-2, 1-3 and 1-4, as an example, wherein the X1 is an optionally substituted with one or more R2 or unsubstituted phenyl, cycloalkyl or heterocyclyl, wherein the each R2 is independently selected from alkyl, alkoxy, amino, aminoalkyl, —NO2, =O, —NHC2H4OH, —C(=NH)NH2, —C(=O)NH2, —C(=O)NHCH3, —C(=O)OH, phenyl or heterocycloalkyl;

X4 is an optionally substituted with one or more R3 or unsubstituted phenyl, cycloalkyl or heterocylyl; wherein the each R3 is independently selected from alkyl, alkoxy, amino, halo, hydroxyl, alkylamino, dialkylamino, —NO2, —CONR'R", —CO2R', —NHCOR', phenyl or heterocycloalkyl; each R' and R" is independently —H or alkyl.

As a specific example, the each X1 and X4 is independently substituted or unsubstituted phenyl, cycloalkyl or heterocyclyl; wherein each X1 and X4 may be selected from independently substituted or unsubstituted phenyl, cyclohexyl, cyclopentyl, furanyl, thiazolyl, 1H-pyrazolyl, pyrrolidinyl, piperidinyl, piperazinyl, morpholinyl, indolinyl, 1H-indolinyl, 1H-indazolyl, isoindolinyl, indolin-2-only, 2,3-dihydro-1H-indenyl and 1H-pyrrolopyridinyl.

In this case, as an example, the each $R_2$ may be independently selected from methyl, ethyl, amino, aminoalkyl, amino(hydroxyalkyl), methoxy, ethoxy, $-C(=NH)NH_2$, $-C(=O)NH_2$, $-C(=O)NHCH_3$, $-C(=O)OH$, phenyl, pyrrolidinyl, piperazinyl, piperidinyl and morpholinyl.

In this case, as a specific example, the present specification provides a compound or a salf thereof wherein the $R_2$ is amino.

In this case, as an example, the present specification provides a compound or a salf thereof wherein the $X_1$ is

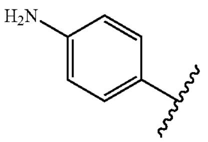

or

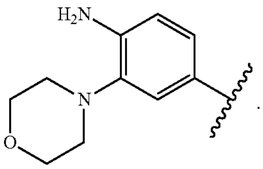

.

In this case, as an example, the each $R_3$ is independently selected from hydroxyl, fluoro, chloro, bromo, amino, methyl, ethyl, isopropyl, methoxy, ethoxy, isopropyloxy, alkylamino, dialkylamino, $-NO_2$, $-C(=O)NH_2$, $-CO_2R'$, $-NHCOR'$, $-CONR'R''$ and phenyl;

each R' and R'' is independently —H or alkyl.

In this case, as an example, the present specification provides a compound or a salf thereof wherein the $X_4$ is

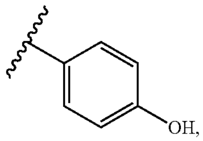

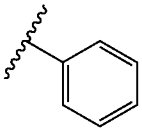

or

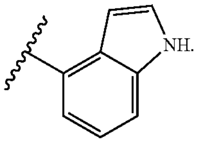

In this case, as an example, the compound may be selected from

N'-(4-hydroxybenzoyl)-4-methylbenzenesulfonohydrazide;

4-amino-N'-(4-hydroxybenzoyl)benzenesulfonohydrazide;

4-amino-N'-(4-hydroxybenzoyl)-3-morpholinobenzenesulfonohydrazide;

N'-(4-hydroxybenzoyl)-2-oxoindoline-5-sulfonohydrazide;

N'-(4-hydroxybenzoyl)indoline-5-sulfonohydrazide;

N'—([1,1'-biphenyl]-4-carbonyl)-4-aminobenzenesulfonohydrazide;

N'—([1,1'-biphenyl]-3-carbonyl)-4-aminobenzenesulfonohydrazide;

3-amino-N'-(4-hydroxybenzoyl)benzenesulfonohydrazide;

4-(1-aminoethyl)-N'-(4-hydroxybenzoyl)benzenesulfonohydrazide;

3,5-diamino-N'-(4-hydroxybenzoyl)benzenesulfonohydrazide;

N'-(4-hydroxybenzoyl)-4-((2-hydroxyethyl)amino)benzenesulfonohydrazide;

N'-(4-hydroxybenzoyl)-4-methoxybenzenesulfonohydrazide;

4-((2-(4-hydroxybenzoyl)hydrazinyl)sulfonyl)benzimidamide;

4-((2-(4-hydroxybenzoyl)hydrazinyl)sulfonyl)benzamide;

6-amino-N'-(4-hydroxybenzoyl)-[1,1'-biphenyl]-3-sulfonohydrazide;

4-(2-((4-aminophenyl)sulfonyl)hydrazine-1-carbonyl)benzamide;

4-amino-N'-(1H-indole-3-carbonyl)benzenesulfonohydrazide;

4-amino-N'-(4-hydroxybenzoyl)-3-(pyrrolidin-1-yl)benzenesulfonohydrazide;

N'-(4-hydroxybenzoyl)-4-nitro-3-(pyrrolidin-1-yl)benzenesulfonohydrazide;

4-amino-N'-(4-hydroxybenzoyl)-3-(piperidin-1-yl)benzenesulfonohydrazide;

N'-(4-hydroxybenzoyl)-1H-pyrazole-4-sulfonohydrazide;

N'-(4-hydroxybenzoyl)indoline-4-sulfonohydrazide;

N'-(4-hydroxybenzoyl)-1H-indole-4-sulfonohydrazide;

2-((4-aminophenyl)sulfonyl)-N-phenylhydrazine-1-carboxamide;

4-amino-N'-(1H-indole-4-carbonyl)-3-morpholinobenzenesulfonohydrazide;

4-amino-N'-(indoline-4-carbonyl)benzenesulfonohydrazide;

4-amino-N'-(4-hydroxybenzoyl)-3-(piperazin-1-yl)benzenesulfonohydrazide;

4-amino-N'-(2,3-dihydro-1H-indene-2-carbonyl)benzenesulfonohydrazide;

4-amino-N'-(isoindoline-2-carbonyl)benzenesulfonohydrazide;

N'-(4-hydroxybenzoyl)-1H-indole-2-sulfonohydrazide;

4-amino-N'-(2-phenylacetyl)benzenesulfonohydrazide;

N'-(4-hydroxybenzoyl)-1H-indazole-3-sulfonohydrazide;

4-amino-N'-(indoline-6-carbonyl)benzenesulfonohydrazide;

4-amino-N'-(indoline-3-carbonyl)benzenesulfonohydrazide;

N'-(4-hydroxybenzoyl)piperidine-4-sulfonohydrazide;

4-amino-N'-(indoline-6-carbonyl)-3-morpholinobenzenesulfonohydrazide;

4-amino-N'-(piperazine-1-carbonyl)benzenesulfonohydrazide;

4-amino-3-morpholino-N'-(piperazine-1-carbonyl)benzenesulfonohydrazide;

N'-(4-hydroxybenzoyl)-2-methylthiazole-4-sulfonohydrazide;

(1S,4S)-4-amino-N'-(4-hydroxybenzoyl)cyclohexane-1-sulfonohydrazide;

(1R,4R)-4-amino-N'-(4-hydroxybenzoyl)cyclohexane-1-sulfonohydrazide;

4-((2-(4-hydroxybenzoyl)hydrazinyl)sulfonyl)-5-methylfuran-2-carboxylic acid;

N'-(4-hydroxybenzoyl)pyrrolidine-3-sulfonohydrazide;

N'-(4-hydroxybenzoyl)-1H-pyrrolo[2,3-b]pyridine-2-sulfonohydrazide;

2-((4-aminophenyl)sulfonyl)-N'-(3-hydroxyphenyl)hydrazine-1-carboxamide;

2-((4-amino-3-morpholinophenyl)sulfonyl)-N-phenylhydrazine-1-carboxamide;

N'-(4-aminobenzyl)-4-hydroxybenzohydrazide;

4-hydroxy-N'-(4-methoxybenzyl)benzohydrazide;

N'-(4-aminobenzyl)-2,3-dihydro-1H-indene-2-carbohydrazide;

4-amino-N'-(2-(4-hydroxyphenyl)-2-oxoethyl)benzenesulfonamide;

4-amino-N'-(2-(4-hydroxyphenyl)-2-oxoethyl)-3-morpholinobenzenesulfonamide;

3,5-diamino-N'-(2-(4-hydroxyphenyl)-2-oxoethyl)benzenesulfonamide;

N-(((4-aminophenyl)sulfonyl)methyl)-4-hydroxybenzamide;

4-hydroxy-N-(((4-methoxyphenyl)sulfonyl)methyl)benzamide;

N-(((4-aminophenyl)sulfonyl)methyl)-[1,1'-biphenyl]-4-carboxamide.

In another aspect, the present specification provides a pharmaceutical composition for treating UBR related disease comprising the compound or pharmaceutically acceptable salt thereof, and a method for treating UBR related disease by using the compound.

In this case, as an example, the UBR related disease may be selected from muscle loss caused by muscular dystrophy (Becker, Congennital, Duchenne, Distal, Emery-Dreifuss, Facioscapulohumeral, Limb-girdle, myotonic, ocuopharyngeal), muscle wasting diseases mediated by muscle loss or degradation including sarcopenia or cancer cachexia, diseases caused by excessive protein degradation including liposarcoma, cystic fibrosis, Johanson-Blizzard syndrome, obstructive urinary tract disease(urethral obstruction sequence), autoimmune pancreatitis or Usher syndrome.

Advantageous Effects

An invention disclosed herein provides a ligand compound having a high binding strength with respect to a UBR box domain.

Through a UBR box domain ligand compound, UBR box domain substrate binding can be suppressed, and a variety of applications that take advantage of this characteristic can be provided. For example, a UBR-related disease (for example, sarcopenia, and the like) can be treated by a UBR box domain ligand compound.

DETAILED DESCRIPTION

Figure 1:
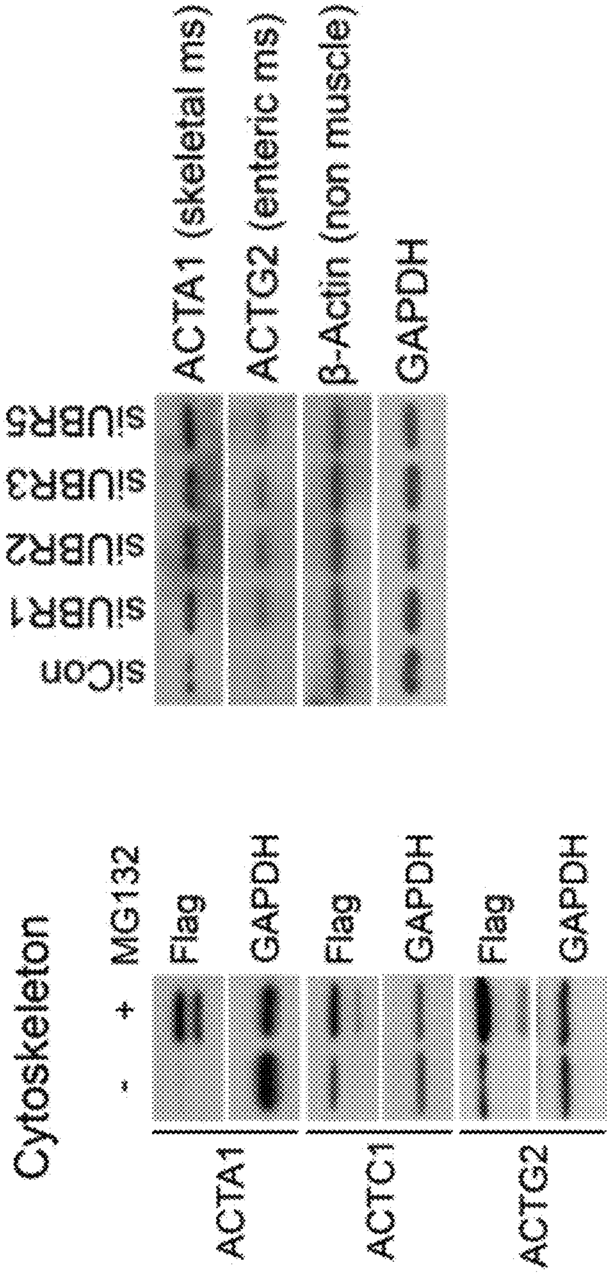
FIG. 1 illustrates the experimental results of confirming whether muscle actin is an Arg/N-degron pathway substrate using an immunoblotting method.

Hereinafter, the content of the invention will be described in more detail through specific exemplary embodiments and examples with reference to the accompanying drawings. It should be noted that the accompanying drawings include some exemplary embodiments of the invention, but not all exemplary embodiments. The content of the invention disclosed by the present specification can be implemented variously, and is not limited to specific exemplary embodiments described herein. A person with ordinary skill in the art to which the invention disclosed herein pertains will be able to conceive of many modifications and other exemplary embodiments of the content of the invention disclosed herein. Therefore, it should be understood that the content of the invention disclosed herein is not limited to the specific exemplary embodiments described herein, and modifications thereof and other exemplary embodiments are also within the scope of the claims.

DEFINITION OF TERMS

The definitions of the main terms used herein are given below.

Ubiquitin Protein Ligase E3 Component n-Recognin (UBR)

The term UBR as used herein refers to an abbreviation for Ubiquitin protein ligase E3 component n-recognin. The UBR is an N-recognin that recognizes an N-terminal residue of a protein, and it is known that at least 7 types of UBRs 1 to 7 are present in mammals. The UBR is an N-recognin and is associated with the N-end rule pathway, which is an in vivo proteolytic pathway. Specifically, the UBR recognizes an N-terminal degradation signal (N-degron) of a protein, and is involved in a process by which a substrate protein is degraded via a ubiquitin proteasome pathway.

UBR Box Domain

The term UBR box domain used herein is a domain that is present in the UBR protein, and is a zinc finger motif. The UBR protein includes UBR 1 to 7 proteins. The UBR box domain is known as a domain to which a substrate protein binds. The compound as the UBR box domain ligand disclosed herein may suppress UBR box domain substrate binding by binding to the UBR box domain. Furthermore, the compound as the UBR box domain ligand disclosed herein may affect the intracellular proteolytic pathway.

RING Domain

The term RING domain used herein is known to be present in UBR 1, 2 and 3 proteins. The RING domain may also be interchanged with RING ubiquitination domain. The RING domain is a domain present in a protein and is a zinc finger motif. The RING domain is a domain that plays an important role in a process in which a ubiquitin present in E2 is transferred to a substrate protein, and the RING domain serves to allow a process in which the ubiquitin is transferred to a substrate protein to occur in one step.

HECT Domain

The term HECT domain used herein is known to be present in a UBR 5 protein. The HECT domain may also be interchanged with HECT ubiquitination domain. The HECT domain is a domain that plays an important role in a process in which the ubiquitin present in E2 is transferred to a substrate protein. The ubiquitin present in E2 is delivered to the HECT domain and then transferred to the substrate protein. That is, the HECT domain serves to allow a process in which the ubiquitin is transferred to a substrate protein to occur in two steps.

Zinc Finger Motif

As used herein, the term zinc finger motif refers to a protein structural motif in which one or more zinc ions are present to stabilize the structure of a protein. The UBR box domain and RING domain of the present specification are zinc finger motifs.

Ligand

As used herein, the term ligand refers to a material that specifically binds to a protein. The protein includes an enzyme or a receptor, and when the protein is an enzyme, the ligand may refer to a substrate or the like that binds to the enzyme, and when the protein is a receptor, the ligand may refer to a hormone or the like that binds to the receptor.

The compound as the UBR box domain ligand provided herein means a compound that binds to the UBR box domain. As an example, the compound refers to a compound that binds to the UBR box domain in the UBR protein. As a specific example, the compound refers to a compound that binds to the UBR box domain present in one or more proteins of UBRs 1 to 7. However, the compound is not limited thereto.

The compound as a UBR box domain ligand provided herein may act competitively with a substrate of the UBR box domain. That is, the compound may suppress the substrate binding of the UBR box domain. In addition, the compound may inhibit the degradation of the substrate by suppressing the binding of the substrate.

Aminoalkyl

As used herein, the term aminoalkyl refers to an alkyl moiety substituted with an amino group. The aminoalkyl group includes $-CH(NH_2)CH_3$ and $-CH_2(NH_2)$.

Cycloalkyl and Heterocycloalkyl

As used herein, the term cycloalkyl refers to a carbocyclic group containing one or more saturated ring structures, and includes a bicyclic group. Examples of the cycloalkyl include cyclopropyl, cyclobutyl, cyclopentyl, cyclohexyl, cycloheptyl, and cyclooctyl.

A heterocycloalkyl refers to a ring structure including one or more heteroatoms selected from P, N, O, and S in addition to a ring-carbon atom in the cycloalkyl.

Heterocyclyl

As used herein, the term heterocyclyl refers to an unsaturated, saturated or partially unsaturated monocyclic, bicyclic, or tricyclic group having 12 to 14 ring carbon atoms, and includes one or more heteroatoms selected from P, N, O, and S in addition to ring-carbon atoms. The heterocyclyl includes a heterocycloalkyl. In various exemplary embodiments, the heterocyclic group is attached to another moiety through a carbon or heteroatom, and is optionally substituted on the carbon or heteroatom. Examples of the heterocyclyl include azetidinyl, benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, isoindolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isooxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrahydrothiopyranyl, tetrahydroisoquinolinyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyridin-2-only, pyrrolidinyl, pyrrolopyridinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, tetrahydrothienyl, and the like.

Unless otherwise defined, all technical and scientific terms used herein have the same meaning as commonly understood by one with ordinary skill in the art to which the present invention pertains. All publications, patents, and other references mentioned herein are incorporated by reference in their entity.

Hereinafter, the specific contents of the invention will be disclosed.

I. UBR BOX DOMAIN

1. Overview

The compound as the UBR box domain ligand provided herein binds to a UBR box domain. The UBR box domain is known as a domain to which an N-terminal residue sequence or an N-terminal degradation signal binds. The domain is associated with a process by which proteins are degraded by the N-end rule pathway. Therefore, the compound may affect a proteolytic process via the N-end rule pathway.

2. N-End Rule Pathway

Cells regulate the amount of protein through proteolysis. In this case, it is known that the process of protein degradation is performed by a process of recognizing a degron, which is a degradation signal of a protein. Specifically, proteolysis is regulated depending on the N-terminal residue sequence of a protein, and the proteolysis signals present at the N-terminal are collectively called N-degrons. The N-degrons includes those having a residue having a positive charge (for example, arginine, lysine, and histidine) or a large hydrophobic residue (phenylalanine, leucine, tryptophan, isoleucine, and tyrosine) at the N-terminal. As described above, the term N-end rule has been used based on the association that the half-life of a protein is determined by the amino acid residue present at the N-terminal of the protein.

3. UBR Box Domain

In the N-end rule pathway, the N-degron is recognized by an N-recognin and ubiquitin protein ligase E3 component n-recognin (UBR) was discovered as the N-recognin. The UBR is known to recognize the N-terminal residue sequence or the N-terminal degradation signal by the UBR box domain. That is, UBR recognizes a protein degradation signal through the UBR box domain, and the degradation process of the protein is performed through the recognition of the protein degradation signal.

The protein degradation process by UBR may include the following contents. The UBR box domain recognizes a substrate having an N-terminal degradation signal, a ubiquitin is bound to the substrate, and the ubiquitin-bound substrate may be degraded by proteasomes. That is, a substrate having an N-terminal degradation signal may be degraded by a ubiquitin proteasome system (UPS).

II. UBR BOX DOMAIN LIGAND

1. Overview

1) The compound of the present specification reflects the structure of the UBR box domain and characteristics of binding to N-terminal pathway substrate The compound as the UBR box domain ligand disclosed herein was designed in consideration of a structure of the UBR box domain and a binding form of the UBR box domain and the N-terminal pathway substrate.

Various amino acids present in the UBR box domain interact with and bind to amino acids in the N-terminal pathway substrate through ionic interactions, hydrogen bonding, hydrophobic interactions, and the like. By analyzing these binding modes, a small molecule compound capable of forming a suitable binding mode with the UBR box domain is synthesized and provided herein. Furthermore, compounds according to formula 1 to 55 are provided below.

2) The compound of the present specification has a core structure that enhances binding to the UBR box domain.

In the present specification, a binding mode of the UBR box domain and the amino acid of the N-terminal pathway substrate was analyzed as described above, and a core structure of the compound was derived. The compound provided herein may have a structure of the following [formula 1] derived on the basis of the core structure of the compound. [formula 1] is as follows:

[formula 1]

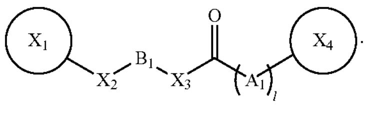

l = 0 or 1

In the present specification, various compounds are designed and provided based on the [formula 1]. In this case, candidates for X1, X2, X3, B1, A1, X4 were derived in consideration of the binding mode with the UBR box domain. A more detailed description on the various compounds based on the [formula 1] is given below.

2 formula 1

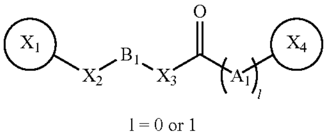

l = 0 or 1

[formula 1]

1) X2, B1, X3, and A1

① X2

In formula 1, X2 may be a structure that induces a kink structure in the compound disclosed herein. The kink structure helps to smoothly maintain charge-charge interactions or hydrogen bonding or hydrophobic interactions of the compound X1 disclosed herein with the UBR box domain, and enhance binding strength. Accordingly, as an example, X2 may be one of the various structures that may induce the kink structure. As a specific example, X2 may be $SO_2$ or CRaRb. In this case, Ra and Rb may each be independently selected from H or $CH_2$. Furthermore, X2 may be $CH_2$, $CH(CH_3)$ or $C(CH_3)_2$. As another specific example, X2 may be $SO_2$.

② B1, X3, and A1

In formula 1, A1 may be CH2 or NH as an example.

In formula 1, B1 may be CH2 or NH as an example.

In formula 1, X3 may be CH2 or NH as an example.

In this case, as an example, when B1 in formula 1 is CH2, X3 may not be CH2.

However, the compound is not limited thereto.

③ Examples of X2, B1, X3, and A1

The formula 1 may have a structure selected from those described below:

[formula 1-1]

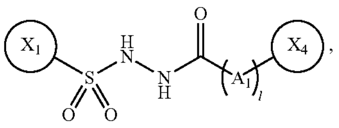

[formula 1-2]

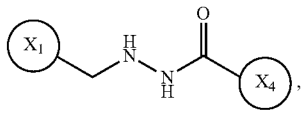

[formula 1-3]

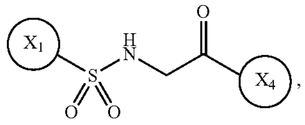

[formula 1-4]

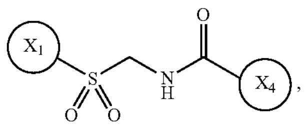

-continued
[formula 1-5]
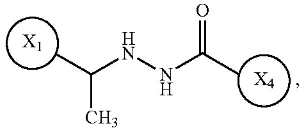
[formula 1-6]
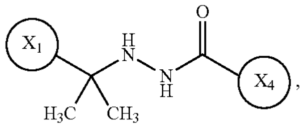
[formula 1-7]
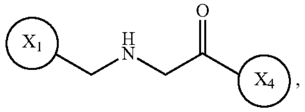
[formula 1-8]
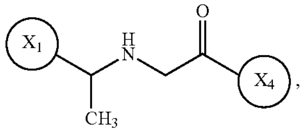
[formula 1-9]
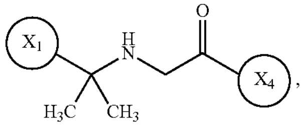
[formula 1-10]
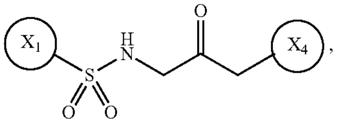
[formula 1-11]
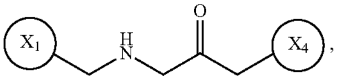
[formula 1-12]
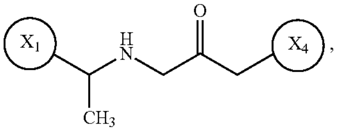
[formula 1-13]
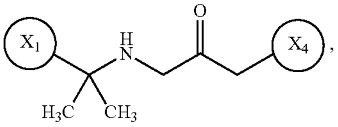
[formula 1-14]
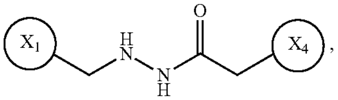
[formula 1-15]
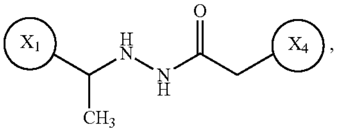
[formula 1-16]
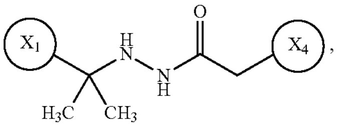
-continued
[formula 1-17
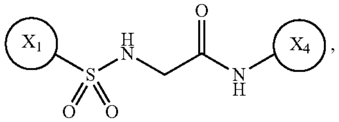
[formula 1-18]
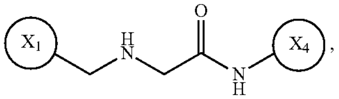
[formula 1-19]
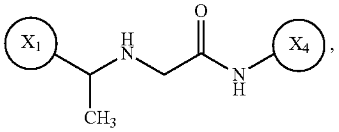
[formula 1-20]
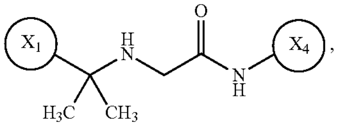
[formula 1-21]
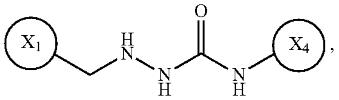
[formula 1-22]
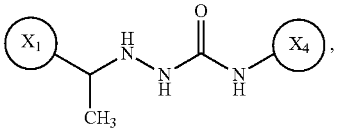
[formula 1-23]
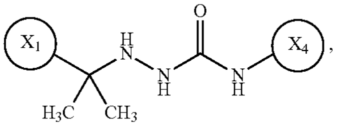
[formula 1-24]
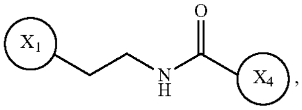
[formula 1-25]
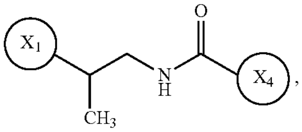
[formula 1-26]
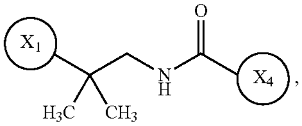
[formula 1-27]
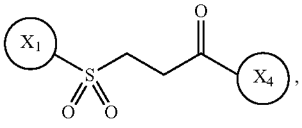
[formula 1-28]
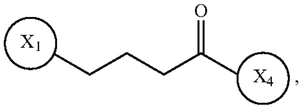

-continued

[formula 1-29]

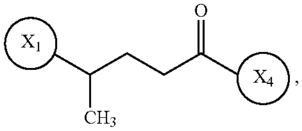

[formula 1-30]

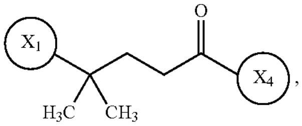

[formula 1-31]

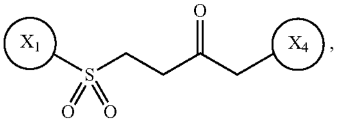

[formula 1-32]

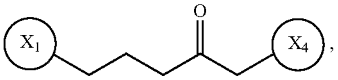

[formula 1-33]

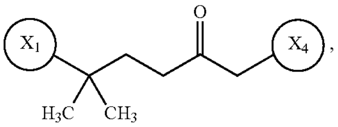

[formula 1-34]

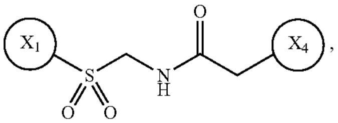

[formula 1-35]

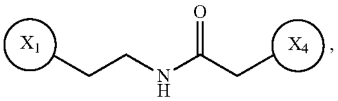

[formula 1-36]

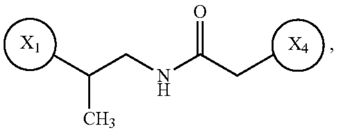

[formula 1-37]

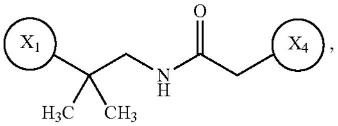

[formula 1-38]

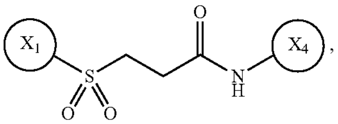

[formula 1-39]

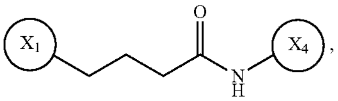

[formula 1-40]

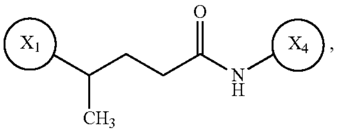

-continued

[formula 1-41]

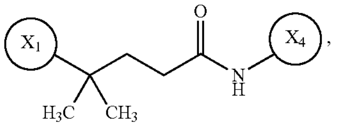

[formula 1-42]

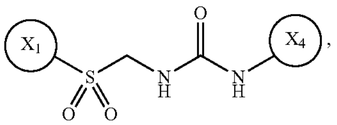

[formula 1-43]

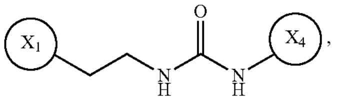

[formula 1-44]

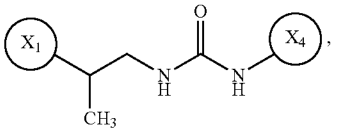

[formula 1-45]

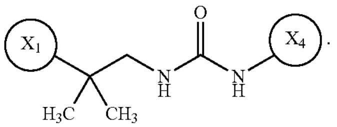

As a specific example, in formula 1, $—X_2—B_1—X_3$ is selected from a group consisting of $—SO_2—NH—NH$, $—SO_2—NH—CH_2$, $—SO_2—CH_2—NH$ and $—CH_2—NH—NH$, $A_1$ is $CH_2$ or NH, and I is an integer of 0 or 1.

The formula 1 may have a structure selected from those described below as a specific example:

[formula 1-1]

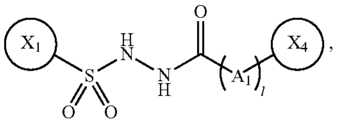

[formula 1-2]

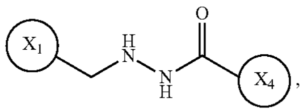

[formula 1-3]

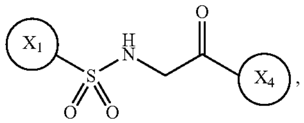

[formula 1-4]

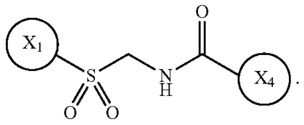

2) X1

As a result of performing a structural analysis of a complex of a UBR box of UBR1 and UBR2 and an N-degron and a molecular docking study of compounds having a core structure of formula 1, in formula 1 $X_1$ corresponds to a side chain of a first residue (N1) of an N-degron, and $X_1$ is expected to bind to a negative charged-surrounded region. Accordingly, as an example, in formula 1, $X_1$ may have a ring structure having an electric charge or including a moiety that forms a hydrogen bond. As a specific example, $X_1$ may be a ring structure having an electric charge or having a planar structure including a moiety that forms a hydrogen bond. Additionally, when the compound is used in combination with another material, $X_1$ in formula 1 may include a structure capable of binding to a linker.

As an example, the $X_1$ may be an optionally substituted with one or more $R_2$ or unsubstituted phenyl, cycloalkyl or heterocyclyl, as a specific example, the $X_1$ may be selected from an optionally substituted with one or more $R_2$ or unsubstituted phenyl, cyclohexyl, cyclopentyl, furanyl, thiazolyl, 1H-pyrazolyl, pyrrolidinyl, piperidinyl, piperazinyl, morpholinyl, indolinyl, 1H-indolinyl, 1H-indolyl, 1H-indazolyl, isoindolinyl, indolin-2-only, 2,3-dihydro-1H-indenyl and 1H-pyrrolopyridinyl. In this case, each $R_2$ may be independently selected from alkyl, alkoxy, amino, aminoalkyl, $—NO_2$, $=O$, $—NHC_2H_4OH$, $—C(=NH)NH_2$, $—C(=O)NH_2$, $—C(=O)NHCH_3$, $—C(=O)OH$, phenyl or heterocycloalkyl. As an example, each $R_2$ may be independently selected from methyl, ethyl, amino, aminoalkyl, amino(hydroxyalkyl), methoxy, ethoxy, $—C(=NH)NH_2$, $—C(=O)NH_2$, $—C(=O)NHCH_3$, $—C(=O)OH$, phenyl, pyrrolidinyl, piperazinyl, piperidinyl and morpholinyl. As a specific example, $R_2$ may be an amino.

As a more specific example, the $X_1$ may be selected from the following structures:

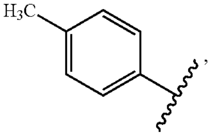,
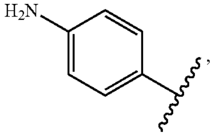,
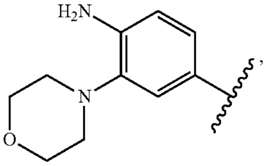,
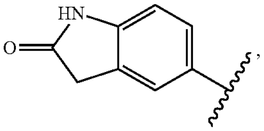,
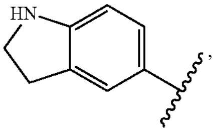,
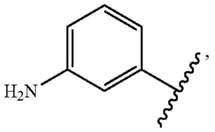,
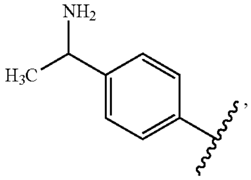,
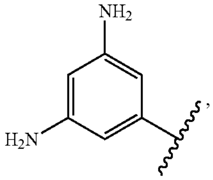,
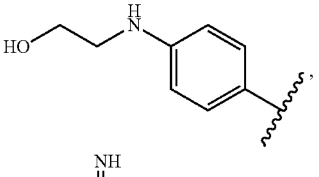,
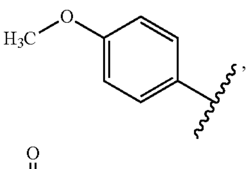,
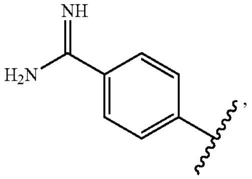,
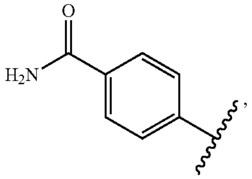, -continued

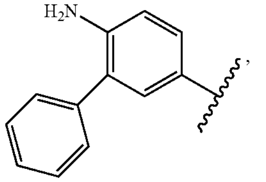,
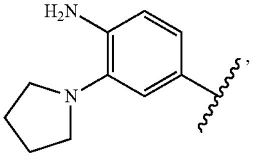,
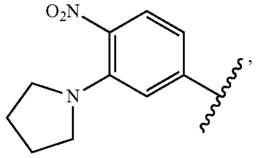,
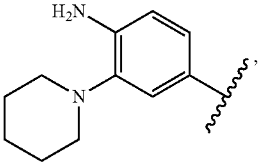,
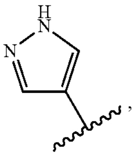,
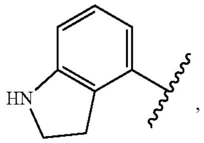,
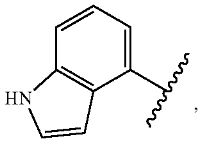,
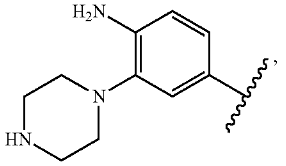,
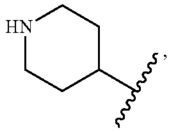,
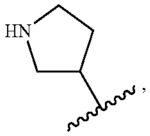,
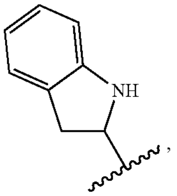,
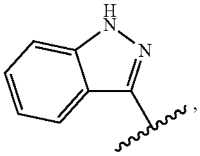,
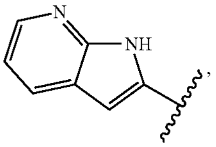,
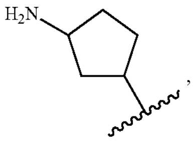,
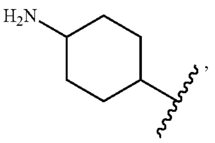,
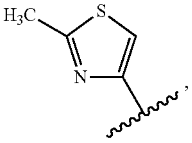,
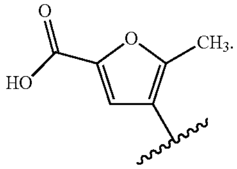.

As an even more specific example, $X_1$ may be selected from the following structures:

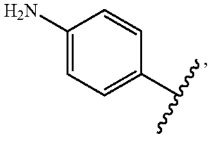,
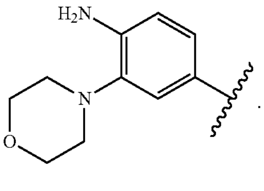.

3) $X_4$

In formula 1, $X_4$ corresponds to a side chain of a second residue of the N-degron, and may have a ring or chain structure so as to be able to fill a binding space when binding to a UBR box. In this case, as an example, the ring or chain structure may enhance the binding strength by introducing a moiety that has an electric charge or forms a hydrogen bond. Additionally, $X_4$ may include a structure capable of performing a role of binding to a linker when the compound of the present specification is later used in combination with another material.

As an example, the $X_4$ may be an optionally substituted with one or more $R_3$ or unsubstituted phenyl, cycloalkyl or heterocyclyl, as a specific example, the $X_4$ may be selected from an optionally substituted with one or more $R_3$ or unsubstituted phenyl, cyclohexyl, cyclopentyl, furanyl, thiazolyl, 1H-pyrazolyl, pyrrolidinyl, piperidinyl, piperazinyl, morpholinyl, indolinyl, 1H-indolinyl, 1H-indolyl, 1H-indazolyl, isoindolinyl, indolin-2-only, 2,3-dihydro-1H-indenyl and 1H-pyrrolopyridinyl. In this case, each $R_3$ may be independently selected from alkyl, alkoxy, amino, halo, hydroxyl, alkylamino, dialkylamino, —$NO_2$, CONR'R", —$CO_2R'$, —NHCOR', phenyl or heterocycloalkyl. As an example, each $R_3$ may be independently selected from hydroxyl, fluoro, chloro, bromo, amino, methyl, ethyl, isopropyl, methoxy, ethoxy, isopropyloxy, alkylamino, dialkylamino, —$NO_2$, —C(═O)$NH_2$, —$CO_2R'$, —NHCOR', —CONR'R" and phenyl. As a specific example, $R_3$ may be a hydroxyl. In this case, each R' and R" may be independently —H or alkyl.

As a more specific example, the $X_4$ may be selected from the following structures:

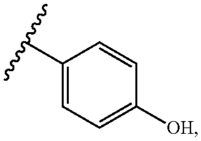,
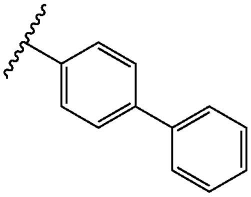,
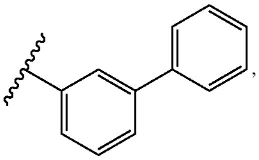,
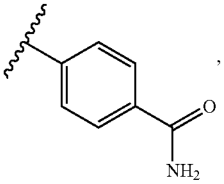,
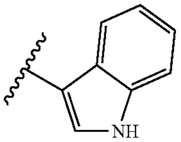,
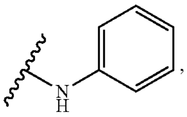,
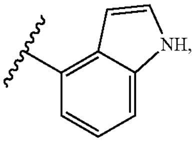,
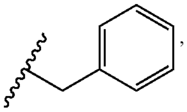,
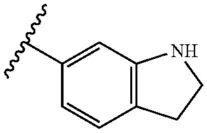,
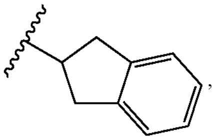, -continued

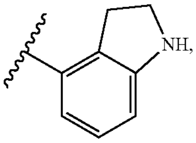,
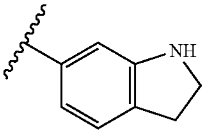,
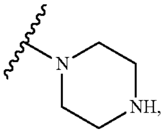,
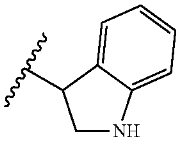,
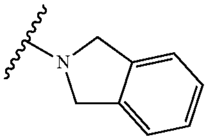,
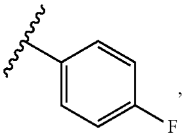,
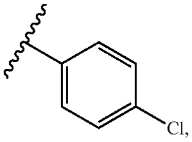,
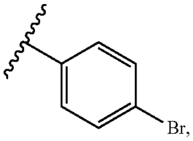,
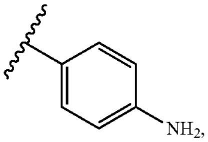,
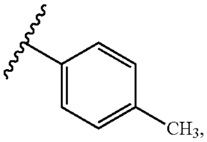,
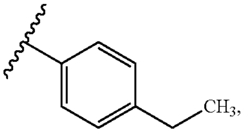,
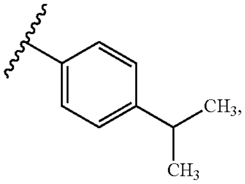,
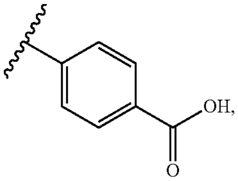,
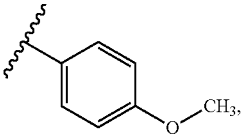,
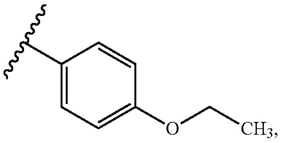,
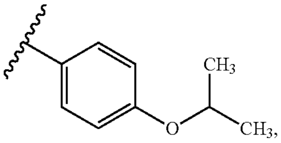,
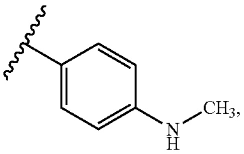,
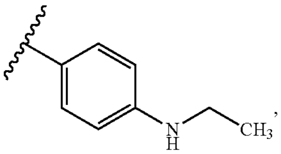,
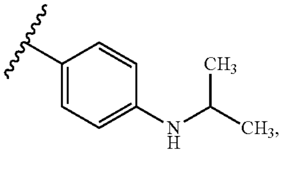,
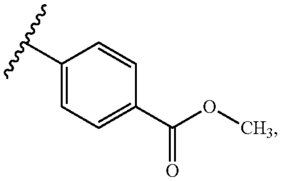, -continued

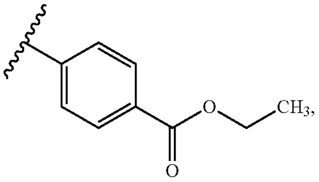
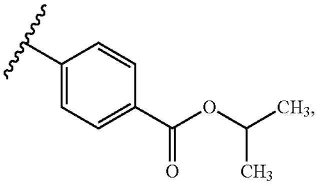
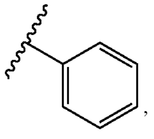
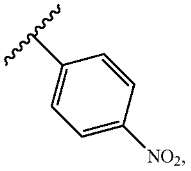
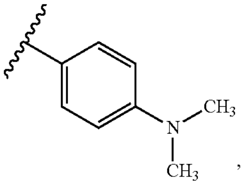
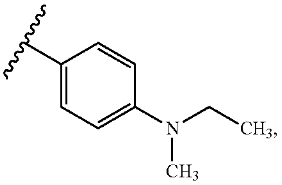
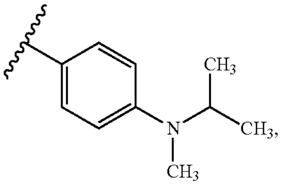
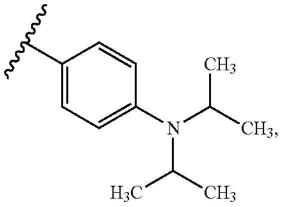
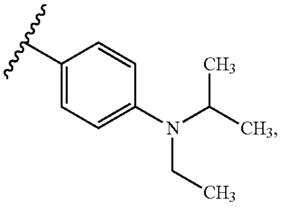
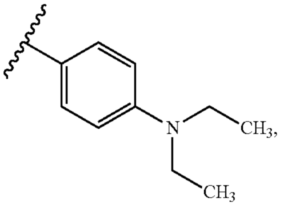
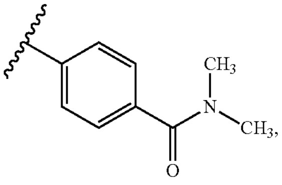
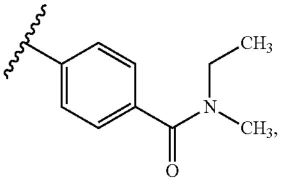
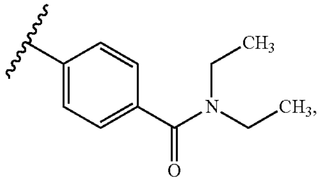
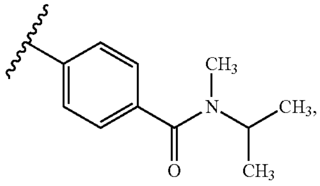

-continued

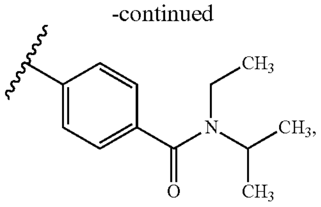
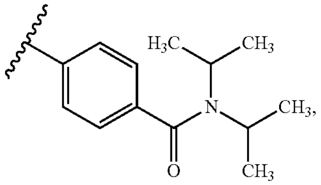
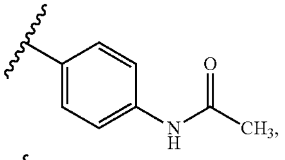
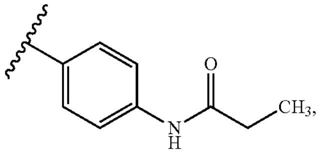
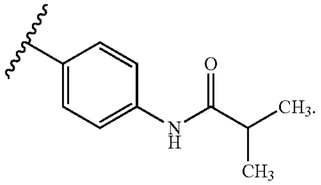

As an even more specific example, $X_4$ may be selected from those described below:

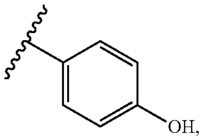
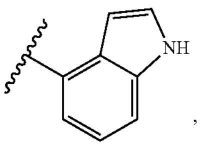
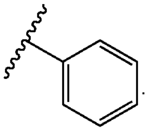

The compound disclosed herein may be present in the form of a stereoisomer or a salt thereof, and the form of the isomer or salt of such a compound is included in the scope of the present specification.

III. SPECIFIC EXAMPLE OF COMPOUND AS UBR BOX DOMAIN LIGAND

1. Specific Examples of Compound

The following content shows specific examples of the compound disclosed herein. The following specific examples are exemplary structures for an easy understanding of the compound disclosed herein, and the scope of the compound disclosed herein is not limited to the following examples.

As a specific example, the compound disclosed herein may have a structure of [formula 1-1]:

[formula 1-1]

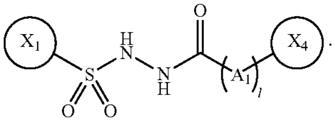

In this case, in the compound, A1 is $CH_2$ or NH, and I is an integer of 0 or 1.

$X_1$ and $X_4$ are applied in the same manner as the content described in the 2) $X_1$ and 3) $X_4$ of the contents II. UBR box domain ligand.

As an even more specific example, specific exemplary compounds of [formula 1-1] may be selected from those described below.

TABLE 1

| Specific exemplary compounds of formula [1-1 ] | |
|---|---|
| Compound No. | Compound |
| 1 | 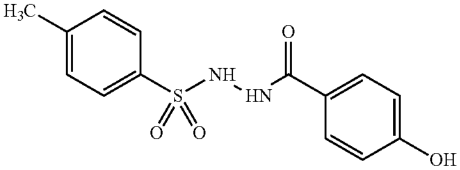 [SMILES: Cc1ccc(S(=O)(=O)NNC(=O)c2ccc(O)cc2)cc1] N'-(4-hydroxybenzoyl)-4-methylbenzenesulfonohydrazide |
| 2 | 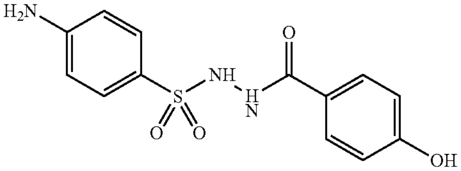 [SMILES: Nc1ccc(S(=O)(=O)NNC(=O)c2ccc(O)cc2)cc1] 4-amino-N'-(4-hydroxybenzoyl)benzenesulfonohydrazide |
| 3 | 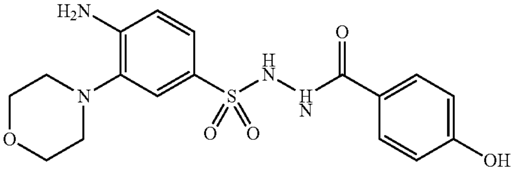 [SMILES: Nc1ccc(S(=O)(=O)NNC(=O)c2ccc(O)cc2)cc1N1CCOCC1] 4-amino-N'-(4-hydroxybenzoyl)-3-morpholinobenzenesulfonohydrazide |
| 4 | 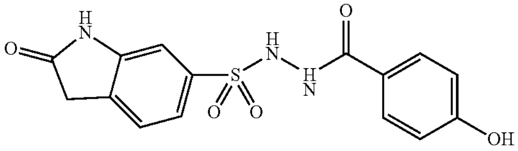 [SMILES: O=C1Cc2ccc(S(=O)(=O)NNC(=O)c3ccc(O)cc3)cc2N1] N'-(4-hydroxybenzoyl)-2-oxoindoline-5-sulfonohydrazide |
| 5 | 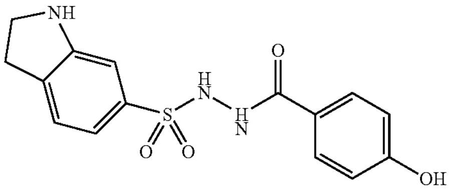 [SMILES: O=C(NNS(=O)(=O)c1ccc2c(c1)NCC2)c1ccc(O)cc1] N'-(4-hydroxybenzoyl)indoline-5-sulfonohydrazide |

TABLE 1-continued

| Specific exemplary compounds of formula [1-1 ] | |
|---|---|
| Compound No. | Compound |
| 6 | 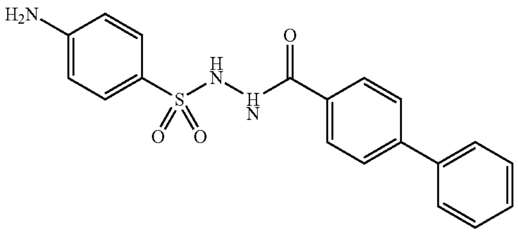 [SMILES: Nc1ccc(S(=O)(=O)NNC(=O)c2ccc(-c3ccccc3)cc2)cc1] N'-([1,1'-biphenyl]-4-carbonyl)-4-aminobenzenesulfonohydrazide |
| 7 | 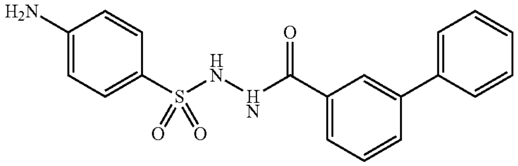 [SMILES: Nc1ccc(S(=O)(=O)NNC(=O)c2cccc(-c3ccccc3)c2)cc1] N'-([1,1'-biphenyl]-3-carbonyl)-4-aminobenzenesulfonohydrazide |
| 8 | 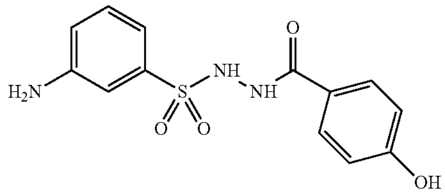 [SMILES: Nc1cccc(S(=O)(=O)NNC(=O)c2ccc(O)cc2)c1] 3-amino-N'-(4-hydroxybenzoyl)benzenesulfonohydrazide |
| 9 | 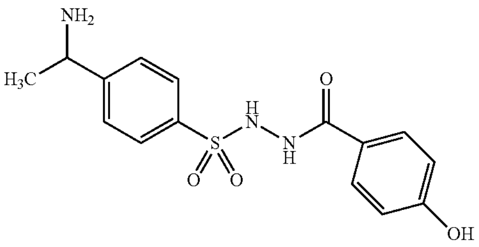 [SMILES: CC(N)c1ccc(S(=O)(=O)NNC(=O)c2ccc(O)cc2)cc1] 4-(1-aminoethyl)-N'-(4-hydroxybenzoyl)benzenesulfonohydrazide |
| 10 | 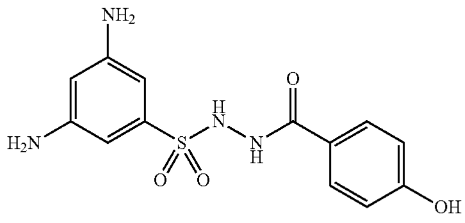 [SMILES: Nc1cc(N)cc(S(=O)(=O)NNC(=O)c2ccc(O)cc2)c1] 3,5-diamino-N'-(4-hydroxybenzoyl)benzenesulfonohydrazide |

TABLE 1-continued

Specific exemplary compounds of formula [1-1 ]

| Compound No. | Compound |
| --- | --- |
| 11 | 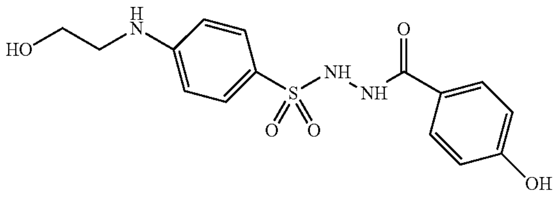 [SMILES: O=C(NNS(=O)(=O)c1ccc(NCCO)cc1)c1ccc(O)cc1]<br>N'-(4-hydroxybenzoyl)-4-((2-hydroxyethyl)amino)benzenesulfonohydrazide |
| 13 | 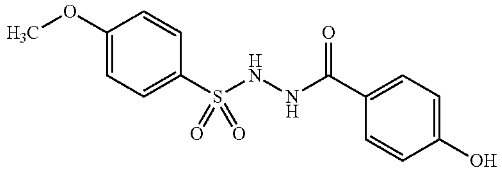 [SMILES: COc1ccc(S(=O)(=O)NNC(=O)c2ccc(O)cc2)cc1]<br>N'-(4-hydroxybenzoyl)-4-methoxybenzenesulfonohydrazide |
| 14 | 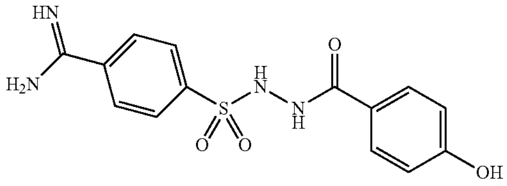 [SMILES: N=C(N)c1ccc(S(=O)(=O)NNC(=O)c2ccc(O)cc2)cc1]<br>4-((2-(4-hydroxybenzoyl)hydrazinyl)sulfonyl)benzimidamide |
| 15 | 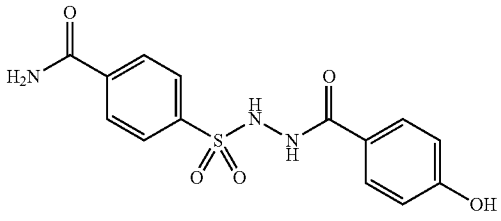 [SMILES: NC(=O)c1ccc(S(=O)(=O)NNC(=O)c2ccc(O)cc2)cc1]<br>4-((2-(4-hydroxybenzoyl)hydrazinyl)sulfonyl)benzamide |
| 17 | 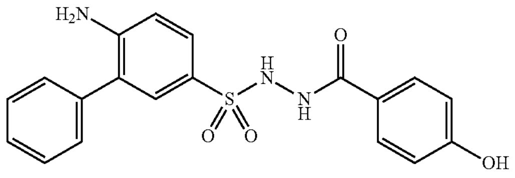 [SMILES: Nc1ccc(S(=O)(=O)NNC(=O)c2ccc(O)cc2)cc1-c1ccccc1]<br>6-amino-N'-(4-hydroxybenzoyl)-[1,1'-biphenyl]-3-sulfonohydrazide |

TABLE 1-continued

| Specific exemplary compounds of formula [1-1 ] | |
|---|---|
| Compound No. | Compound |
| 18 | 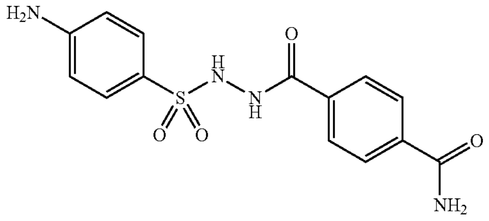 [SMILES: NC(=O)c1ccc(C(=O)NNS(=O)(=O)c2ccc(N)cc2)cc1] 4-(2-((4-aminophenyl)sulfonyl)hydrazine-1-carbonyl)benzamide |
| 20 | 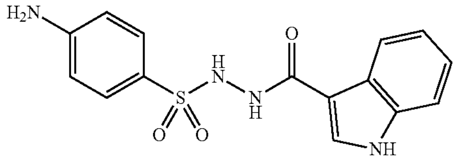 [SMILES: Nc1ccc(S(=O)(=O)NNC(=O)c2c[nH]c3ccccc23)cc1] 4-amino-N'-(1H-indole-3-carbonyl)benzenesulfonohydrazid |
| 21 | 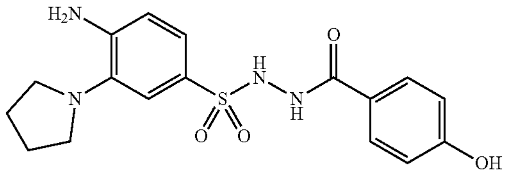 [SMILES: O=C(NNS(=O)(=O)c1ccc([N+](=O)[O-])c(N2CCCC2)c1)c1ccc(O)cc1] 4-amino-N'-(4-hydroxybenzoyl)-3-(pyrrolidin-1-yl)benzenesulfonohydrazide |
| 22 | 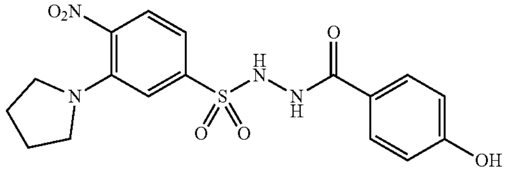 N'-(4-hydroxybenzoyl)-4-nitro-3-(pyrrolidin-l-yl)benzenesulfonohydrazide |
| 23 | 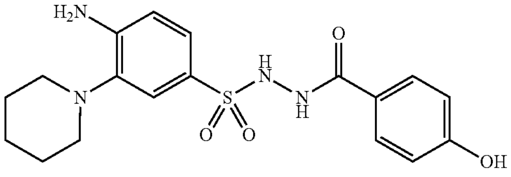 [SMILES: Nc1ccc(S(=O)(=O)NNC(=O)c2ccc(O)cc2)cc1N1CCCCC1] 4-amino-N'-(4-hydroxybenzoyl)-3-(piperidin-1-yl)benzenesulfonohydrazide |
| 24 | 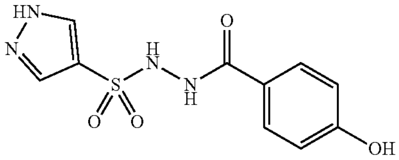 [SMILES: O=C(NNS(=O)(=O)c1cn[nH]c1)c1ccc(O)cc1] N'-(4-hydroxybenzoyl)-1H-pyrazole-4-sulfonohydrazide |

TABLE 1-continued

| Specific exemplary compounds of formula [1-1 ] | |
|---|---|
| Compound No. | Compound |
| 25 | 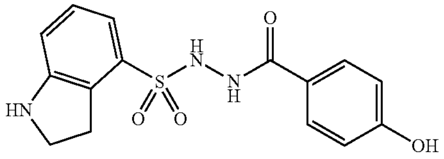 [SMILES: O=C(NNS(=O)(=O)c1cccc2c1CCN2)c1ccc(O)cc1]<br>N'-(4-hydroxybenzoyl)indoline-4-sulfonohydrazide |
| 26 | 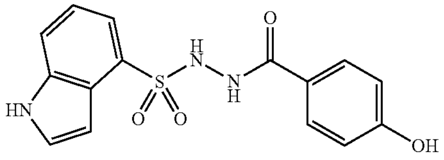 [SMILES: O=C(NNS(=O)(=O)c1cccc2[nH]ccc12)c1ccc(O)cc1]<br>N'-(4-hydroxybenzoyl)-1H-indole-4-sulfonohydrazide |
| 27 | 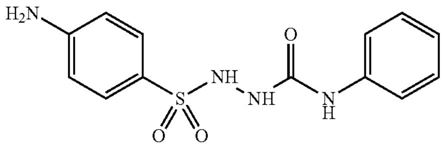 [SMILES: Nc1ccc(S(=O)(=O)NNC(=O)Nc2ccccc2)cc1]<br>2-((4-aminophenyl)sulfonyl)-N-phenylhydrazine-1-carboxamide |
| 28 | 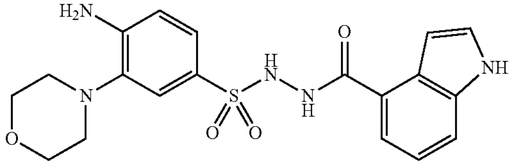 [SMILES: Nc1ccc(S(=O)(=O)NNC(=O)c2cccc3[nH]ccc23)cc1N1CCOCC1]<br>4-amino-N'-(1H-indole-4-carbonyl)-3-morpholinobenzenesulfonohydrazide |
| 29 | 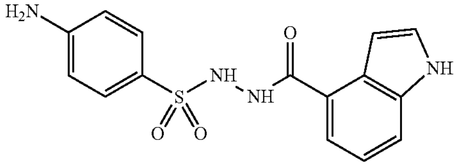 [SMILES: Nc1ccc(S(=O)(=O)NNC(=O)c2cccc3[nH]ccc23)cc1]<br>4-amino-N'-(1H-indole-4-carbonyl)benzenesulfonohydrazide |
| 30 | 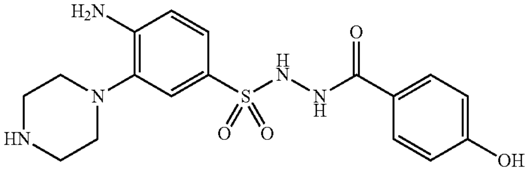 [SMILES: Nc1ccc(S(=O)(=O)NNC(=O)c2ccc(O)cc2)cc1N1CCNCC1]<br>4-amino-N'-(4-hydroxybenzoyl)-3-(piperazin-1-yl)benzenesulfonohydrazide |

TABLE 1-continued

| Specific exemplary compounds of formula [1-1 ] | |
|---|---|
| Compound No. | Compound |
| 31 | 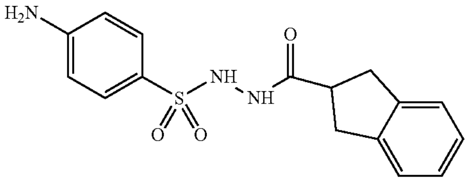 [SMILES: Nc1ccc(S(=O)(=O)NNC(=O)C2Cc3ccccc3C2)cc1]<br>4-amino-N'-(2,3-dihydro-1H-indene-2-carbonyl)benzenesulfonohydrazide |
| 32 | 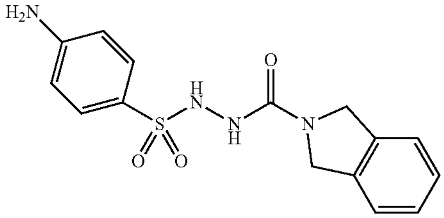 [SMILES: Nc1ccc(S(=O)(=O)NNC(=O)N2Cc3ccccc3C2)cc1]<br>4-amino-N'-(isoindoline-2-carbonyl)benzenesulfonohydrazide |
| 33 | 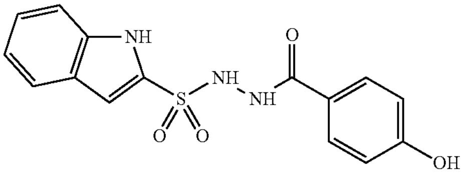 [SMILES: O=C(NNS(=O)(=O)c1cc2ccccc2[nH]1)c1ccc(O)cc1]<br>N'-(4-hydroxybenzoyl)-1H-indole-2-sulfonohydrazide |
| 34 | 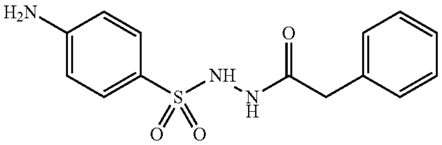 [SMILES: Nc1ccc(S(=O)(=O)NNC(=O)Cc2ccccc2)cc1]<br>4-amino-N'-(2-phenylacetyl)benzenesulfonohydrazide |
| 35 | 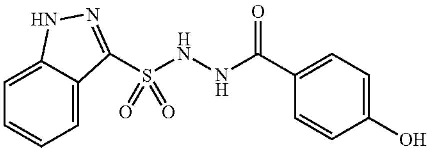 [SMILES: O=C(NNS(=O)(=O)c1n[nH]c2ccccc12)c1ccc(O)cc1]<br>N'-(4-hydroxybenzoyl)-1H-indazole-3-sulfonohydrazide |
| 36 | 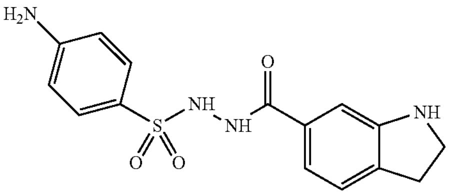 [SMILES: Nc1ccc(S(=O)(=O)NNC(=O)c2ccc3c(c2)NCC3)cc1]<br>4-amino-N'-(indoline-6-carbonyl)benzenesulfonohydrazide |

TABLE 1-continued

| Specific exemplary compounds of formula [1-1 ] | |
|---|---|
| Compound No. | Compound |
| 37 | 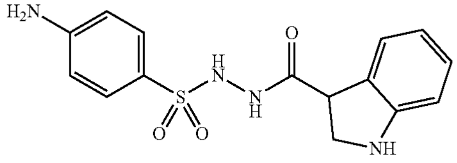 [SMILES: Nc1ccc(S(=O)(=O)NNC(=O)C2CNc3ccccc32)cc1]<br>4-amino-N'-(indoline-3-carbonyl)benzenesulfonohydrazide |
| 38 | 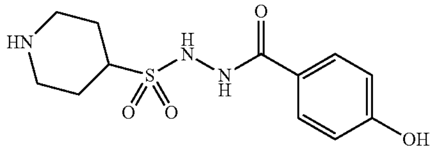 [SMILES: O=C(NNS(=O)(=O)C1CCNCC1)c1ccc(O)cc1]<br>N'-(4-hydroxybenzoyl)piperidine-4-sulfonohydrazide |
| 39 | 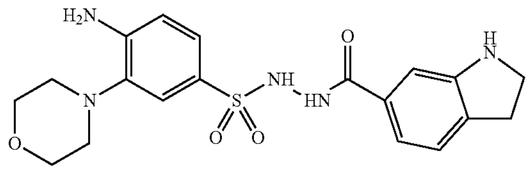 [SMILES: Nc1ccc(S(=O)(=O)NNC(=O)c2ccc3c(c2)NCC3)cc1N1CCOCC1]<br>4-amino-N'-(indoline-6-carbonyl)-3-morpholinobenzenesulfonohydrazide |
| 40 | 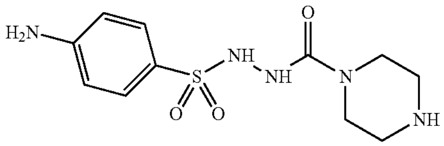 [SMILES: Nc1ccc(S(=O)(=O)NNC(=O)N2CCNCC2)cc1]<br>4-amino-N'-(piperazine-1-carbonyl)benzenesulfonohydrazide |
| 41 | 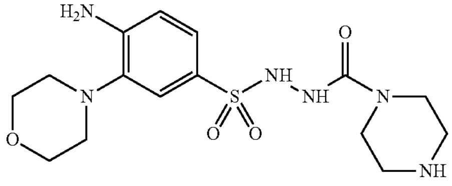 [SMILES: Nc1ccc(S(=O)(=O)NNC(=O)N2CCNCC2)cc1N1CCOCC1]<br>4-amino-3-morpholino-N'-(piperazine-1-carbonyl)benzenesulfonohydrazide |
| 42 | 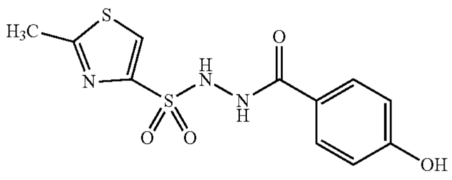 [SMILES: Cc1nc(S(=O)(=O)NNC(=O)c2ccc(O)cc2)cs1]<br>N'-(4-hydroxybenzoyl)-2-methylthiazole-4-sulfonohydrazide |

TABLE 1-continued

| Specific exemplary compounds of formula [1-1 ] | |
|---|---|
| Compound No. | Compound |
| 43 | 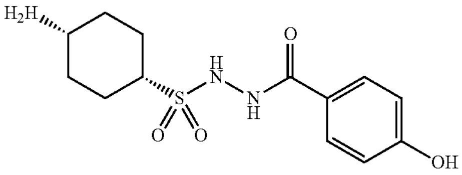 [SMILES: O=C(NNS(=O)(=O)C1CCCCC1)c1ccc(O)cc1] (1S,4S)-4-amino-N'-(4-hydroxybenzoyl)cyclohexane-1-sulfonohydrazide |
| 44 | 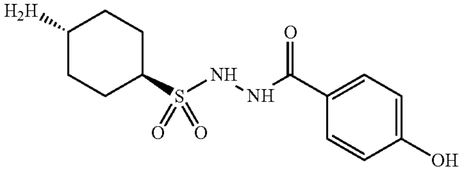 [SMILES: O=C(NNS(=O)(=O)C1CCCCC1)c1ccc(O)cc1] (1R,4R)-4-amino-N'-(4-hydroxybenzoyl)cyclohexane-1-sulfonohydrazide |
| 45 | 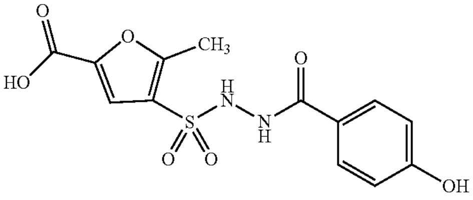 [SMILES: Cc1oc(C(=O)O)cc1S(=O)(=O)NNC(=O)c1ccc(O)cc1] 4-((2-(4-hydroxybenzoyl)hydrazinyl)sulfonyl)-5-methylfuran-2-carboxylic acid |
| 46 | 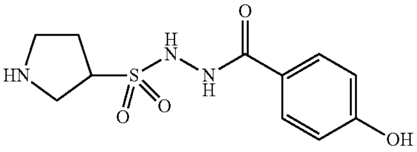 [SMILES: O=C(NNS(=O)(=O)C1CCNC1)c1ccc(O)cc1] N'-(4-hydroxybenzoyl)pyrrolidine-3-sulfonohydrazide |
| 47 | 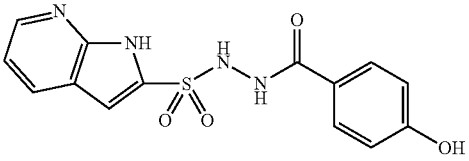 [SMILES: O=C(NNS(=O)(=O)c1cc2cccnc2[nH]1)c1ccc(O)cc1] N'-(4-hydroxybenzoyl)-1H-pyrrolo[2,3-b]pyridine-2-sulfonohydrazide |
| 52 | 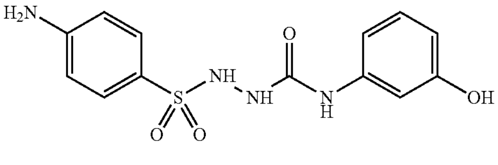 [SMILES: Nc1ccc(S(=O)(=O)NNC(=O)Nc2cccc(O)c2)cc1] 2-((4-aminophenyl)sulfonyl)-N-(3-hydroxyphenyl)hydrazine-1-carboxamide |

TABLE 1-continued

| Specific exemplary compounds of formula [1-1 ] | |
|---|---|
| Compound No. | Compound |
| 53 | 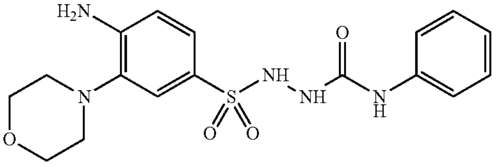 [SMILES: Nc1ccc(S(=O)(=O)NNC(=O)Nc2ccccc2)cc1N1CCOCC1]<br>2-((4-amino-3-morpholinophenyl)sulfonyl)-N-phenylhydrazine-1-carboxamide |

In another specific example, the compound of the present specification may have the structure of [formula 1-2]:

[formula 1-2]

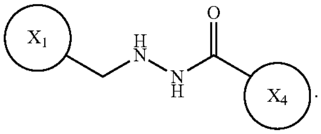

In this case, the $X_1$ and $X_4$ of the compound are applied in the same manner as the content described in the 2) $X_1$ and 3) $X_4$ of the contents II. UBR box domain ligand.

Specific exemplary compounds of [formula 1-2] may be selected from the following:

TABLE 2

| Specific exemplary compounds of formula [1 -2] | |
|---|---|
| Compound No. | Compound |
| 19 | 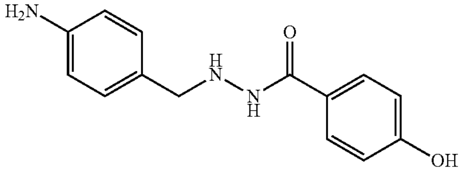 [SMILES: Nc1ccc(CNNC(=O)c2ccc(O)cc2)cc1]<br>N'-(4-aminobenzyl)-4-hydroxybenzohydrazide |
| 48 | 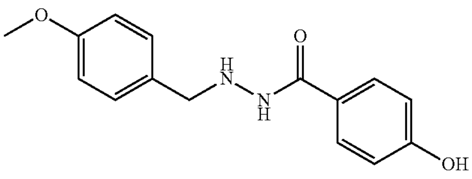 [SMILES: COc1ccc(CNNC(=O)c2ccc(O)cc2)cc1]<br>4-hydroxy-N'-(4-methoxybenzyl)benzohydrazide |

TABLE 2-continued

| Specific exemplary compounds of formula [1 -2] | |
|---|---|
| Compound No. | Compound |
| 49 | 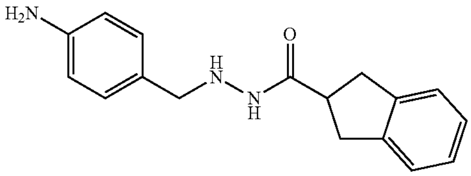 [SMILES: Nc1ccc(CNNC(=O)C2Cc3ccccc3C2)cc1]<br>N'-(4-aminobenzyl)-2,3-dihydro-1H-indedn-2-carbohydrazide |

In another specific example, the compound of the present specification may have the structure of [formula 1-3]:

[formula 1-3]

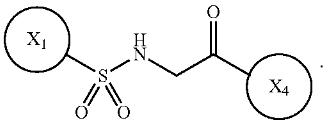

In this case, the $X_1$ and $X_4$ of the compound are applied in the same manner as the content described in the 2) $X_1$ and 3) $X_4$ of the contents II. UBR box domain ligand.

Specific exemplary compounds of [formula 1-3] may be selected from the following:

TABLE 3

| Specific exemplary compounds of [formula 1-3] | |
|---|---|
| Com pound No. | Compound |
| 12 | 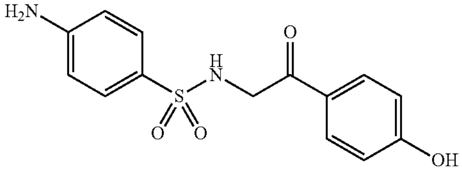 [SMILES: Nc1ccc(S(=O)(=O)NCC(=O)c2ccc(O)cc2)cc1]<br>4-amino-N-(2-(4-hydroxyphenyl)-2-oxoethyl)benzenesulfonamide |

TABLE 3-continued

| Specific exemplary compounds of [formula 1-3] | |
|---|---|
| Com pound No. | Compound |
| 50 | 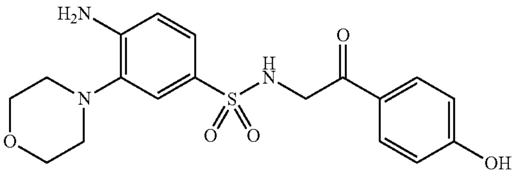 [SMILES: Nc1ccc(S(=O)(=O)NCC(=O)c2ccc(O)cc2)cc1N1CCOCC1]<br>4-amino-N-(2-(4-hydroxyphenyl)-2-oxoethyl)-3-morpholinobenzenesulfonamide |
| 51 | 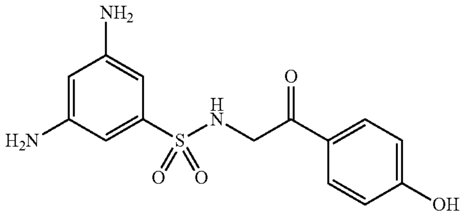 [SMILES: Nc1cc(N)cc(S(=O)(=O)NCC(=O)c2ccc(O)cc2)c1]<br>3,5-diamino-N-(2-(4-hydroxyphenyl)-2-oxoethyl)benzenesulfonamide |

In another specific example, the compound of the present specification may have the structure of [formula 1-4]:

[formula 1-4]

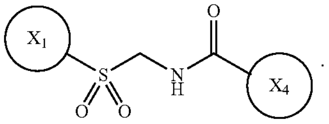

Specific exemplary compounds of [formula 1-4] may be selected from the following:

TABLE 4

| Specific exemplary compounds of [formula 1-4] | |
|---|---|
| Com pound No. | Compound |
| 16 | 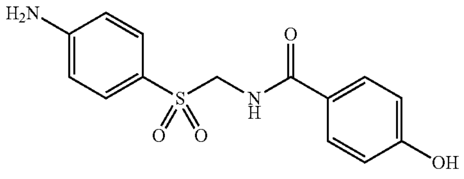 [SMILES: Nc1ccc(S(=O)(=O)CNC(=O)c2ccc(O)cc2)cc1]<br>N-(((4-aminophenyl)sulfonyl)methyl)-4-hydroxybenzamide |

TABLE 4-continued

| Specific exemplary compounds of [formula 1-4] | |
|---|---|
| Com pound No. | Compound |
| 54 | 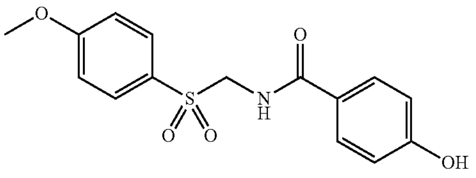 [SMILES: COc1ccc(S(=O)(=O)CNC(=O)c2ccc(O)cc2)cc1]<br>4-hydroxy-N-(((4-methoxyphenyl)sulfonyl)methyl)benzamide |
| 55 | 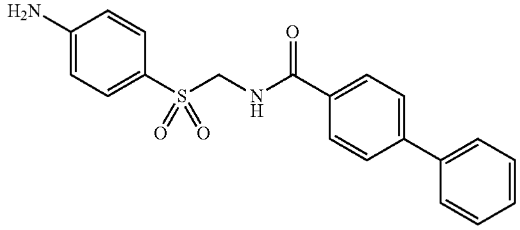 [SMILES: Nc1ccc(S(=O)(=O)CNC(=O)c2ccc(-c3ccccc3)cc2)cc1]<br>N-(((4-aminophenyl)sulfonyl)methyl)-[1,1'-biphenyl]-4-carboxamide |

In this case, as the compound, a form of a possible isomer thereof or a form of a mixture thereof may be considered. For example, all stereoisomers including enantiomers and diastereomers, or mixtures thereof (for example, racemic mixtures) may be considered.

2. Salt of Compound

As the compound disclosed herein, a form of a salt thereof may be considered. In this case, the salt contains a pharmaceutically acceptable salt. The salt disclosed herein includes an acid addition salt or a basic addition salt. An exemplary acid forming the salt includes hydrochloric acid, sulfuric acid, phosphoric acid, glycolic acid, lactic acid, pyruvic acid, citric acid, succinic acid, glutaric acid and the like, and an exemplary base forming the salt includes lithium, sodium, potassium, calcium, magnesium, methylamine, trimethylamine and the like. However, the acid and the base are not limited thereto and may be easily selected by a person skilled in the art.

IV. USE OF COMPOUND

1. Inhibition of UBR Box Domain Substrate Binding

Composition for Inhibition of UBR Box Domain Substrate Binding

The compound disclosed herein may be used in the preparation of a composition for inhibition of UBR box domain substrate binding. As an example, the composition including the compound disclosed herein may be used to inhibit the UBR box domain substrate binding by binding to the UBR box domain. As another example, the composition including the compound may be used for a use of preventing the substrate which is bound to the UBR box domain and degraded from being degraded. As a specific example, the composition including the compound may be used for a use of preventing the substrate which is bound to the UBR box domain from being degraded by the ubiquitin-proteasome pathway.

As a specific example, the composition including the compound disclosed herein may be used for a use of inhibiting the binding of a substrate having an N-terminal residue that binds to a UBR box domain. As a specific example, the composition including the compound disclosed herein may be used for a use of inhibiting the binding of a substrate having an N-terminal residue such as arginine (Arg), lysine (Lys), histidine (His), tryptophan (Trp), phenylalanine (Phe), tyrosine (Tyr), leucine (Leu), and isoleucine (Ile). However, the use is not limited thereto, the composition may be used for a use of inhibiting the binding of a material known as a substrate of the UBR box domain in the art.

With reference to the examples, it can be confirmed that the compounds disclosed herein inhibit the degradation of the substrate by binding to UBR (see FIGS. 1 to 19).

2. Treatment of UBR-Related Disease

The compound of the present specification or a salt thereof has a property of binding to a UBR box domain. That is, the compound of the present specification is a compound that functions as a ligand binding to the UBR box domain. Therefore, these compounds can be used to inhibit the degradation of proteins that are degraded by binding to the UBR box domain in the body, and such a mechanism may be used to treat a UBR-related disease.

1) Pharmaceutical Composition

The compound disclosed herein may be used in the preparation of a pharmaceutical composition for treating a subject in need thereof.

In this case, the treatment includes having an effect of ameliorating the symptoms of a particular medical condition or delaying the progression of the disease. In this case, the subject includes a human and a non-human animal. In this case, the pharmaceutical composition may include a carrier, an excipient and/or an additive, which are pharmaceutically acceptable, together with the aforementioned compound. The carrier, the excipient and the additive, which are pharmaceutically acceptable, include water, saline, glycol, glycerol, animal and vegetable fats, oils, starches, and the like, but are not limited thereto, and include all acceptable carriers, excipients and/or additives known in the art, which are pharmaceutically acceptable.

2) Treatment Method

The present specification provides a treatment method, including administering the compound disclosed herein or a pharmaceutically acceptable salt thereof to a subject in need thereof. In this case, administration of the compound or a pharmaceutically acceptable salt thereof may have an effect of alleviating the symptoms of a specific medical condition or delaying the progression of the disease compared to a subject who is not administered the compound or salt thereof. In this case, the subject includes a human and a non-human animal.

—UBR-Related Disease

As an example, the present specification provides a treatment method including administering the compound or a pharmaceutically acceptable salt thereof to a subject having a UBR-related disease. That is, the compound disclosed herein or a pharmaceutically acceptable salt thereof may be used to treat a UBR-related disease. As a specific example, the compound or a pharmaceutically acceptable salt thereof may be used to treat a specific disease to be treated by inhibiting the degradation of proteins that are degraded by binding to the UBR box domain.

The specific disease includes muscle loss caused by muscular dystrophy (Becker, Congennital, Duchenne, Distal, Emery-Dreifuss, Facioscapulohumeral, Limb-girdle, myotonic, ocuophargyngeal), muscle wasting diseases mediated by muscle loss or degradation including sarcopenia or cancer cachexia, diseases caused by excessive protein degradation including liposarcoma, cystic fibrosis, Johanson-Blizzard syndrome, obstructive urinary tract disease (urethral obstruction sequence), autoimmune pancreatitis or known diseases related to the UBR box and UBR protein including Usher syndrome.

As an example, the compound or a pharmaceutically acceptable salt thereof may be used to treat muscle loss mediated by UBR. For example, rapid loss of muscle mass accompanied by disease conditions such as cancer, sepsis, and hyperthyroidism is associated with an increase in degradation of intramuscular proteins, which is known to be associated with activation of a ubiquitin proteasome system. In this case, it is known that ubiquitin binding is increased particularly by activation of the N-end rule pathway, resulting in the occurrence of muscle loss [ALFRED L. GOLDBERG et al. 1998, 1999]. Accordingly, the compound disclosed herein or a pharmaceutically acceptable salt thereof may be used to treat the disease by preventing activation of the muscle loss pathway by binding to the UBR box domain. However, the present invention is not limited thereto, and the specific disease includes all diseases known as a disease related to UBR in the art.

V. EXAMPLES

Example 1. Synthesis of Compounds

TABLE 5

List of Compounds

| No. | Name of compounds |
|---|---|
| 1 | N'-(4-hydroxybenzoyl)-4-methylbenzenesulfonohydrazide |
| 2 | 4-amino-N'-(4-hydroxybenzoyl)benzenesulfonohydrazide |
| 3 | 4-amino-N'-(4-hydroxybenzoyl)-3-morpholinobenzenesulfonohydrazide |
| 4 | N'-(4-hydroxybenzoyl)-2-oxoindoline-5-sulfonohydrazide |
| 5 | N'-(4-hydroxybenzoyl)indoline-5-sulfonohydrazide |
| 6 | N'-([1,1'-biphenyl]-4-carbonyl)-4-aminobenzenesulfonohydrazide |
| 7 | N'-([1,1'-biphenyl]-3-carbonyl)-4-aminobenzenesulfonohydrazide |
| 8 | 3-amino-N'-(4-hydroxybenzoyl)benzenesulfonohydrazide |
| 9 | 4-(1-aminoethyl)-N'-(4-hydroxybenzoyl)benzenesulfonohydrazide |
| 10 | 3,5-diamino-N'-(4-hydroxybenzoyl)benzenesulfonohydrazide |
| 11 | N'-(4-hydroxybenzoyl)-4-((2-hydroxyethyl)amino)benzenesulfonohydrazide |
| 12 | 4-amino-N-(2-(4-hydroxyphenyl)-2-oxoethyl)benzenesulfonamide |
| 13 | N'-(4-hydroxybenzoyl)-4-methoxybenzenesulfonohydrazide |
| 14 | 4-((2-(4-hydroxybenzoyl)hydrazinyl)sulfonyl)benzimidamide |
| 15 | 4-((2-(4-hydroxybenzoyl)hydrazinyl)sulfonyl)benzamide |
| 16 | N-(((4-aminophenyl)sulfonyl)methyl)-4-hydroxybenzamide |
| 17 | 6-amino-N'-(4-hydroxybenzoyl)-[1,1'-biphenyl]-3-sulfonohydrazide |
| 18 | 4-(2-((4-aminophenyl)sulfonyl)hydrazine-1-carbonyl)benzamide |
| 19 | N'-(4-aminobenzyl)-4-hydroxybenzohydrazide |
| 20 | 4-amino-N'-(1H-indole-3-carbonyl)benzenesulfonohydrazide |
| 21 | 4-amino-N'-(4-hydroxybenzoyl)-3-(pyrrolidin-1-yl)benzenesulfonohydrazide |
| 22 | N'-(4-hydroxybenzoyl)-4-nitro-3-(pyrrolidin-1-yl)benzenesulfonohydrazide |
| 23 | 4-amino-N'-(4-hydroxybenzoyl)-3-(piperidin-1-yl)benzenesulfonohydrazide |
| 24 | N'-(4-hydroxybenzoyl)-1H-pyrazole-4-sulfonohydrazide |
| 25 | N'-(4-hydroxybenzoyl)indoline-4-sulfonohydrazide |
| 26 | N'-(4-hydroxybenzoyl)-1H-indole-4-sulfonohydrazide |
| 27 | 2-((4-aminophenyl)sulfonyl)-N-phenylhydrazine-1-carboxamide |
| 28 | 4-amino-N-(1H-indole-4-carbonyl)-3-morpholinobenzenesulfonohydrazide |
| 29 | 4-amino-N'-(indoline-4-carbonyl)benzenesulfonohydrazide |

TABLE 5-continued

| List of Compounds | |
|---|---|
| No. | Name of compounds |
| 30 | 4-amino-N'-(4-hydroxybenzoyl)-3-(piperazin-1-yl)benzenesulfonohydrazide |
| 31 | 4-amino-N'-(2,3-dihydro-1H-indene-2-carbonyl)benzenesulfonohydrazide |
| 32 | 4-amino-N'-(isoindoline-2-carbonyl)benzenesulfonohydrazide |
| 33 | N'-(4-hydroxybenzoyl)-1H-indole-2-sulfonohydrazide |
| 34 | 4-amino-N'-(2-phenylacetyl)benzenesulfonohydrazide |
| 35 | N-(4-hydroxybenzoyl)-1H-indazole-3-sulfonohydrazide |
| 36 | 4-amino-N'-(indoline-6-carbonyl)benzenesulfonohydrazide |
| 37 | 4-amino-N'-(indoline-3-carbonyl)benzenesulfonohydrazide |
| 38 | N'-(4-hydroxybenzoyl)piperidine-4-sulfonohydrazide |
| 39 | 4-amino-N'-(indoline-6-carbonyl)-3-morpholinobenzenesulfonohydrazide |
| 40 | 4-amino-N'-(piperazine-1-carbonyl)benzenesulfonohydrazide |
| 41 | 4-amino-3-morpholino-N'-(piperazine-1-carbonyl)benzenesulfonohydrazide |
| 42 | N'-(4-hydroxybenzoyl)-2-methylthiazole-4-sulfonohydrazide |
| 43 | (1S,4S)-4-amino-N'-(4-hydroxybenzoyl)cyclohexane-1-sulfonohydrazide |
| 44 | (1R,4R)-4-amino-N'-(4-hydroxybenzoyl)cyclohexane-1-sulfonohydrazide |
| 45 | 4-((2-(4-hydroxybenzoyl)hydrazinyl)sulfonyl)-5-methylfuran-2-carboxylic acid |
| 46 | N'-(4-hydroxybenzoyl)pyrrolidine-3-sulfonohydrazide |
| 47 | N'-(4-hydroxybenzoyl)-1H-pyrrolo[2,3-b]pyridine-2-sulfonohydrazide |
| 48 | 4-hydroxy-N'-(4-methoxybenzyl)benzohydrazide |
| 49 | N'-(4-aminobenzyl)-2,3-dihydro-1H-indene-2-carbohydrazide |
| 50 | 4-amino-N-(2-(4-hydroxyphenyl)-2-oxoethyl)-3-morpholinobenzenesulfonamide |
| 51 | 3,5-diamino-N-(2-(4-hydroxyphenyl)-2-oxoethyl)benzenesulfonamide |
| 52 | 2-((4-aminophenyl)sulfonyl)-N-(3-hydroxyphenyl)hydrazine-1-carboxamide |
| 53 | 2-((4-amino-3-morpholinophenyl)sulfonyl)-N-phenylhydrazine-1-carboxamide |
| 54 | 4-hydroxy-N-(((4-methoxyphenyl)sulfonyl)methyl)benzamide |
| 55 | N-(((4-aminophenyl)sulfonyl)methyl)-[1,1'-biphenyl]-4-carboxamide |

$^1$H NMR spectra were recorded on Bruker Avance III 400 MHz and Bruker Fourier 300 MHz and TMS was used as an internal standard. LCMS was taken on a quadrupole Mass Spectrometer on Agilent 1260HPLC and 6120MSD (Column: C18 (50×4.6 mm, 5 μm) operating in ES (+) or (−) ionization mode; T=30° C.; flow rate=1.5 mL/min; detected wavelength: 220 nm, 254 nm Experimental Example 1-1. Preparation of Compound 1 (N'-(4-hydroxybenzoyl)-4-methylbenzenesulfonohydrazide)

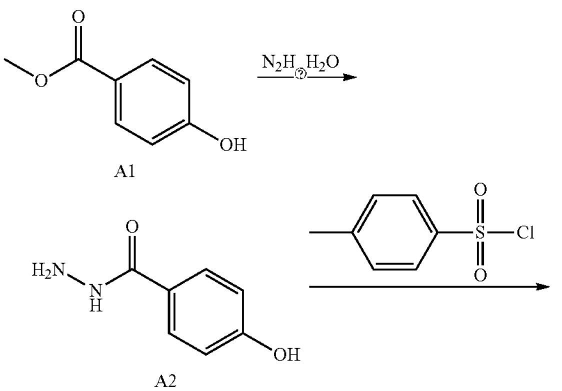

A1
A2

-continued

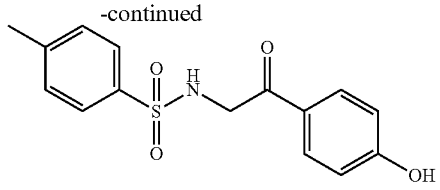
Compound 1

Step 1) Synthesis of A2

A mixture of A1 (methyl 4-hydroxybenzoate, 2.00 g, 13 mmol, 1.0 eq) and Hydrazine monohydrate (20 mL) was stirred at 100° C. for 16 hrs. The solvent was concentrated under reduced pressure to give crude product, which was purified by flash column (DCM/MeOH=50/1~1/1) to afford A2 (4-hydroxybenzohydrazide, 2.0 g, yield 60%) as a white solid. $^1$H NMR (DMSO-$d_6$, 400 MHz): δ 9.49 (s, 1H), 7.67-7.69 (m, 2H), 6.76-6.79 (m, 2H), 4.38 (br s, 2H).

Step 2) Synthesis of Compound 1

A mixture of $A_2$ (4-hydroxybenzohydrazide, 0.3 g, 1.97 mmol, 1.0 eq) and 4-methylbenzenesulfonyl chloride (0.3 g, 1.57 mmol, 0.8 eq) in pyridine (5 mL) was stirred at 80° C. for 16 hrs. Then to the mixture was added 1N HCl till pH=3 and extracted with EA (20 mL×3). The combined organic layers were washed with brine, dried over $Na_2SO_4$ and concentrated to give crude product (400 mg). About 130 mg of crude product was purified by prep-HPLC. The collected fraction was concentrated to remove most of $CH_3CN$. The residual fraction was freeze-dried to give compound 1 (N'-(4-hydroxybenzoyl)-4-methylbenzenesulfonohydrazide, 50 mg, 24.8% yield) as a white solid. $^1$HNMR (DMSO-$d_6$, 400 MHz): δ 10.38 (s, 1H), 10.09 (s, 1H), 9.76 (s, 1H), 7.69 (d, J=8.4 Hz, 1H), 7.56 (d, J=8.8 Hz, 1H), 7.32 (d, J=8.0 Hz, 1H), 6.76 (d, J=8.8 Hz, 1H), 2.35 (s, 3H).

LCMS; Mass Calcd.: 306.3; MS Found: 306.9.

Experimental Example 1-2. Preparation of Compound 2 (4-Amino-N'-(4-hydroxybenzoyl)benzenesulfonohydrazide)

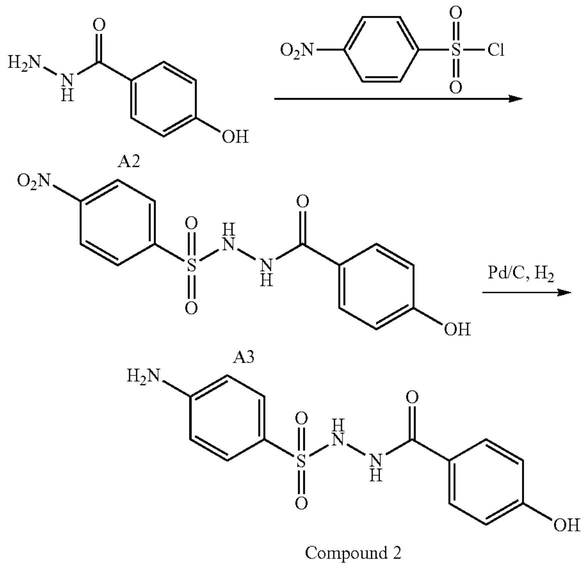

A2
A3
Compound 2

Step 1) Synthesis of A3

A mixture of A2 (4-hydroxybenzohydrazide, 0.3 g, 1.97 mmol, 1.0 eq) and 4-nitrobenzene-1-sulfonyl chloride (0.35 g, 1.57 mmol, 0.8 eq) in pyridine (5 mL) was stirred at 80° C. for 16 hrs. Then to the mixture was added 1N HCl till pH=3 and extracted with EA (20 mL×3). The combined organic layers were washed with brine, dried over $Na_2SO_4$ and concentrated to give crude A3 (N'-(4-hydroxybenzoyl)-4-nitrobenzenesulfonohydrazide, 370 mg) as a yellow solid. LCMS; Mass Calcd.: 337.1; MS Found: 337.6 [MS], 359.6 [MS+22].

Step 2) Synthesis of Compound 2

A mixture of A3 (N'-(4-hydroxybenzoyl)-4-nitrobenzenesulfonohydrazide, 150 mg, 0.45 mmol, 1.0 eq) and 5% Pd/C (200 mg, 50% in water) in EtOH (10 mL) was stirred at 10° C. for 4 hrs with a $H_2$ balloon. Then the mixture was filtered and the filtrate was concentrated to give crude product, which was purified by prep-HPLC. The collected fraction was concentrated to remove most of $CH_3CN$. The residual fraction was freeze-dried to give compound 2 (4-amino-N'-(4-hydroxybenzoyl)benzenesulfonohydrazide), 50 mg, yield 36.6%) as a white solid. $^1$HNMR (DMSO-$d_6$, 400 MHz): δ 10.31 (s, 1H), 10.06 (s, 1H), 9.13 (s, 1H), 7.56 (d, J=8.8 Hz, 2H), 7.41 (d, J=8.8 Hz, 2H), 6.76 (d, J=8.08 Hz, 2H), 6.50 (d, J=8.8 Hz, 2H), 5.95 (s, 2H).

LCMS; Mass Calcd.: 307.3; MS Found: 307.9.

Experimental Example 1-3. Preparation of Compound 3 (4-amino-N'-(4-hydroxybenzoyl)-3-morpholinobenzenesulfonohydrazide)

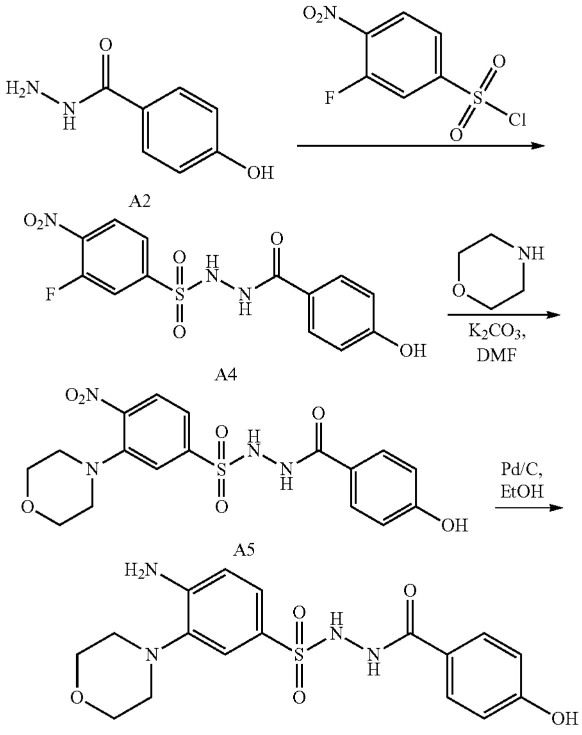

A2
A4
A5
Compound 3

Step 1) Synthesis of $A_4$

To a mixture of A2 (4-hydroxybenzohydrazide, 500 mg, 3.29 mmol, 1.0 eq) in pyridine (5 mL) was added 3-fluoro-4-nitrobenzene-1-sulfonyl chloride (790 mg, 3.29 mmol, 1.0 eq) in pyridine (3 mL) dropwise. Then the mixture was stirred at 25° C. for 3 hrs. The above solution was poured into water (30 mL). The mixture was extracted with EA (30 mL×3). The combined organic layers were washed with brine, dried over $Na_2SO_4$ and concentrated to give crude product, which was purified by flash column (DCM/MeOH=50/1~30/1) to give A4 (3-fluoro-N'-(4-hydroxybenzoyl)-4-nitrobenzenesulfonohydrazide, 500 mg, 42.8%) as a white solid. $^1$HNMR (DMSO-$d_6$, 400 MHz): δ 10.55 (s, 1H), 10.49 (s, 1H), 10.14 (s, 1H), 8.32 (t, J=8.0 Hz, 1H), 7.98 (d, J=10.4 Hz, 1H), 7.85 (d, J=8.8 Hz, 1H), 7.60 (d, J=8.8 Hz, 2H), 6.78 (d, J=8.4 Hz, 2H).

Step 2) Synthesis of $A_5$

To a mixture of A4 (3-fluoro-N'-(4-hydroxybenzoyl)-4-nitrobenzenesulfonohydrazide, 500 mg, 1.41 mmol, 1.0 eq) and morpholine (184 mg, 2.11 mmol, 1.5 eq) in DMF (10 mL) was added $K_2CO_3$ (486 mg, 3.52 mmol, 2.5 eq) at 25° C. Then the mixture was stirred at 25° C. for 16 hrs. The above solution was poured into water (30 mL). The mixture was extracted with EA (30 mL×3). The combined organic layers were washed with water (50 mL×3) and brine, dried over $Na_2SO_4$ and concentrated to give crude product, which was purified by flash column (DCM/MeOH=50/1~30/1) to give A5 (N'-(4-hydroxybenzoyl)-3-morpholino-4-nitrobenzenesulfonohydrazide, 180 mg, 30.3%) as a white solid. $^1$HNMR (DMSO-$d_6$, 400 MHz): δ 10.51 (s, 1H), 10.24 (s, 1H), 10.14 (s, 1H), 7.96 (d, J=8.4 Hz, 1H), 7.60-7.62 (m, 3H), 7.52 (d, J=8.4 Hz, 1H), 6.79 (d, J=8.4 Hz, 2H), 3.64 (t, J=4.8 Hz, 4H), 2.90-2.94 (m, 4H).

Step 3) Synthesis of Compound 3

To a mixture of A5 (N'-(4-hydroxybenzoyl)-3-morpholino-4-nitrobenzenesulfonohydrazide, 180 mg, 0.427 mmol, 1.0 eq) in EtOH (10 mL) was added Pd/C (200 mg) at 25° C. Then the mixture was stirred at 25° C. for 4 hrs under $H_2$ balloon. The above solution was filtered and the filtrate was concentrated and purified by prep-HPLC to give compound 3 (4-amino-N'-(4-hydroxybenzoyl)-3-morpholinobenzenesulfonohydrazide, 40 mg, 23.9%) as a white solid. (TLC: N/A)$^1$HNMR (DMSO-$d_6$, 400 MHz): δ 10.35 (d, J=3.6 Hz, 1H), 10.06 (s, 1H), 9.20 (d, J=4.0 Hz, 1H), 7.58 (d, J=8.4 Hz, 2H), 7.23-7.28 (m, 2H), 6.76 (d, J=8.8 Hz, 2H), 6.66 (d, J=8.4 Hz, 1H), 5.63 (s, 2H), 3.69 (t, J=4.4 Hz, 4H), 2.62 (t, J=4.4 Hz, 4H).

LCMS; Mass Calcd.: 392.4; MS Found: 393.

Experimental Example 1-4. Preparation of Compound 4 (N'-(4-hydroxybenzoyl)-2-oxoindoline-5-sulfonohydrazide)

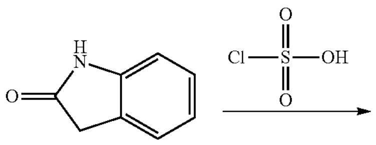
A6

-continued

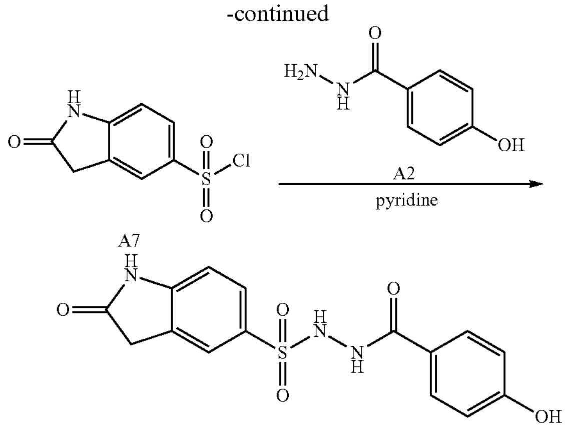

A7

Compound 4

Step 1) Synthesis of A7

A mixture of chlorosulfonic acid (0.88 g, 7.52 mmol, 1.0 eq) and A6 (indolin-2-one, 1.0 g, 7.52 mmol, 1.0 eq) was stirred at 25° C. for 1.5 hrs and then at 68° C. for 1 hr. The mixture was cooled and poured carefully into water. The formed precipitate was collected by filtration, washed with water and dried under vacuum to give A7 (2-oxoindoline-5-sulfonyl chloride, 0.7 g, crude) as a pink solid. $^1$HNMR (DMSO-$d_6$, 400 MHz): δ 10.47 (br s, 1H), 7.44-7.46 (m, 2H), 6.75 (d, J=8.8 Hz, 1H), 3.47 (s, 2H).

Step 2) Synthesis of Compound 4

A mixture of A2 (4-hydroxybenzohydrazide, 0.20 g, 1.32 mmol, 1.0 eq) and A7 (2-oxoindoline-5-sulfonyl chloride, 0.30 g, 1.32 mmol, 1.0 eq) in pyridine (10 mL) was stirred at 30° C. for 5 hrs. The mixture was poured into water. The formed precipitate was collected by filtration, washed with water and dried under vacuum. The solid was stirred in DCM at 30° C. for 30 min. The mixture was filtered and the filter cake was dried to give compound 4 (N'-(4-hydroxybenzoyl)-2-oxoindoline-5-sulfonohydrazide 50 mg, 11%) as a pink solid. $^1$HNMR (DMSO-$d_6$, 400 MHz): δ 10.79 (br s, 1H), 10.35 (br s, 1H), 10.11 (br s, 1H), 9.62 (br s, 1H), 7.63-7.66 (m, 2H), 7.57 (d, J=8.4 Hz, 2H), 6.88 (d, J=8.4 Hz, 1H), 6.77 (d, J=8.4 Hz, 2H), 3.51 (s, 2H).

LCMS; Mass Calcd.: 347.3; MS Found: 347.8.

Experimental Example 1-5. Preparation of Compound 5 (N'-(4-hydroxybenzoyl)indoline-5-sulfonohydrazide)

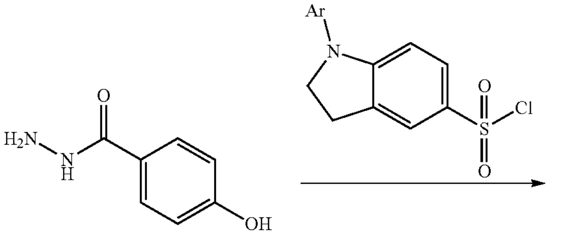

A2

-continued

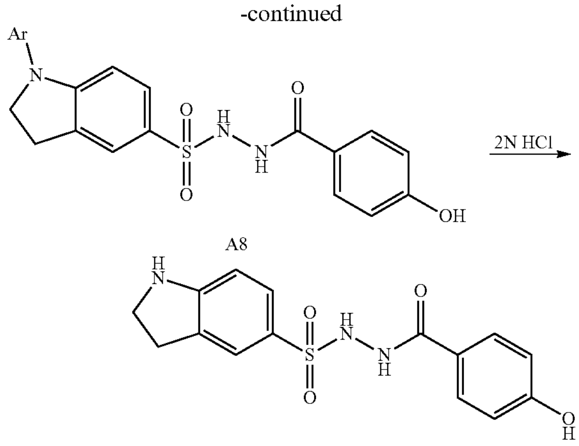

A8

Compound 5

Step 1) Synthesis of A8

A mixture of A2 (4-hydroxybenzohydrazide, 293 mg, 1.93 mmol, 1.0 eq) and 1-acetylindoline-5-sulfonyl chloride (500 mg, 1.93 mmol, 1.0 eq) in pyridine (10 mL) was stirred at 30° C. for 5 hrs. After completion, the reaction mixture was diluted with $H_2O$ (20 mL) and extracted with EA (20 mL×3). The combined organic layers were washed with brine, dried over $Na_2SO_4$ and concentrated to give A8 (1-acetyl-N'-(4-hydroxybenzoyl)indoline-5-sulfonohydrazide, 500 mg, crude) as a yellow solid.

Step 2) Synthesis of Compound 5

A mixture of A8 (1-acetyl-N'-(4-hydroxybenzoyl)indoline-5-sulfonohydrazide, 200 mg, 0.53 mmol, 1.0 eq) and 2N HCl (6 mL) in THF (10 mL) was stirred at 50° C. for 5 hrs. After completion, the reaction mixture was diluted with $H_2O$ (20 mL) and extracted with EA (20 mL×3). The combined organic layers were washed with brine, dried over $Na_2SO_4$ and concentrated. The crude product was purified by prep-HPLC and lyophilized to give compound 5 (N'-(4-hydroxybenzoyl)indoline-5-sulfonohydrazide, 50 mg, 28.2%) as a white solid.

1HNMR (DMSO-$d_6$, 400 MHz): δ 10.30 (br s, 1H), 10.05 (br s, 1H), 9.14 (br s, 1H), 7.58 (d, J=8.4 Hz, 2H), 7.33-7.36 (m, 2H), 6.77 (d, J=8.4 Hz, 2H), 6.37-6.40 (m, 2H), 3.51 (t, J=8.4 Hz, 2H), 2.90 (t, J=8.4 Hz, 2H).

LCMS; Mass Calcd.: 333.3; MS Found: 333.8.

Experimental Example 1-6. Preparation of Compound 6 (N'—([1,1'-biphenyl]-4-carbonyl)-4-aminobenzenesulfonohydrazide)

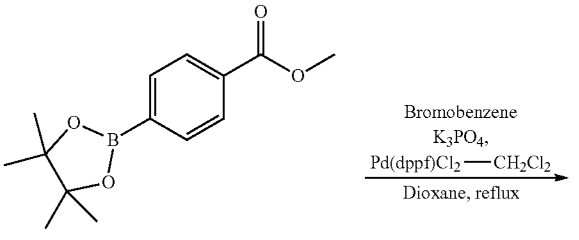

A9

-continued

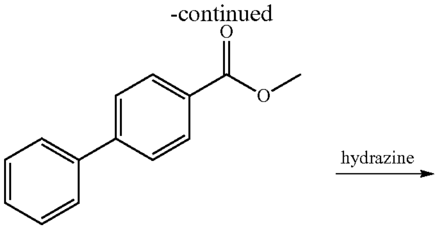

A10

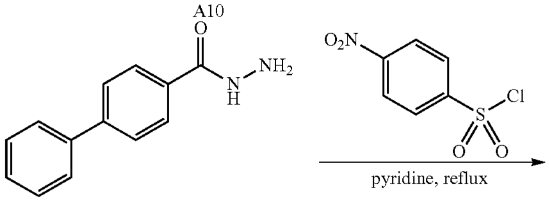

A11

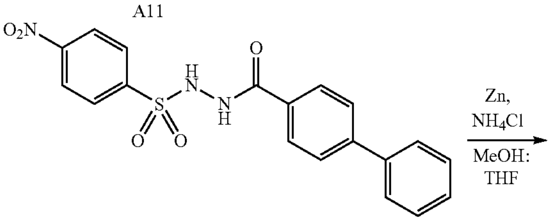

A12

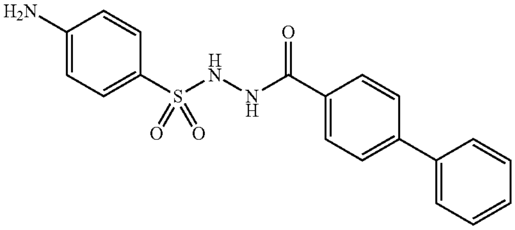

Compound 6

Step 1) Synthesis of A10

To a solution of bromobenzene (400 mg, 2.5 mmol) in Dioxane was added methyl 4-(4,4,5,5-tetramethyl-1,3,2-dioxaborolan-2-yl)benzoate (A9, 801 mg, 3.0 mmol), $K_3PO_4$ (541 mg, 7.5 mmol) and Pd(dppf) $Cl_2$—$CH_2Cl_2$ (208 mg, 0.25 mmol) at room temperature. The mixture was stirred at 100° C. for 12 hrs. After the reaction was completed, the reaction mixture was cooled. The reaction mixture was filtered through Celite and then extracted with ethyl acetate. The Organic layer was dried over anhydrous $MgSO_4$ and concentrated under reduced pressure. The residue was purified by flash column chromatography (Hex/EA=3/1) to give A10 (methyl [1,1'-biphenyl]-4-carboxylate, 160 mg, yield: 45%) as a white solid. 1H NMR (DMSO-$d_6$, 600 MHz) δ (ppm): 8.05-8.03 (m, 2H), 7.84-7.83 (m, 2H), 7.76-7.74 (m, 2H), 7.52-7.50 (m, 2H), 7.50-7.42 (m, 1H), 3.87 (s, 3H); LCMS Calcd m/z for $C_{14}H_{12}O_2$ $[M+H]^+$ 213.25 Found 213.

Step 2) Synthesis of A11

To a solution of A10 (methyl [1,1'-biphenyl]-4-carboxylate, 160 mg, 0.70 mmol) in Hydrazine monohydrate (8 mL) was stirred at 100° C. for 16 hrs. After the reaction was completed, the reaction mixture was cooled and then concentrated under reduced pressure then purified by flash column chromatography (DCM/MeOH=15/1) to give crude product, A11 ([1,1'-biphenyl]-4-carbohydrazide, 152 mg, theoretical yield: 100%) as a white solid. LCMS Calcd m/z for $C_{13}H_{12}N_2O$ $[M+H]^+$ 213.25 Found 213.

Step 3) Synthesis of A12

To a solution of A11 ([1,1'-biphenyl]-4-carbohydrazide, 152 mg, 0.70 mmol) in pyridine (5 mL) was added 4-nitrosulfonyl chloride (143 mg, 0.60 mmol). The mixture was refluxed for 12 hrs. After the reaction was completed, the resulting mixture was cooled and evaporated to remove Pyridine then purified by flash column chromatography (DCM/MeOH=15/1) to give crude product, A12 (N'—([1,1'-biphenyl]-4-carbonyl)-4-nitrobenzenesulfonohydrazide, 60 mg, yield: 21%) as a yellow solid. LCMS Calcd m/z for $C_{19}H_{15}N_3O_5S$ $[M+H]^+$ 398.41 Found 398.

Step 4) Synthesis of Compound 6

To a solution of A12 (N'—([1,1'-biphenyl]-4-carbonyl)-4-nitrobenzenesulfonohydrazide, 60 mg, 0.15 mmol) in THF:MeOH=3:1 (12 mL) was added Zn (99 mg, 1.5 mmol) and $NH_4Cl$ (81 mg, 1.5 mmol). The mixture was stirred at room temperature for 12 hrs. After the reaction was completed and then added ethyl acetate. The mixture was filtered through Celite. The filtrate was concentrated under reduced pressure. The residue was purified by flash column chromatography (DCM/MeOH=15/1) to give compound 6 (N'—([1,1'-biphenyl]-4-carbonyl)-4-aminobenzenesulfonohydrazide, 10 mg, yield: 20%) as a white solid. 1H NMR (DMSO-d6, 600 MHz) δ (ppm): δ 10.64 (br s, 1H), 9.32 (br s, 1H), 7.79-7.77 (m, 2H), 7.74-7.70 (m, 4H), 7.49 (t, 2H), 7.45-7.39 (m, 3H), 6.51 (d, J=6.0 Hz, 2H), 5.96 (s, 1H), 6.52 (d, J=5.0 Hz, 2H); LCMS Calcd m/z for $C_{19}H_{17}N_3O_3S$ $[M+H]^+$ 368.42 Found 368.

Experimental Example 1-7. Preparation of Compound 7 (N'—([1,1'-biphenyl]-3-carbonyl)-4-aminobenzenesulfonohydrazide)

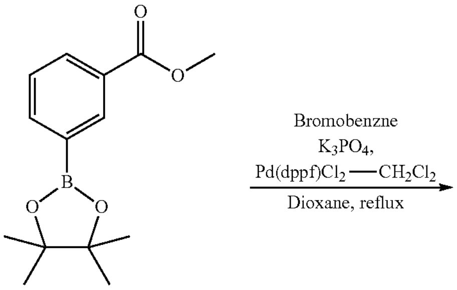

A13

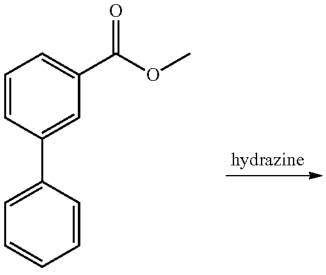

A14

-continued

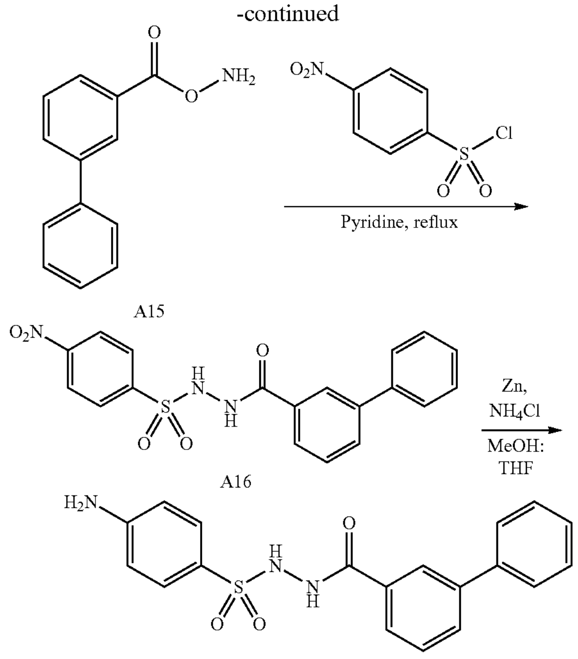

A15

A16

Compound 7

Step 1) Synthesis of A14

To a solution of bromobenzene (400 mg, 2.5 mmol) in Dioxane was added of methyl 3-(4,4,5,5-tetramethyl-1,3,2-dioxaborolan-2-yl)benzoate (A13, 801 mg, 3.0 mmol), $K_3PO_4$ (541 mg, 7.5 mmol) and Pd(dppf) $Cl_2$—$CH_2Cl_2$ (208 mg, 0.25 mmol) at room temperature. The mixture was stirred at 100° C. for 12 hrs. After the reaction was completed, the reaction mixture was cooled. The mixture was filterated through Celite and then extracted with ethyl acetate. The Organic layer was dried over anhydrous $MgSO_4$ and concentrated under reduced pressure. The residue was purified by flash column chromatography (Hex/EA=3/1) to give A14 (methyl [1,1'-biphenyl]-3-carboxylate, 160 mg, yield: 49%) as a white solid.

1H NMR (DMSO-$d_6$, 600 MHz) δ (ppm): 8.18 (t, J=1.8 Hz, 1H), 7.97-7.95 (m, 2H), 7.71-7.70 (m, 2H), 7.63 (t, J=7.7 Hz, 1H), 7.52-7.49 (m, 2H), 7.43-7.41 (m, 1H), 3.89 (s, 3H); LCMS Calcd m/z for $C_{14}H_{12}O_2$ $[M+H]^+$ 213.25 Found 213.

Step 2) Synthesis of A15

To a solution of A14 (methyl [1,1'-biphenyl]-3-carboxylate, 160 mg, 7.5 mmol) in Hydrazine monohydrate (8 mL) was stirred at 100° C. for 16 hrs. After the reaction was completed, the reaction mixture was cooled and then concentrated under reduced pressure then purified by flash column chromatography (DCM/MeOH=15/1) to give crude product A15 ([1,1'-biphenyl]-3-carbohydrazide, 200 mg, yield: 100%) as a yellow solid. LCMS Calcd m/z for $C_{13}H_{12}N_2O$ $[M+H]^+$ 213.25 Found 213.

Step 3) Synthesis of A16

To a solution of A15 ([1,1'-biphenyl]-3-carbohydrazide, 200 mg, 0.90 mmol) in Pyridine (7 mL) was added 4-Nitrosulfonyl chloride (2.5 mL). The mixture was refluxed for 12 hrs. After the reaction was completed, the resulting mixture was cooled and evaporated to remove Pyridine then purified by flash column chromatography (DCM/MeOH=15/1) to give crude product, A16 (N'—([1,1'-biphenyl]-3-carbonyl)-4-nitrobenzenesulfonohydrazide, 102 mg, yield: 53%) as an ivory solid. LCMS Calcd m/z for $C_{19}H_{15}N_3O_5S$ $[M+H]^+$ 398.41 Found 398.

Step 4) Synthesis of Compound 7

To a solution of A16 (N'—([1,1'-biphenyl]-3-carbonyl)-4-nitrobenzenesulfonohydrazide, 102 mg, 0.25 mmol) in THF:MeOH=3:1 (10 mL) was added Zn (168 mg, 2.5 mmol) and $NH_4Cl$ (137 mg, 2.5 mmol). The mixture was stirred at room temperature for 12 hrs. After the reaction was completed and then added ethyl acetate. The mixture was filterated through Celite. The filterate was concentrated under reduced pressure. The residue was purified by flash column chromatography (DCM/MeOH=15/1) to give compound 7 (N'—([1,1'-biphenyl]-3-carbonyl)-4-aminobenzenesulfonohydrazide, 14 m g, yield: 14%, purity: 96.8%) as a white solid.

1H NMR (DMSO-$d_6$, 600 MHz) δ (ppm): δ 10.71 (br s, 1H), 9.37 (br s, 1H), 7.97 (s, 1H), 7.83 (d, J=6.0 Hz, 1H), 7.72 (d, J=6.0 Hz, 2H), 7.65 (d, J=6.0 Hz, 1H), 7.54-7.49 (m, 3H), 7.45 (d, J=6.0 Hz, 2H), 7.42 (t, 1H), 6.52 (d, J=6.0 Hz, 2H), 5.97 (s, 2H); ESI-MS Calcd m/z for $C_{19}H_{17}N_3O_3S$ $[M+H]^+$ 368.42 Found 368.

Experimental Example 1-8. Preparation of Compound 8 (3-Amino-N'-(4-hydroxybenzoyl)benzenesulfonohydrazide)

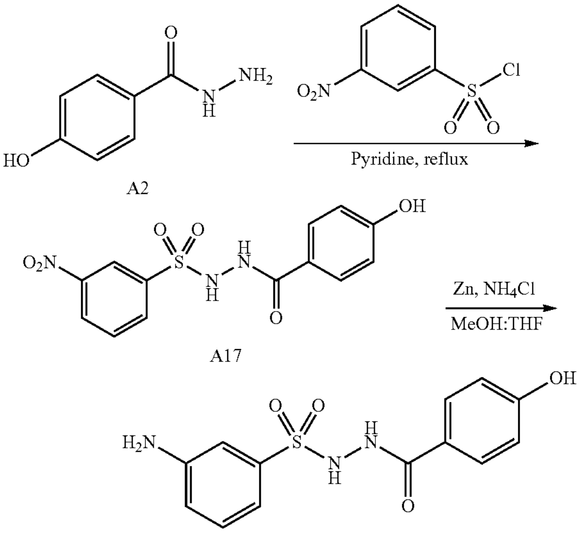

A2

A17

Compound 8

Step 1) Synthesis of A17

To a solution of A2 (200 mg, 0.90 mmol) in Pyridine (8 mL) was added 3-Nitrosulfonyl chloride (168 mg, 1.08 mmol). The mixture was refluxed for 12 hrs. After the reaction was completed, the resulting mixture was cooled and evaporated to remove Pyridine then purified by flash column chromatography (DCM/MeOH=15/1) to give crude product, A17 (N'-(4-hydroxybenzoyl)-3-nitrobenzenesulfonohydrazide, 129 mg, yield: 43%) as an ivory solid. LCMS Calcd m/z for $C_{13}H_{11}N_3O_6S$ [M+H]$^+$ 338.31 Found 338.

Step 2) Synthesis of Compound 8

To a solution of A17 (N'-(4-hydroxybenzoyl)-3-nitrobenzenesulfonohydrazide, 129 mg, 0.38 mmol) in THF: MeOH=3:1 (10 mL) was added Zn (250 mg, 3.8 mmol) and $NH_4Cl$ (204 mg, 3.8 mmol). The mixture was stirred at room temperature for 12 hrs. After the reaction was completed and then added ethyl acetate. The mixture was filtered through Celite. The filtrate was concentrated under reduced pressure. The residue was purified by flash column chromatography (DCM/MeOH=15/1) to give UTL1013(3-amino-N'-(4-hydroxybenzoyl)benzenesulfonohydrazide, 25 mg, yield: 21%, purity: 98.0%) as a white solid. 1H NMR (DMSO-$d_6$, 600 MHz) δ (ppm): δ 10.36 (br s, 1H), 10.06 (br s, 1H), 9.53 (br s, 1H), 7.59 (d, J=12 Hz, 2H), 7.11-7.08 (t, J=9.0 Hz, 1H), 7.02 (s, 1H) 6.90 (d, J=6.0 Hz, 1H), 6.77 (d, J=6.0 Hz, 1H), 6.71 (d, J=12 Hz, 1H), 5.49 (s, 2H); LCMS Calcd m/z for $C_{13}H_{13}N_3O_4S$ [M+H]$^+$ 308.32 Found 308.

Experimental Example 1-9. Preparation of Compound 9 (4-(1-Aminoethyl)-N'-(4-hydroxybenzoyl)benzenesulfonohydrazide)

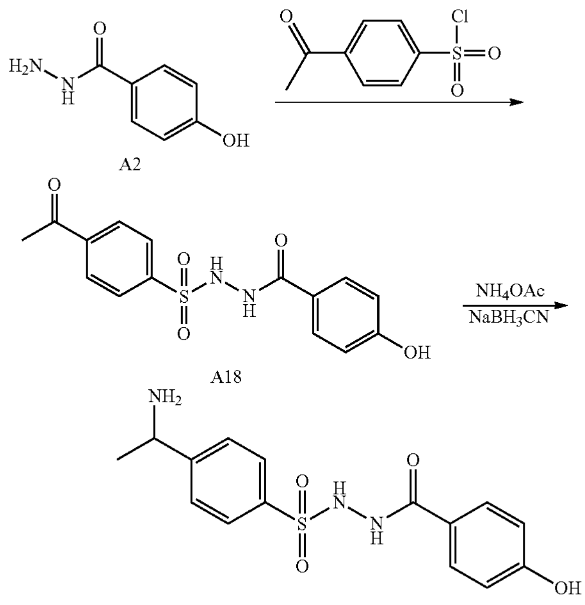

A2

A18

Compound 9

Step 1) Synthesis of A18

A mixture of A2 (4-hydroxybenzohydrazide, 500 mg, 3.29 mmol, 1.0 eq) and 4-acetylbenzene-1-sulfonyl chloride (717 mg, 3.29 mmol, 1.0 eq) in pyridine (5 mL) was stirred at 25° C. for 3 hrs. The mixture was cooled and poured carefully into water. The mixture was extracted with EA (50 mL×2). The combined organic layers were washed with brine, dried over anhydrous $Na_2SO_4$ and concentrated to afford A18 (4-acetyl-N'-(4-hydroxybenzoyl)benzenesulfonohydrazide, 0.5 g, crude) as a brown solid. LCMS Calcd m/z for $C_{15}H_{14}N_2O_5S$ [M+H]$^+$ 335.3 Found 335.

Step 2) Synthesis of Compound 9

A mixture of A18 (4-acetyl-N'-(4-hydroxybenzoyl)benzenesulfonohydrazide, 200 mg, 0.60 mmol, 1.0 eq), $NH_4OAc$ (461 mg, 5.98 mmol, 10 eq) and sodium cyanoborohydride (188 mg, 2.99 mmol, 5 eq) in MeOH (5 mL) was stirred at 60° C. for 16 hrs. The mixture was concentrated and purified by prep-HPLC and lyophilized to afford compound 9 (4-(1-Aminoethyl)-N'-(4-hydroxybenzoyl)benzenesulfonohydrazide, 55 mg, 24%) as a white solid. $^1$HNMR (DMSO-$d_6$, 400 MHz): δ 10.37 (br s, 2H), 8.28 (s, 1H), 7.80 (d, J=8.0 Hz, 2H), 7.57 (dd, J=11.2, 8.8 Hz, 2H), 6.77 (d, J=8.4 Hz, 2H), 4.22 (q, J=6.8 Hz, 1H), 1.33 (d, J=6.4 Hz, 3H).

LCMS; Mass Calcd.: 335.3 ($C_{15}H_{17}N_3O_4S$); MS Found: 336.

Experimental Example 1-10. Preparation of Compound 10 (3,5-Diamino-N'-(4-hydroxybenzoyl)benzenesulfonohydrazide)

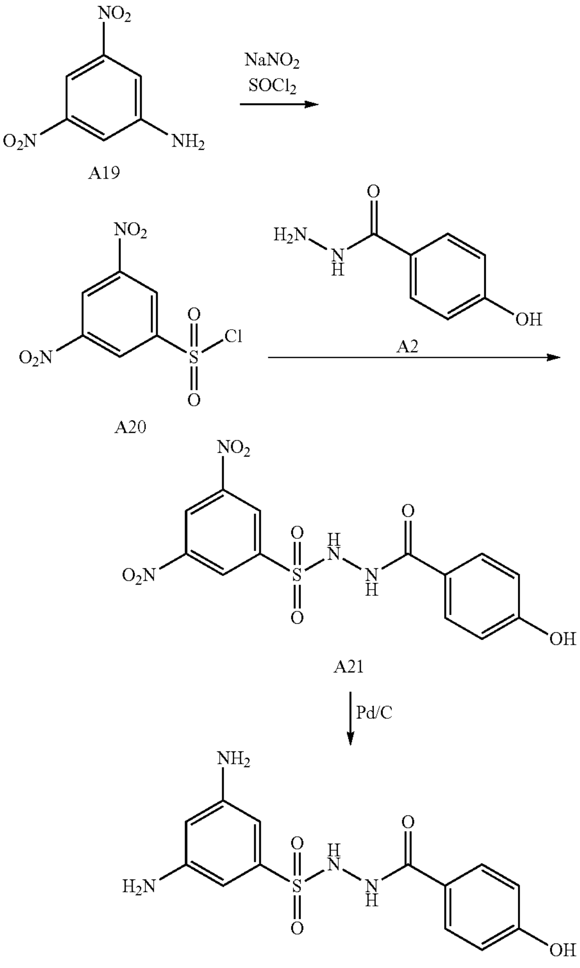

A19

A20

A21

Compound 10

Step 1) Synthesis of A20

To a mixture of 3,5-dinitroaniline (A19, 500 mg, 2.73 mmol, 1.0 eq) in conc. HCl (10 mL) was added $NaNO_2$ (226 mg, 3.28 mmol, 1.2 eq) in $H_2O$ (2 mL) at 0° C. The mixture was stirred at 0° C. for 0.5 hr. To a mixture of CuCl (27 mg, 0.27 mmol, 0.1 eq) in $H_2O$ (10 mL) was added $SOCl_2$ (1.30 g, 10.9 mmol, 4.0 eq) at 0° C. Then the diazo salt solution was added dropwise at 0° C. The mixture was stirred at 0° C. for 3 hrs and then poured into water. The formed precipitate was collected by filtration and dried under vacuum to give A20 (3,5-dinitrobenzenesulfonyl chloride, 0.5 g, crude) as a yellow solid.

Step 2) Synthesis of A21

A mixture of A20 (3,5-dinitrobenzenesulfonyl chloride, 175 mg, 0.66 mmol, 1.0 eq) and A2 (4-hydroxybenzohydrazide, 100 mg, 0.66 mmol, 1.0 eq) in pyridine (5 mL) was stirred at 60° C. for 16 hrs. The mixture was cooled and poured carefully into water. The mixture was extracted with EA (50 mL×2). The combined organic layers were washed with brine, dried over anhydrous $Na_2SO_4$ and concentrated to afford A21 (N'-(4-hydroxybenzoyl)-3,5-dinitrobenzenesulfonohydrazide, 0.1 g, crude) as a pink solid.

Step 3) Synthesis of Compound 10 (3,5-Diamino-N'-(4-hydroxybenzoyl)benzenesulfonohydrazide)

A mixture of A21 (N'-(4-hydroxybenzoyl)-3,5-dinitrobenzenesulfonohydrazide, 0.1 g, 0.26 mmol, 1.0 eq) and 10% Pd/C (0.1 g) in EtOH (5 mL) was stirred at r.t for 3 hrs under $H_2$ balloon. The reaction mixture was filtered, and the filter cake was washed with EA (50 mL×2). The combined filtrate was concentrated to give crude product, which was stirred in MeOH (5 mL) for 10 min. The mixture was filtered and the filter cake was dried in vacuo to afford compound 10 (3,5-diamino-N'-(4-hydroxybenzoyl)benzenesulfonohydrazide, 27 mg, 32%) as a yellow solid. $^1$HNMR (DMSO-$d_6$, 400 MHz): δ 10.20 (br s, 1H), 10.04 (br s, 1H), 9.19 (br s, 1H), 7.63 (d, J=8.8 Hz, 2H), 7.78 (d, J=8.4 Hz, 2H), 6.26 (d, J=1.6 Hz, 2H), 5.94 (s, 1H), 5.10 (s, 4H).

LCMS; Mass Calcd.: 322.3 ($C_{13}H_{14}N_4O_4S$); MS Found: 323 [MS+1].

Experimental Example 1-11. Preparation of Compound 11 (N'-(4-hydroxybenzoyl)-4-((2-hydroxyethyl)amino)benzenesulfonohydrazide)

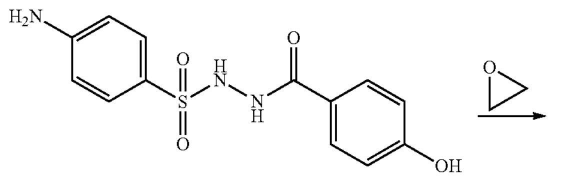

Compound 2

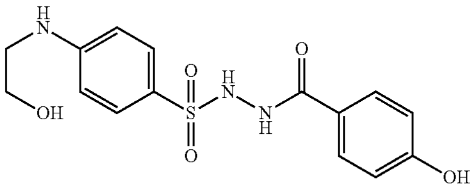

Compound 11

A mixture of compound 2 (4-amino-N'-(4-hydroxybenzoyl)benzenesulfonohydrazide, 500 mg, 1.63 mmol, 1.0 eq) and oxirane (72 mg, 1.63 mmol, 1.0 eq) in AcOH/$H_2O$=1:1 (4 mL) was stirred at 25° C. for 4 hrs. Then to the mixture was added $NaHCO_3$ till pH=8 and extracted with EA (50 mL×3). The combined organic layers were washed with brine, dried over $Na_2SO_4$ and concentrated to give crude product, which was purified by prep-TLC to afford compound 11 (N'-(4-hydroxybenzoyl)-4-((2-hydroxyethyl)amino)benzenesulfonohydrazide, 50 mg, yield 8.8%) as a white solid. $^1$HNMR (DMSO-$d_6$, 400 MHz): δ 7.56 (d, J=8.4 Hz, 2H), 7.46 (d, J=8.8 Hz, 2H), 6.73 (d, J=8.4 Hz, 2H), 6.56 (d, J=8.8 Hz, 2H), 6.45 (t, J=5.2 Hz, 1H), 3.53 (t, J=6.0 Hz, 2H), 3.12 (q, J=6.0 Hz, 2H).

LCMS; Mass Calcd.: 351.3; MS Found: 351.8 [MS+1].

Experimental Example 1-12. Preparation of Compound 12 (4-amino-N-(2-(4-hydroxyphenyl)-2-oxoethyl)benzenesulfonamide)

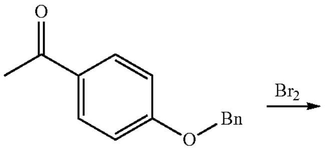

A22

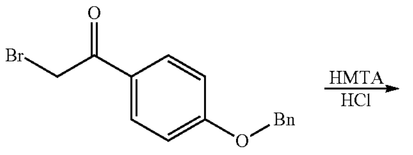

A23

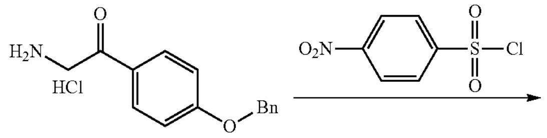

A24

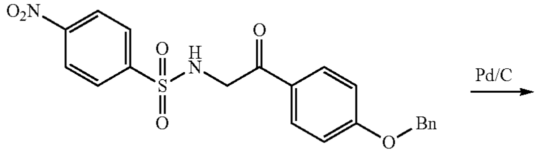

A25

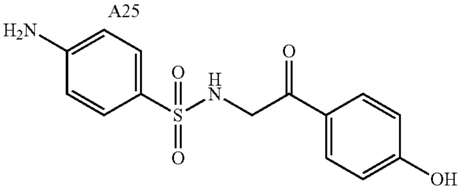

Compound 12

Step 1) Synthesis of A23

To a mixture of A22 (1-(4-(benzyloxy)phenyl)ethan-1-one, 4.0 g, 17.7 mmol, 1.0 eq) in EtOH (40 mL) was added $Br_2$ (2.83 g, 17.7 mmol, 1.0 eq) at 5° C. The mixture was stirred at 30° C. for 30 min. The mixture was poured into PE and stirred for 30 min. The mixture was filtered, and the filter cake was dried to give A23 (1-(4-(benzyloxy)phenyl)-2-bromoethan-1-one, 2.5 g, 46.3%) as a white solid.

Step 2) Synthesis of A24

A mixture of A23 (1-(4-(benzyloxy)phenyl)-2-bromoethan-1-one, 2.0 g, 6.55 mmol, 1.0 eq) and HMTA (1.38 g, 9.83 mmol, 1.5 eq) in DCM (20 mL) was stirred at 10° C. for 2 hrs. Then the mixture was filtered and the filter cake was dissolved in EtOH (15 mL) and conc. HCl (5 mL). The mixture was stirred at 85° C. for 2 hrs. The mixture was filtered and the filter cake was dried to give A24 (2-amino-1-(4-(benzyloxy)phenyl)ethan-1-one hydrochloride, 2.0 g, crude) as a white solid.

1HNMR ($CD_3OD$, 400 MHz): δ 8.03 (d, J=8.8 Hz, 2H), 7.47 (d, J=7.2 Hz, 2H), 7.34-7.42 (m, 3H), 7.17 (d, J=8.8 Hz, 2H), 5.23 (s, 2H), 4.55 (s, 2H).

Step 3) Synthesis of A25

A mixture of A24 (2-amino-1-(4-(benzyloxy)phenyl)ethan-1-one hydrochloride, 2.00 g, 7.20 mmol, 1.0 eq), 4-nitrobenzene-1-sulfonyl chloride (1.60 g, 7.20 mmol, 1.0 eq) and TEA (2.19 g, 21.6 mmol, 3.0 eq) in DCM (20 mL) was stirred at 20° C. for 1 hr. The mixture was poured into water and extracted with DCM. The organic layer was washed with water and brine, dried over $Na_2SO_4$ and concentrated to give crude product, which was stirred in PE for 30 min. The mixture was filtered and the filter cake was to give A25 (N'-(2-(4-(benzyloxy)phenyl)-2-oxoethyl)-4-nitrobenzenesulfonamide, 1.0 g, 35.8% for 2 steps) as a white solid.

1HNMR ($CD_3Cl$, 400 MHz): δ 8.36 (d, J=8.8 Hz, 2H), 8.10 (d, J=8.4 Hz, 2H), 7.84 (d, J=8.8 Hz, 2H), 7.37-7.43 (m, 5H), 7.03 (d, J=8.4 Hz, 2H), 5.86 (t, J=4.0 Hz, 1H), 5.16 (s, 2H), 4.49 (d, J=4.0 Hz, 2H).

Step 4) Synthesis of Compound 12

A mixture of A25 (N'-(2-(4-(benzyloxy)phenyl)-2-oxoethyl)-4-nitrobenzenesulfonamide, 200 mg, 0.47 mmol, 1.0 eq) and Pd/C (150 mg, 50% in water) in EtOH (10 mL) was stirred at 25° C. for 4 hrs under $H_2$ balloon. Then the mixture was filtered and the mixture was concentrated and purified by prep-HPLC and lyophilized to afford compound 12 (4-amino-N'-(2-(4-hydroxyphenyl)-2-oxoethyl)benzenesulfonamide, 69 mg, yield 48.0%) as a white solid. $^1$HNMR (DMSO-$d_6$, 400 MHz): δ 10.43 (s, 1H), 7.79 (d, J=8.4 Hz, 2H), 7.46 (d, J=8.4 Hz, 2H), 7.32 (t, J=5.6 Hz, 1H), 6.83 (d, J=8.4 Hz, 1H), 6.58 (d, J=8.8 Hz, 2H), 5.91 (s, 2H), 4.19 (d, J=5.6 Hz, 2H).

LCMS; Mass Calcd.: 306.3; MS Found: 307 [MS+1].

Experimental Example 1-13. Preparation of Compound 13 (N'-(4-hydroxybenzoyl)-4-methoxybenzenesulfonohydrazide)

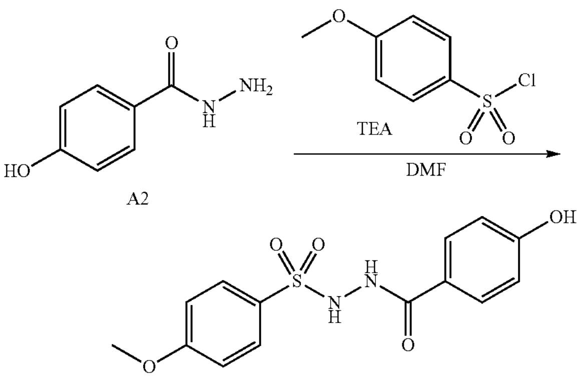

A2

Compound 13

To a solution of A2 (4-hydroxybenzohydrazide, 100 mg, 0.66 mmol) in DMF (6 mL) was added triethylamine (0.11 mL, 0.76 mmol) and 4-methoxybenzenesulfonyl chloride (124 mg, 0.60 mmol). The mixture was room temperature for 12 hrs. After the reaction was completed, the reaction mixture was evaporated and extracted with ethyl acetate. The organic layer was washed with brine, dried over anhydrous $MgSO_4$ and concentrated under reduced pressure. The residue was purified by flash column chromatography (DCM/MeOH=5/1) to give compound 13 (N'-(4-hydroxybenzoyl)-4-methoxybenzenesulfonohydrazide, 25 mg, yield: 12%, purity: 96.9%) as a white solid. 1H NMR (DMSO-$d_6$, 600 MHz) δ (ppm): δ 10.37 (br s, 1H), 10.07 (br s, 1H), 9.64 (br s, 1H), 7.73 (d, J=12 Hz, 2H), 7.57 (d, J=6.0 Hz, 2H), 7.03 (d, J=6.0 Hz, 2H), 6.76 (d, J=6.0 Hz, 2H), 3.80 (s, 3H); LCMS Calcd m/z for $C_{14}H_{14}N_2O_5S$ $[M+H]^+$ 323.3 Found 323.

Experimental Example 1-14. Preparation of Compound 14 (4-((2-(4-hydroxybenzoyl)hydrazinyl)sulfonyl)benzimidamide

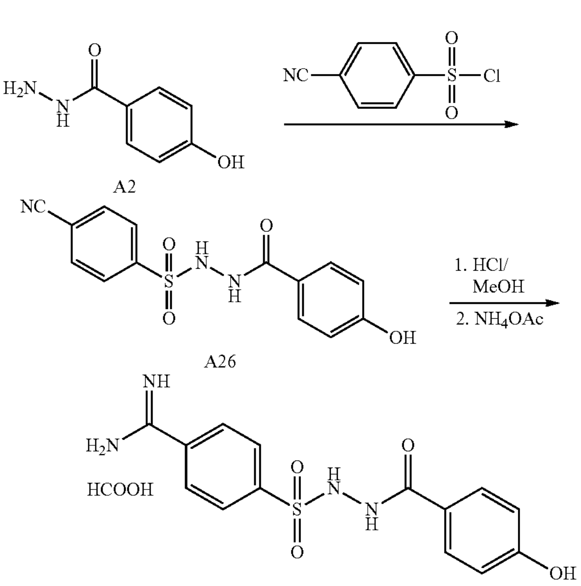

A2

A26

Compound 14

Step 1) Synthesis of A26

To a mixture of A2 (4-hydroxybenzohydrazide, 1.00 g, 6.57 mmol, 1.0 eq) in pyridine (10 mL) was added 4-cyanobenzene-1-sulfonyl chloride (1.33 g, 6.57 mmol, 1.0 eq) in pyridine (3 mL) dropwise. Then the mixture was stirred at 25° C. for 3 hrs. The above solution was poured into water (50 mL). The mixture was extracted with EA (50 mL×3). The combined organic layers were washed with brine, dried over $Na_2SO_4$ and concentrated to give crude product, which was purified by flash column (PE/EA=1/1) to give A26 (4-cyano-N'-(4-hydroxybenzoyl)benzenesulfonohydrazide, 1.40 g, 67.1%) as a white solid. $^1$HNMR (DMSO-$d_6$, 400 MHz): δ 10.49 (s, 1H), 10.27 (s, 1H), 10.14 (s, 1H), 8.02-8.04 (m, 2H), 7.97-7.99 (m, 2H), 7.57 (d, J=8.4 Hz, 2H), 7.78 (d, J=8.8 Hz, 2H).

Step 2) Synthesis of Compound 14

A mixture of A26 (4-cyano-N'-(4-hydroxybenzoyl)benzenesulfonohydrazide, 200 mg, 0.63 mmol, 1.0 eq) in HCl/

EtOH (5 mL, 6 mol/L) was stirred at 25° C. for 3 hrs. The above solution was concentrated and added to MeOH. The mixture was concentrated again. The residue was added to MeOH (10 mL) and then $NH_4OAc$ (485 mg, 6.30 mmol, 10 eq). The mixture was stirred at 25° C. for 16 hrs. The mixture was concentrated and purified by prep-HPLC and lyophilized to give compound 14 (4-((2-(4-hydroxybenzoyl)hydrazinyl)sulfonyl)benzimidamide, 26 mg, 10.8%) as a white solid. $^1$HNMR (DMSO-$d_6$, 400 MHz): δ 8.43 (s, 1H), 8.00 (d, J=8.0 Hz, 2H), 7.92 (d, J=8.4 Hz, 2H), 7.59 (d, J=8.8 Hz, 2H), 6.77 (d, J=8.8 Hz, 2H).

LCMS; Mass Calcd.: 334; MS Found: 334.8 [MS+1].

Experimental Example 1-15. Preparation of Compound 15 (4-((2-(4-hydroxybenzoyl)hydrazinyl)sulfonyl)benzamide)

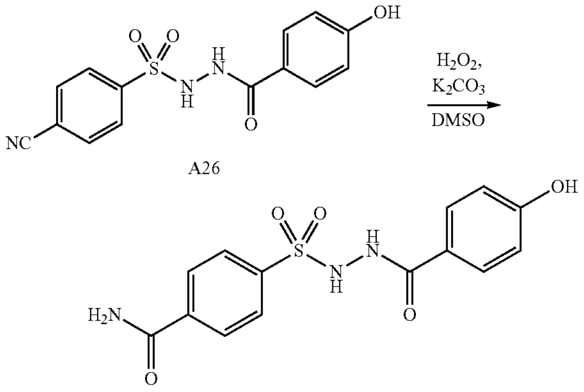

A26

Compound 15

To a cooled (0° C.) solution of A26 (4-cyano-N'-(4-hydroxybenzoyl)benzenesulfonohydrazide, 210 mg, 0.66 mmol) in DMSO was added hydrogen peroxide, 35% w/w aq. Soln., (0.42 mL, 4.8 mmol) and potassium carbonate (30 mg, 0.20 mmol). The reaction was allowed to warm to room temperature and stirred for 12 hrs. After the reaction was completed, the reaction mixture was evaporated and extracted with ethyl acetate. The organic layer was washed with brine, dried over anhydrous $MgSO_4$ and concentrated under reduced pressure. The residue was purified by flash column chromatography (DCM/MeOH=5/1) to give compound 15 (4-((2-(4-hydroxybenzoyl)hydrazinyl)sulfonyl)benzamide, 20 mg, yield: 10%, purity: 96.5%) as a white solid. 1H NMR (DMSO-$d_6$, 600 MHz) δ (ppm): δ 10.44 (br s, 1H), 10.10 (br s, 1H), 10.03 (br s, 1H), 8.15 (br s, 1H), 7.96 (d, J=6.0 Hz, 2H), 7.87 (d, J=10 Hz, 2H), 7.59 (br s, 1H), 7.57 (d, J=6.0 Hz, 2H), 6.76 (d, J=6.0 Hz, 2H); LCMS Calcd m/z for $C_{14}H_{13}N_3O_5S$ $[M+H]^+$ 336.33 Found 336.

Experimental Example 1-16. Preparation of Compound 16 (N'-(((4-aminophenyl)sulfonyl)methyl)-4-hydroxybenzamide)

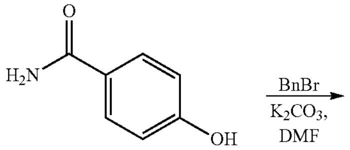

A27

-continued

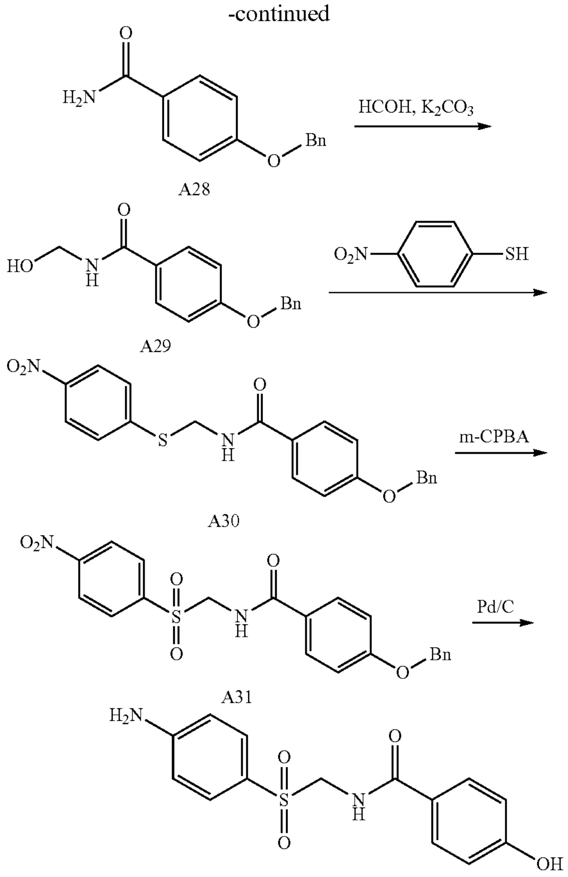

A28

A29

A30

A31

Compound 16

Step 1) Synthesis of A28

To a mixture of A27 (4-hydroxybenzamide, 4.0 g, 29.2 mmol, 1.0 eq) in DMF (40 mL) was added $K_2CO_3$ (6.05 g, 43.8 mmol, 1.5 eq) and BnBr (4.99 g, 29.2 mmol, 1.0 eq). The mixture was stirred at 60° C. for 16 hrs. The mixture was poured into water and extracted with EA. The organic layer was washed with water and brine, dried over $Na_2SO_4$ and concentrated to give A28 (4-(benzyloxy)benzamide, 6.0 g, 90.5%) as a white solid.

Step 2) Synthesis of A29

A mixture of A28 (4-(benzyloxy)benzamide, 4.0 g, 17.6 mmol, 1.0 eq), $K_2CO_3$ (0.24 g, 1.76 mmol, 0.1 eq) and HCOH (1.43 g, 17.6 mmol, 37% in water, 1.0 eq) in THF/$H_2O$ (40 mL, v/v=1/1) was stirred at 65° C. for 16 hrs. Then the mixture was concentrated and filtered. The filter cake was dried to give A29 (4-(benzyloxy)-N-(hydroxymethyl)benzamide, 4.0 g, crude) as a white solid.

Step 3) Synthesis of A30

A mixture of A29 (4-(benzyloxy)-N-(hydroxymethyl)benzamide, 4.00 g, 15.6 mmol, 1.0 eq) and 4-nitrobenzenethiol (2.41 g, 15.6 mmol, 1.0 eq) in TFA (20 mL) was stirred at 20° C. for 1 hr. The mixture was concentrated and added into water and adjusted pH=8 with aq. $NaHCO_3$. The mixture was extracted with EA. The organic layer was washed with brine, dried over $Na_2SO_4$ and concentrated to give A30 (4-(benzyloxy)-N-(((4-nitrophenyl)thio)methyl) benzamide, 2.0 g, 32.6% for 2 steps) as a white solid.

Step 4) Synthesis of A31

A mixture of A30 (4-(benzyloxy)-N-(((4-nitrophenyl) thio)methyl)benzamide, 500 mg, 1.27 mmol, 1.0 eq) and m-CPBA (656 g, 3.80 mmol, 3.0 eq) in DCM (20 mL) was stirred at 20° C. for 16 hrs. The mixture was poured into aq. $Na_2O_3S_2$ and extracted. The organic layer was washed with aq. $NaHCO_3$ and brine, dried over $Na_2SO_4$ and concentrated to give A31 (4-(benzyloxy)-N-(((4-nitrophenyl)sulfonyl) methyl)benzamide, 300 mg, crude) as a white solid. $^1$HNMR (DMSO-$d_6$, 400 MHz): δ 9.39 (t, J=6.4 Hz, 1H), 8.42 (d, J=8.8 Hz, 2H), 8.14 (d, J=8.8 Hz, 2H), 7.73 (d, J=8.8 Hz, 2H), 7.34-7.46 (m, 5H), 7.08 (d, J=8.8 Hz, 2H), 5.17 (s, 2H), 5.00 (d, J=6.4 Hz, 2H).

Step 5) Synthesis of Compound 16

A mixture of A31 (4-(benzyloxy)-N-(((4-nitrophenyl) sulfonyl)methyl)benzamide, 300 mg, 0.47 mmol, 1.0 eq) and Pd/C (150 mg, 50% in water) in EtOH (10 mL) was stirred at 25° C. for 2 hrs under $H_2$ balloon. Then the mixture was filtered and the mixture was concentrated and purified by prep-HPLC and lyophilized to afford compound 16 (N'-(((4-aminophenyl)sulfonyl)methyl)-4-hydroxybenzamide, 35 mg, yield 9.0% for 2 steps) as a white solid. $^1$HNMR (DMSO-$d_6$, 400 MHz): δ 10.15 (br s, 1H), 9.06 (t, J=6.4 Hz, 1H), 7.65 (d, J=8.8 Hz, 2H), 7.40 (d, J=8.8 Hz, 2H), 6.79 (d, J=8.8 Hz, 2H), 6.58 (d, J=8.8 Hz, 2H), 6.12 (s, 2H), 4.65 (d, J=6.4 Hz, 2H).

LCMS; Mass Calcd.: 306; MS Found: 307 [MS+1].

Experimental Example 1-17. Preparation of Compound 17 (6-amino-N'-(4-hydroxybenzoyl)-[1,1'-biphenyl]-3-sulfonohydrazide)

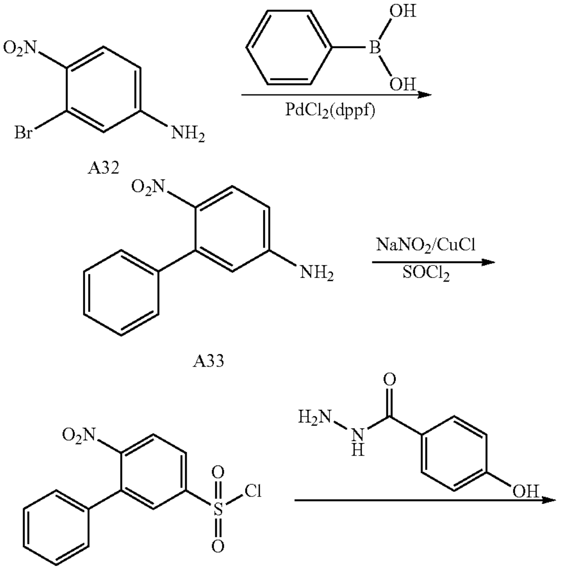

A32

A33

A34

-continued

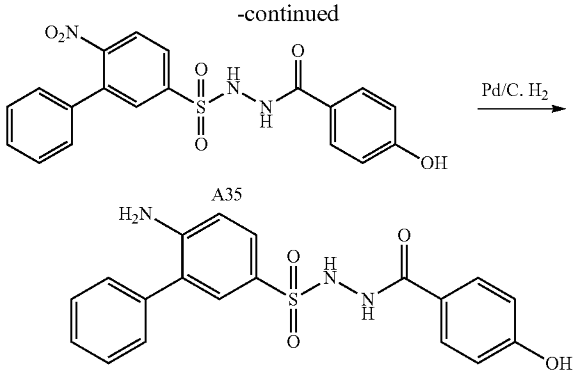

A35

Compound 17

Step 1) Synthesis of A33

A mixture of A32 (3-bromo-4-nitroaniline, 1 g, 4.61 mmol, 1.0 eq), phenylboronic acid (0.56 g, 4.61 mmol, 1.0 eq), Pd(dppf)$Cl_2$ (337 mg, 0.09 mmol, 0.1 eq) and AcOK (1.14 g, 13.8 mmol, 3.0 eq) in toluene (10 mL) was stirred for 16 hrs at 90° C. under N2. The mixture was poured into water (30 mL) and extracted with EA (30 mL×2). The combined organic layers were washed with brine, dried over $Na_2SO_4$ and concentrated. The crude product was purified by flash column (PE/EA=30/1~10/1) to afford A33 (6-nitro-[1,1'-biphenyl]-3-amine, 1 g, crude) as a yellow solid.

Step 2) Synthesis of A34

To a mixture of A33 (6-nitro-[1,1'-biphenyl]-3-amine, 500 mg, 2.33 mmol, 1.0 eq) in AcOH (10 mL) and conc. HCl (5 mL) was added dropwise $NaNO_2$ (193 mg, 2.8 mmol, 1.2 eq) in $H_2O$ (2 mL) at 0° C. The mixture was stirred at 0° C. for 0.5 hr. To a mixture of CuCl (31.3 mg, 0.23 mmol, 0.1 eq) in $H_2O$ (10 mL) was added $SOCl_2$ (1.39 g, 11.6 mmol, 5.0 eq) at 0° C. Then the diazo salt solution was added dropwise at 0° C. The mixture was stirred at 0° C. for 3 hrs and then poured into water. The formed precipitate was collected by filtration and dried under vacuum to give A34 (6-nitro-[1, 1'-biphenyl]-3-sulfonyl chloride, 400 mg, 57.6%) as a yellow solid. $^1$HNMR (DMSO-$d_6$, 400 MHz): δ 7.98 (d, J=8.4 Hz, 1H), 7.78-7.80 (m, 1H), 7.64 (d, J=1.2 Hz, 1H), 7.44-7.50 (m, 3H), 7.32-7.34 (m, 2H).

Step 3) Synthesis of A35

A mixture of A34 (6-nitro-[1,1'-biphenyl]-3-sulfonyl chloride, 200 mg, 0.67 mmol, 1.0 eq) and 4-hydroxybenzohydrazide (122 mg, 0.81 mmol, 1.2 eq) in pyridine (5 mL) was stirred at 30° C. for 0.5 hr. The mixture was poured carefully into water. The mixture was extracted with EA (50 mL×2). The combined organic layers were washed with brine, dried over anhydrous $Na_2SO_4$ and concentrated to afford A35 (N'-(4-hydroxybenzoyl)-6-nitro-[1,1'-biphenyl]-3-sulfonohydrazide, 200 mg, crude) as a brown solid.

Step 4) Synthesis of Compound 17

A mixture of A35 (N'-(4-hydroxybenzoyl)-6-nitro-[1,1'-biphenyl]-3-sulfonohydrazide, 200 mg, 0.48 mmol, 1.0 eq) and 10% Pd/C (200 mg) in EtOH (10 mL) was stirred at 30° C. for 3 hrs under $H_2$ balloon. The reaction mixture was filtered and the filter cake was washed with EA (50 mL×2).

The combined filtrate was concentrated to give crude product, which was purified by prep-HPLC and lyophilized to afford compound 17 (6-amino-N'-(4-hydroxybenzoyl)-[1,1'-biphenyl]-3-sulfonohydrazide, 45 mg, 17.5% for 2 steps) as a white solid. $^1$HNMR (DMSO-$d_6$, 400 MHz): δ 10.39 (s, 1H), 10.09 (s, 1H), 9.32 (s, 1H), 7.61 (d, J=8.8 Hz, 2H), 7.32-7.59 (m, 5H), 7.23 (d, J=6.4 Hz, 2H), 6.73-6.79 (m, 3H), 5.64 (s, 2H).

LCMS; Mass Calcd.: 383; MS Found: 384 [MS+1].

Experimental Example 1-18. Preparation of Compound 18 (4-(2-((4-aminophenyl)sulfonyl)hydrazine-1-carbonyl)benzamide)

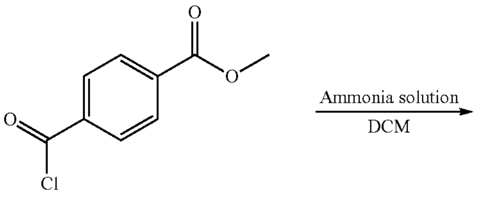

A36

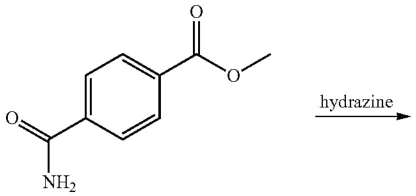

A37

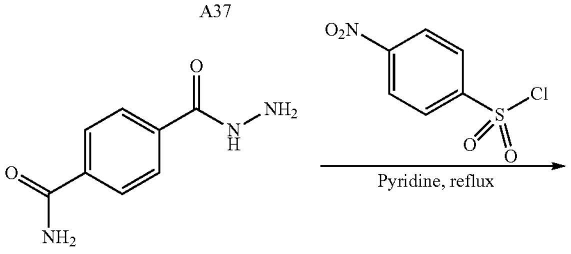

A38

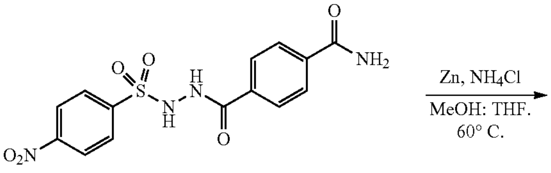

A39

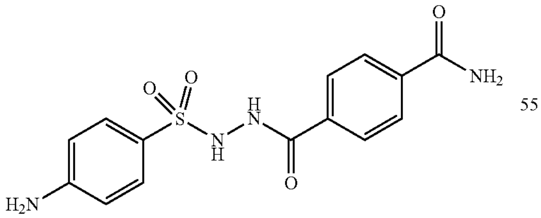

Compound 18

Step 1) Synthesis of A37

To a cooled (0° C.) solution of methyl 4-(chlorocarbonyl) benzoate (A36, 1.5 g, 7.5 mmol) in DCM was added ammonia solution (25~30%) (1.8 mL, 15 mmol). The reaction was allowed to warm to room temperature and stirred for 4 hrs. After the reaction was completed, the reaction mixture was evaporated and then added water. The formed precipitate was collected by filtration. The filter cake washed with water and dried to give A37 (methyl 4-carbamoylbenzoate, 1.0 g, 74%) as a white solid. LCMS Calcd m/z for $C_9H_9NO_3$ $[M+H]^+$ 152.17 Found 152.

Step 2) Synthesis of A38

The solution of A37 (methyl 4-carbamoylbenzoate, 1 g, 6.6 mmol) and Hydrazine monohydrate (10 mL) in MeOH (10 mL) was stirred at 80° C. for 16 hrs. The solvent was concentrated under reduced pressure to give crude product, which was purified by flash column (DCM/MeOH=10/1) to give A38 (4-(hydrazinecarbonyl)benzamide, 600 mg, yield: 60%) as a white solid. 1H NMR (DMSO-$d_6$, 600 MHz) δ (ppm): δ 9.87 (s, 1H), 8.06 (s, 1H), 7.92-7.91 (m, 2H), 7.87-7.86 (m, 2H), 7.48 (s, 1H), 4.55 (brs, 2H).

Step 3) Synthesis of A39

To a solution of A38 (4-(hydrazinecarbonyl)benzamide, 600 mg, 3.3 mmol) in DMF (7 mL) was added TEA (0.55 mL, 3.9 mmol) and 4-methoxybenzenesulfonyl chloride (676 mg, 3.0 mmol). The mixture was room temperature for 12 hrs. After the reaction was completed, the reaction mixture was evaporated and extracted with ethyl acetate. The organic layer was washed with brine, dried over anhydrous $MgSO_4$ and concentrated under reduced pressure. The residue was purified by flash column chromatography (DCM/MeOH=10/1) to give A39 (4-(2-((4-nitrophenyl)sulfonyl)hydrazine-1-carbonyl)benzamide, 366 mg, yield: 30%) as a white solid. LCMS Calcd m/z for $C_{14}H_{12}N_4O_6S$ $[M+H]^+$ 365.33 Found 365.

Step 4) Synthesis of Compound 18

To a solution of A39 (4-(2-((4-nitrophenyl)sulfonyl)hydrazine-1-carbonyl)benzamide, 366 mg, 1.0 mmol) in THF: MeOH=3:1 (10 mL) was added Zn (657 mg, 10 mmol) and $NH_4Cl$ (537 mg, 10 mmol) at 60° C. for 5 hrs. After the reaction was completed, the reaction mixture was cooled and then added ethyl acetate. The mixture was filterated through Celite. The filterate was concentrated under reduced pressure. The residue was purified by flash column chromatography (DCM/MeOH=15/1) to give compound 18 (4-(2-((4-aminophenyl)sulfonyl)hydrazine-1-carbonyl)benzamide, 10 mg, 4.51 mmol, yield: 3%, purity: 97.0%) as a white solid. 1H NMR (DMSO-$d_6$, 600 MHz) δ (ppm): δ 10.68 (br s, 1H), 9.38 (br s, 1H), 8.06 (s, 1H), 7.90 (d, J=6.0 Hz, 2H), 7.73 (d, J=6.0 Hz, 2H), 7.05 (s, 1H), 7.44 (d, J=6.0 Hz, 2H), 6.51 (d, J=6.0 Hz, 2H), 5.97 (s, 2H); LCMS Calcd m/z for $C_{14}H_{14}N_4O_4S$ $[M+H]^+$ 335.35 Found 335.

Experimental Example 1-19. Preparation of Compound 19 (N'-(4-aminobenzyl)-4-hydroxybenzohydrazide)

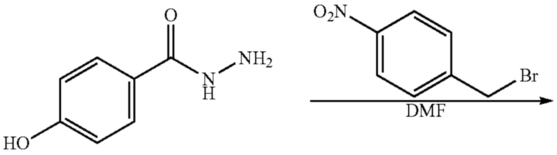

A2

-continued

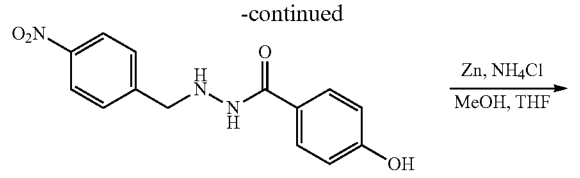

A40

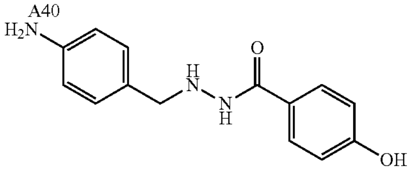

Compound 19

Step 1) Synthesis of A40

To a solution of A2 (500 mg, 3.2 mmol) in DMF (10 mL) was added triethylamine (0.46 mL, 3.2 mmol) and 1-(bromomethyl)-4-nitrobenzene (545 mg, 2.5 mmol). The mixture was room temperature for 12 hrs. After the reaction was completed, the reaction mixture was evaporated and extracted with ethyl acetate. The organic layer was washed with brine, dried over anhydrous $MgSO_4$ and concentrated under reduced pressure. The residue was purified by flash column chromatography (DCM/MeOH=5/1) to give A40 (4-hydroxy-N'-(4-nitrobenzyl)benzohydrazide, 410 mg, yield: 44%) as a yellow solid. LCMS Calcd m/z for $C_{14}H_{13}N_3O_4$ $[M+H]^+$ 288.28 Found 288.

Step 2) Synthesis of Compound 19

To a solution of A40 (4-hydroxy-N'-(4-nitrobenzyl)benzohydrazide, 410 mg, 1.4 mmol) in THF:MeOH=3:1 (12 mL) was added Zn (933 mg, 14 mmol) and $NH_4Cl$ (764 mg, 14 mmol). The mixture was stirred at room temperature for 12 hr. After the reaction was completed and then added ethyl acetate. The mixture was filterated through Celite. The filterate was concentrated under reduced pressure. The residue was purified by flash column chromatography (DCM/MeOH=15/1) to give compound 19 (N'-(4-aminobenzyl)-4-hydroxybenzohydrazide, 6 mg, yield: 16%, purity: 95.0%) as a white solid. 1H NMR (DMSO-$d_6$, 600 MHz) δ (ppm): δ 10.03 (br s, 1H), 9.80 (br s, 1H), 7.67 (d, J=6.0 Hz, 2H), 7.00 (d, J=6.0 Hz, 2H), 6.77 (d, J=6.0 Hz, 2H), 6.51 (d, J=6.0 Hz, 2H), 4.97 (bs, 3H), 3.72 (bs, 2H); LCMS Calcd m/z for $C_{14}H_{15}N_3O_2$ $[M+H]^+$258.29 Found 258.

Experimental Example 1-20. Synthesis of Compound 20 (4-amino-N'-(1H-indole-3-carbonyl)benzenesulfonohydrazide)

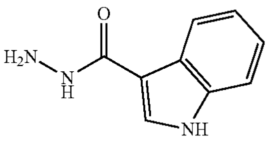

A41

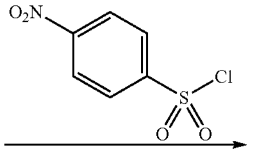

-continued

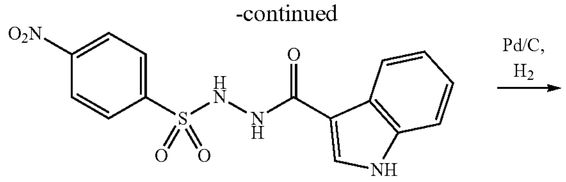

A42

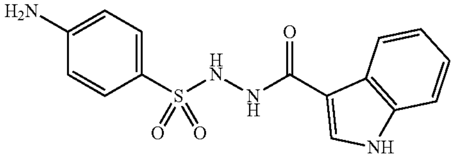

Compound 20

Step 1) Synthesis of A42

To a mixture of A41 (1H-indole-3-carbohydrazide, 500 mg, 2.85 mmol, 1.0 eq) in pyridine (5 mL) was added 4-nitrobenzene-1-sulfonyl chloride (632 mg, 2.85 mmol, 1.0 eq) in pyridine (5 mL) dropwise. Then the mixture was stirred at 10° C. for 2 hrs. The above solution was poured into water (30 mL) and extracted with EA (30 mL×3). The combined organic layers were washed with brine, dried over $Na_2SO_4$ and concentrated to give crude product, which was purified by flash column (DCM/MeOH=50/1~30/1) to give A42 (N'-(1H-indole-3-carbonyl)-4-nitrobenzenesulfonohydrazide, 0.9 g, yield 87.5%) as a yellow solid. (TLC: DCM/MeOH=20/1, Rf=0.5)

Step 2) Synthesis of Compound 20

To a mixture of A42 (N'-(1H-indole-3-carbonyl)-4-nitrobenzenesulfonohydrazide, 300 mg, 0.83 mmol, 1.0 eq) in MeOH (10 mL) was added Pd/C (100 mg). Then the mixture was stirred at 10° C. for 2 hrs under $H_2$ balloon. The above solution was filtered and the filtrate was purified by prep-HPLC and lyophilized to give compound 20 (4-amino-N'-(1H-indole-3-carbonyl)benzenesulfonohydrazide, 30 mg, yield 10.9%) as a yellow solid $^1$HNMR (DMSO-$d_6$, 400 MHz): δ 11.62 (d, J=2.8 Hz, 1H), 9.98 (s, 1H), 9.11 (d, J=3.2 Hz, 1H), 8.00 (d, J=2.8 Hz, 1H), 7.90 (d, J=7.6 Hz, 1H), 7.40-7.46 (m, 3H), 7.05-7.16 (m, 2H), 6.51 (d, J=8.8 Hz, 2H), 5.89 (br s, 2H).

LCMS; Mass Calcd.: 330; MS Found: 331.1 [MS+1].

Experimental Example 1-21 and Experimental Example 1-22. Preparation of Compound 21 (4-amino-N'-(4-hydroxybenzoyl)-3-(pyrrolidin-1-yl)benzenesulfonohydrazide) and Compound 22 (N'-(4-hydroxybenzoyl)-4-nitro-3-(pyrrolidin-1-yl)benzenesulfonohydrazide)

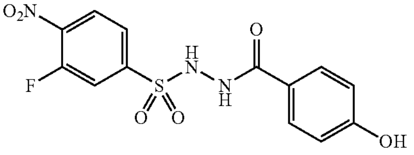

A4

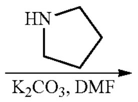

-continued

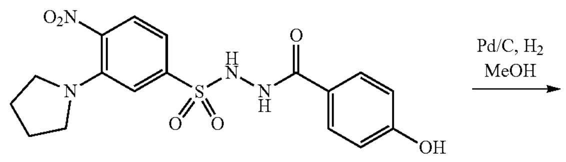

Compound 22

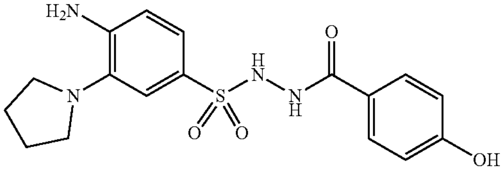

Compound 21

Step 1) Synthesis of Compound 22

To a mixture of A4 (3-fluoro-N'-(4-hydroxybenzoyl)-4-nitrobenzenesulfonohydrazide, 400 mg, 1.13 mmol, 1.0 eq) and $K_2CO_3$ (389 mg, 2.81 mmol, 2.5 eq) in DMF (10 mL) was added pyrrolidine (96 mg, 1.35 mmol, 1.2 eq) at 10° C. Then the mixture was stirred at 25° C. for 16 hrs. The above solution was poured into water (30 mL) and extracted with EA (30 mL×3). The combined organic layers were washed with brine, dried over $Na_2SO_4$ and concentrated to give crude product, which was purified by flash column (DCM/MeOH=50/1~30/1) to give compound 22 (N'-(4-hydroxybenzoyl)-4-nitro-3-(pyrrolidin-1-yl)benzenesulfonohydrazide, 176 mg, yield 38.5%) as a yellow solid. $^1$HNMR (DMSO-$d_6$, 400 MHz): δ 10.48 (s, 1H), 10.14 (s, 2H), 7.86 (d, J=8.8 Hz, 1H), 7.61 (d, J=8.8 Hz, 2H), 7.37 (d, J=1.6 Hz, 1H), 7.11-7.13 (m, 1H), 6.78 (d, J=8.8 Hz, 2H), 3.64 (t, J=6.0 Hz, 4H), 1.86 (t, J=6.0 Hz, 4H).

Step 2) Synthesis of Compound 21

To a mixture of compound 22 (N'-(4-hydroxybenzoyl)-4-nitro-3-(pyrrolidin-1-yl)benzenesulfonohydrazide, 100 mg, 0.54 mmol, 1.0 eq) in MeOH (5 mL) was added Pd/C (30 mg). Then the mixture was stirred at 10° C. for 16 hrs under $H_2$ balloon. The above solution was filtered and the filtrate was concentrated to give crude product, which was stirred in MeOH (5 mL) and DMSO (0.5 mL) for 5 min. The mixture was filtered and the filter cake was washed with MeOH and dried to give compound 21 (4-amino-N'-(4-hydroxybenzoyl)-3-(pyrrolidin-1-yl)benzenesulfonohydrazide, 30 mg, yield 32.4%) as an off-white solid.

1HNMR (DMSO-$d_6$, 400 MHz): δ 10.34 (s, 1H), 10.06 (s, 1H), 9.13 (s, 1H), 7.54 (d, J=8.4 Hz, 2H), 7.17 (t, J=1.6 Hz, 2H), 6.76 (d, J=8.8 Hz, 2H), 6.61 (d, J=8.4 Hz, 1H), 5.47 (s, 2H), 2.80 (s, 4H), 1.77 (s, 4H).

LCMS; Mass Calcd.: 330; MS Found: 331.1 [MS+1].

Experimental Example 1-23. Synthesis of Compound 23 (4-amino-N'-(4-hydroxybenzoyl)-3-(piperidin-1-yl)benzenesulfonohydrazide)

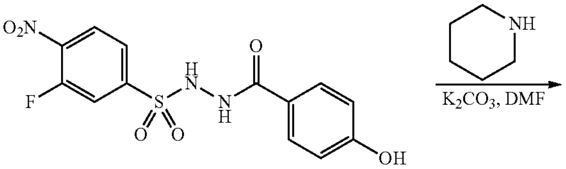

A4

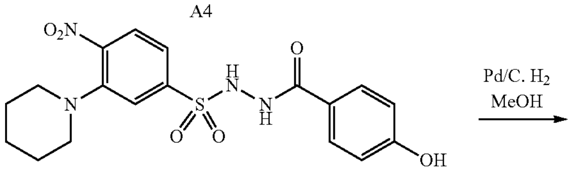

A43

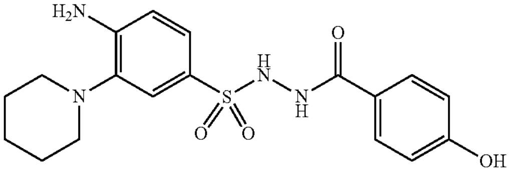

Compound 23

Step 1) Synthesis of A43

To a mixture of A4 (3-fluoro-N'-(4-hydroxybenzoyl)-4-nitrobenzenesulfonohydrazide, 400 mg, 1.13 mmol, 1.0 eq) and $K_2CO_3$ (389 mg, 2.81 mmol, 2.5 eq) in DMF (10 mL) was added piperidine (115 mg, 1.35 mmol, 1.2 eq) at 10° C. Then the mixture was stirred at 25° C. for 16 hrs. The above solution was poured into water (30 mL) and extracted with EA (30 mL×3). The combined organic layers were washed brine, dried over $Na_2SO_4$ and concentrated to give crude product, which was purified by flash column (DCM/MeOH=50/1~30/1) to give A43 (N'-(4-hydroxybenzoyl)-4-nitro-3-(piperidin-1-yl)benzenesulfonohydrazide, 240 mg, yield 50.7%) as a yellow solid. $^1$HNMR (DMSO-$d_6$, 400 MHz): δ 10.53 (s, 1H), 10.21 (s, 1H), 10.15 (s, 1H), 7.91 (d, J=8.4 Hz, 1H), 7.62 (d, J=8.8 Hz, 2H), 7.56 (d, J=1.6 Hz, 1H), 7.40-7.43 (m, 1H), 6.79 (d, J=8.8 Hz, 2H), 2.88 (t, J=5.2 Hz, 4H), 1.50-1.51 (m, 6H).

Step 2) Synthesis of Compound 23

To a mixture of A43 (N'-(4-hydroxybenzoyl)-4-nitro-3-(piperidin-1-yl)benzenesulfonohydrazide, 100 mg, 0.24 mmol, 1.0 eq) in MeOH (5 mL) was added Pd/C (30 mg). Then the mixture was stirred at 10° C. for 16 hrs under $H_2$ balloon. The above solution was filtered and the filtrate was purified by prep-HPLC and lyophilized to give compound 23 (4-amino-N'-(4-hydroxybenzoyl)-3-(piperidin-1-yl)benzenesulfonohydrazide, 25 mg, yield 26.9%) as a yellow solid.

1HNMR (DMSO-$d_6$, 400 MHz): δ 10.37 (d, J=4.0 Hz, 1H), 10.07 (s, 1H), 9.17 (d, J=4.0 Hz, 1H), 7.58 (d, J=8.8 Hz, 2H), 7.2-7.25 (m, 2H), 6.77 (d, J=7.2 Hz, 2H), 6.64 (d, J=8.4 Hz, 1H), 5.51 (s, 2H), 2.55 (s, 4H), 1.55-1.60 (m, 4H), 1.45 (s, 2H).

LCMS; Mass Calcd.: 390; MS Found: 390.8 [MS+1].

Experimental Example 1-24. Synthesis of Compound 24 (N'-(4-hydroxybenzoyl)-1H-pyrazole-4-sulfonohydrazide)

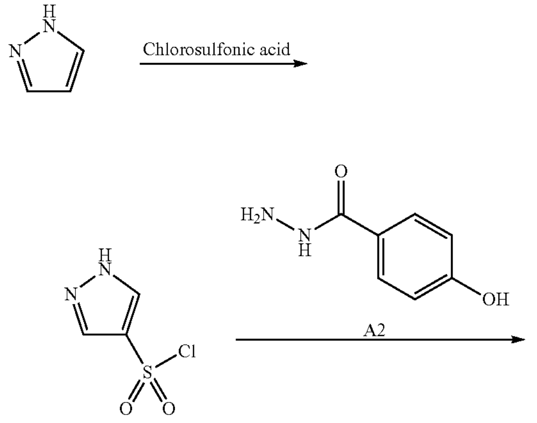

A44

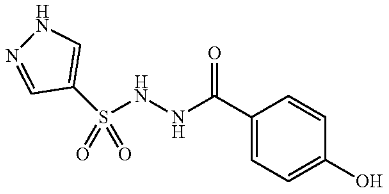

Compound 24

Step 1) Synthesis of A44

A solution of 1H-pyrazole (1 g, 14.7 mmol, 1.0 eq) in Chlorosulfonic acid (5 mL) was stirred at 100° C. for overnight. The above solution was poured into water (30 mL) and extracted with EA (30 mL*3). The combined organic layers were washed with brine, dried over $Na_2SO_4$ and concentrated to give A44 (1H-pyrazole-4-sulfonyl chloride, 340 mg, yield 14%) as an off white solid.

1HNMR (CDCl3, 400 MHz): 8.22 (s, 2H), 7.92 (s, 1H).

Step 2) Synthesis of Compound 24

A mixture of A44 (1H-pyrazole-4-sulfonyl chloride, 100 mg, 0.6 mmol, 1.0 eq) and A2 (4-hydroxybenzohydrazide, 109 mg, 0.72 mmol, 1.2 eq) in Pyridine (20 mL) was stirred at 80° C. overnight. The above solution was poured into water (30 mL) and extracted with EA (30 mL*3). The combined organic layers were washed brine, dried over $Na_2SO_4$ and concentrated to give crude product. The residue was purified by prep-HPLC to give compound 24 (N'-(4-hydroxybenzoyl)-1H-pyrazole-4-sulfonohydrazide, 60 mg) as off white solid.

1HNMR (DMSO-$d_6$, 400 MHz): 13.4 (s, 1H), 10.39 (s, 1H), 10.1 (s, 1H), 9.5 (s, 1H), 8.47-7.63 (m, 2H), 7.62 (d, 2H), 6.78 (d, 2H).

Experimental Example 1-25 and Experimental Example 1-26. Preparation of Compound 25 (N'-(4-hydroxybenzoyl)indoline-4-sulfonohydrazide) and Compound 26 (N'-(4-hydroxybenzoyl)-1H-indole-4-sulfonohydrazide)

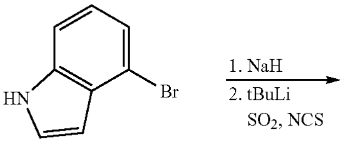

A46

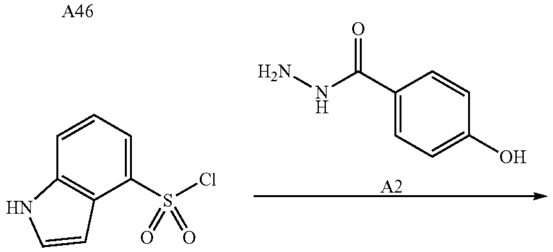

A46

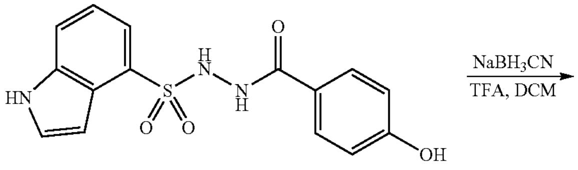

Compound 26

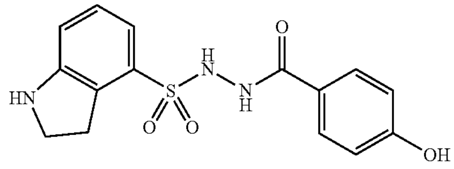

Compound 25

Step 1) Synthesis of A46

To a solution of A45 (4-bromo-1H-indole, 1.0 g, 5.10 mmol, 1.0 eq) in THF (10 mL) and $Et_2O$ (10 mL) was added NaH (204 mg, 5.10 mmol, 60% in mineral oil, 1.0 eq) at 0° C. After stirring for 15 min, the mixture was cooled to −78° C., and t-BuLi (7.9 mL, 10.2 mmol, 1.3 M in THF, 2.0 eq) was added slowly. After 30 min, $SO_2$ (gas, 1 L) was slowly added at −78° C. The mixture was then allowed to warm to rt and stirred overnight. A mixture of acetic acid (307 mg, 5.10 mmol, 1.0 eq) in $Et_2O$ (15 mL) was added at 0° C. The mixture was stirred for 30 min at 0° C. and then filtered. The filter cake was quickly washed with $Et_2O$. The solid was suspended in $Et_2O$ (15 mL), cooled to 0° C. and NCS (682 g, 5.10 mmol, 1.0 eq) was carefully added. The resulting suspension was stirred rapidly for 30 min, and then filtered. The filter cake was washed with $Et_2O$. The combined filtrate were concentrated to provide A46 (1H-indole-4-sulfonyl chloride, 420 mg, crude) as a brown solid.

Step 2) Synthesis of Compound 26

A mixture of A46 (1H-indole-4-sulfonyl chloride, 420 mg, 1.95 mmol, 1.0 eq) and 4-hydroxybenzohydrazide (A2, 297 mg, 1.95 mmol, 1.0 eq) in pyridine (30 mL) was stirred at 25° C. for 30 min. The above solution was poured into water (30 mL). The formed solid was collected by filtration and the filter cake was washed with water. The crude product was purified by prep-HPLC and lyophilized to give compound 26 (N'-(4-hydroxybenzoyl)-1H-indole-4-sulfonohydrazide, 200 mg, yield 31.0%) as a white solid.

$^1$HNMR (DMSO-$d_6$, 400 MHz): δ 11.48 (s, 1H), 10.30 (s, 1H), 10.04 (s, 1H), 9.52 (s, 1H), 7.65 (d, J=8.0 Hz, 1H), 7.49-7.52 (m, 4H), 7.16 (t, J=8.0 Hz, 1H), 6.85 (t, J=2.0 Hz, 1H), 6.73 (dd, J=6.8, 2.0 Hz, 2H).

LCMS; Mass Calcd.: 331.3; MS Found: 331.9 [MS+1].

Step 3) Synthesis of Compound 25

To a mixture of compound 26 (N'-(4-hydroxybenzoyl)-1H-indole-4-sulfonohydrazide, 150 mg, 0.48 mmol, 1.0 eq) in TFA (5 mL) and DCM (5 mL) was added $NaBH_3CN$ (89 mg, 1.43 mmol, 3.0 eq) at 0° C. The mixture was stirred at 10° C. for 30 min. The above solution was poured into water (30 mL) and extracted with DCM (30 mL×3). The combined organic layers were washed with brine, dried over $Na_2SO_4$ and concentrated to give crude product, which was purified by prep-HPLC and lyophilized to give compound 25 (N'-(4-hydroxybenzoyl)indoline-4-sulfonohydrazide, 30 mg, yield 20.0%) as a gray solid.

1HNMR (DMSO-$d_6$, 400 MHz): δ 10.35 (d, J=2.8 Hz, 1H), 10.09 (s, 1H), 9.62 (d, J=2.8 Hz, 1H), 7.57 (d, J=8.8 Hz, 2H), 6.97-6.99 (m, 1H), 6.93 (d, J=6.8 Hz, 1H), 6.76 (d, J=8.8 Hz, 2H), 6.67 (d, J=7.2 Hz, 1H), 3.39-3.44 (m, 2H), 3.27-3.32 (m, 2H).

LCMS; Mass Calcd.: 333; MS Found: 333.8 [MS+1].

Experimental Example 1-27. Preparation of Compound 27 (2-((4-aminophenyl)sulfonyl)-N-phenylhydrazine-1-carboxamide)

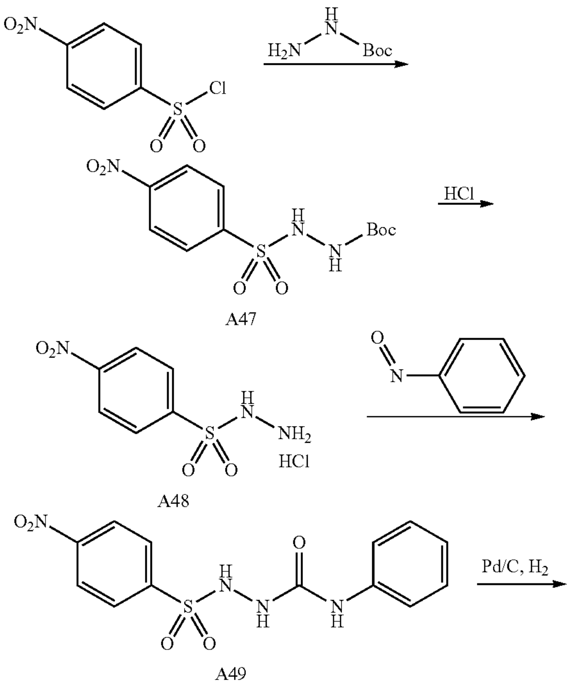

-continued

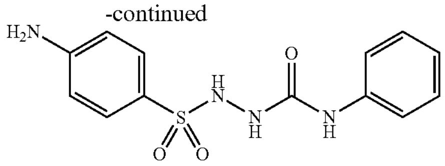

Compound 27

Step 1) Synthesis of A47

To a mixture of 4-nitrobenzenesulfonyl chloride (3 g, 13.5 mmol, 1.0 eq) in pyridine (25 mL) was added tert-butyl hydrazinecarboxylate (1.8 g, 13.6 mmol, 1.0 eq) in pyridine (5 mL) dropwise. Then the mixture was stirred at 10° C. for 2 hrs. The above solution was poured into water (100 mL) and the solution was stirred for 1 hr. The formed solid was collected by filtration and dried to give A47 (tert-butyl 2-((4-nitrophenyl)sulfonyl)hydrazine-1-carboxylate, 3.0 g, yield 69.7%) as a yellow solid.

1HNMR ($CDCl_3$, 400 MHz): δ 8.35 (d, J=8.4 Hz, 2H), 8.13 (dd, J=7.2, 2.0 Hz, 2H), 6.79 (s, 1H), 6.68 (s, 1H), 1.25 (s, 9H).

Step 2) Synthesis of A48

To a mixture of A47 (tert-butyl 2-((4-nitrophenyl)sulfonyl)hydrazine-1-carboxylate, 3 g, 9.45 mmol, 1.0 eq) in MeOH (30 mL) was added MeOH/HCl (30 mL, 6 mol/L). Then the mixture was stirred at 10° C. for 2 hrs. The above solution was concentrated to give A48 (4-nitrobenzenesulfonohydrazide hydrochloride, 2.0 g, yield 83.4%) as a yellow solid.

1HNMR (DMSO-$d_6$, 400 MHz): δ 8.45-8.48 (m, 2H), 8.15 (d, J=8.8 Hz, 2H).

Step 3) Synthesis of A49

To a mixture of A48 (4-nitrobenzenesulfonohydrazide hydrochloride, 500 mg, 1.97 mmol, 1.0 eq) in THF (20 mL) was added DIEA (764 mg, 5.91 mmol, 3.0 eq) and isocyanatobenzene (235 mg, 1.97 mmol, 1.0 eq) at 10° C. Then the mixture was stirred at 10° C. for 2 hrs. The above solution was poured into water (80 mL). The formed solid was filtered and the filter cake was stirred in EA (20 mL) for 30 min. Then the mixture was filtered again and the filter cake was dried to give A49 (2-((4-nitrophenyl)sulfonyl)-N-phenylhydrazine-1-carboxamide, 340 mg, yield 51.3%) as a white solid.

1HNMR (DMSO-$d_6$, 400 MHz): δ 10.09 (s, 1H), 8.69 (s, 1H), 8.53 (s, 1H), 8.40-8.43 (m, 2H), 8.09 (dd, J=7.2, 2.0 Hz, 2H), 7.34 (t, J=8.0 Hz, 2H), 7.21 (t, J=8.0 Hz, 1H), 6.94 (t, J=7.2 Hz, 1H).

Step 4) Synthesis of Compound 27

A mixture of A49 (2-((4-nitrophenyl)sulfonyl)-N-phenylhydrazine-1-carboxamide, 340 mg, 1.01 mmol, 1.0 eq) and Pd/C (200 mg) in MeOH (30 mL) was stirred at 10° C. for 15 hrs under $H_2$ balloon. The above solution was filtered and the filtrate was concentrated to give crude product, which was stirred in MeOH (5 mL) for 30 min. The mixture was filtered and the filter cake was dried in vacuo to give compound 27 (2-((4-aminophenyl)sulfonyl)-N-phenylhydrazine-1-carboxamide, 50 mg, yield 16.2%) as a white solid.

1HNMR (DMSO-$d_6$, 400 MHz): δ 9.12 (s, 1H), 8.41 (s, 1H), 8.15 (s, 1H), 7.47 (d, J=8.8 Hz, 2H), 7.38 (d, J=8.0 Hz, 2H), 7.22 (t, J=8.0 Hz, 2H), 6.94 (t, J=7.2 Hz, 1H), 6.60 (d, J=8.8 Hz, 2H), 6.04 (s, 2H).

LCMS; Mass Calcd.: 306; MS Found: 306.9.

Experimental Example 1-28. Preparation of Compound 28 (4-amino-N'-(1H-indole-4-carbonyl)-3-morpholinobenzenesulfonohydrazide)

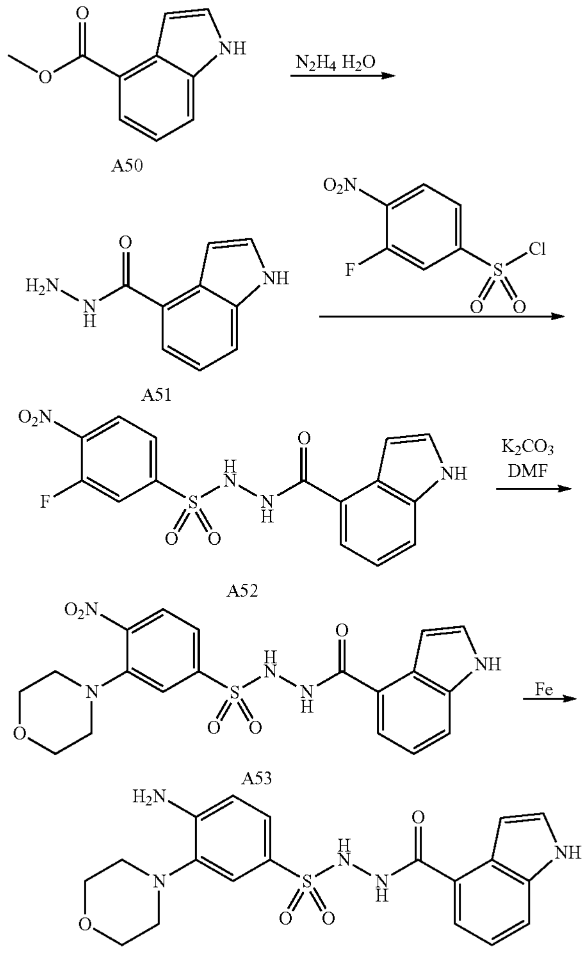

A50

A51

A52

A53

Compound 28

Step 1) Synthesis of A51

A mixture of A50 (methyl 1H-indole-4-carboxylate, 1.00 g, 5.71 mmol, 1.0 eq) in $N_2H_4H_2O$ (10 mL) was stirred at 100° C. for 1 hr. The above solution was poured into water and extracted with EA (30 mL×3). The combined organic layers were dried over $Na_2SO_4$ and concentrated to give A51 (1H-indole-4-carbohydrazide, 500 mg, crude) as a yellow solid.

Step 2) Synthesis of A52

To a mixture of A51 (1H-indole-4-carbohydrazide, 100 mg, 0.57 mmol, 1.0 eq) in pyridine (2 mL) was added 3-fluoro-4-nitrobenzene-1-sulfonyl chloride (175 mg, 0.57 mmol, 1.0 eq) in pyridine (2 mL) dropwise. Then the mixture was stirred at 10° C. for 3 hrs. The above solution was poured into water (30 mL) and extracted with EA (30 mL×3). The combined organic layers were washed with 1N HCl (30 mL×2) and brine, dried over $Na_2SO_4$ and concentrated to give A52 (3-fluoro-N'-(1H-indole-4-carbonyl)-4-nitrobenzenesulfonohydrazide, 200 mg, crude) as a yellow solid.

Step 3) Synthesis of A53

To a mixture of A52 (3-fluoro-N'-(1H-indole-4-carbonyl)-4-nitrobenzenesulfonohydrazide, 200 mg, 0.52 mmol, 1.0 eq) and $K_2CO_3$ (183 mg, 1.30 mmol, 2.5 eq) in DMF (5 mL) was added morpholine (54 mg, 0.62 mmol, 1.2 eq) at 10° C. Then the mixture was stirred at 25° C. for 16 hrs. The above solution was poured into water (30 mL) and extracted with EA (30 mL×3). The combined organic layers were washed brine, dried over $Na_2SO_4$ and concentrated to give A53 (N'-(1H-indole-4-carbonyl)-3-morpholino-4-nitrobenzenesulfonohydrazide, 100 mg, crude) as a yellow solid.

Step 4) Synthesis of Compound 28

To a mixture of A53 (N'-(1H-indole-4-carbonyl)-3-morpholino-4-nitrobenzenesulfonohydrazide, 100 mg, 0.22 mmol, 1.0 eq) in EtOH (5 mL) was added Fe (61.6 mg, 1.10 mmol, 5.0 eq) and sat. aq. $NH_4Cl$ (3 mL). Then the mixture was stirred at 85° C. for 3 hrs. The above solution was filtered and the filtrate was purified by prep-HPLC and lyophilized to give compound 28 (4-amino-N'-(1H-indole-4-carbonyl)-3-morpholinobenzenesulfonohydrazide, 20 mg, yield 21.5%) as a white solid.

$^1$HNMR (DMSO-$d_6$, 400 MHz): δ 11.30 (s, 1H), 10.34 (s, 1H), 9.35 (d, J=4.0 Hz, 1H), 7.54 (d, J=8.4 Hz, 1H), 7.43 (t, J=2.4 Hz, 1H), 7.30-7.35 (m, 3H), 7.11 (t, J=7.6 Hz, 1H), 6.65-6.67 (m, 2H), 5.60 (br s, 2H), 3.64 (t, J=4.0 Hz, 4H), 2.60 (t, J=4.0 Hz, 4H).

LCMS; Mass Calcd.: 415; MS Found: 415.9 [MS+1].

Experimental Example 1-29. Preparation of Compound 29 (4-amino-N'-(indoline-4-carbonyl)benzenesulfonohydrazide)

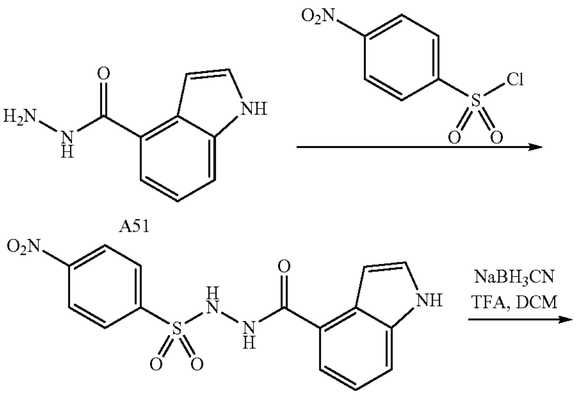

A51

A54

-continued

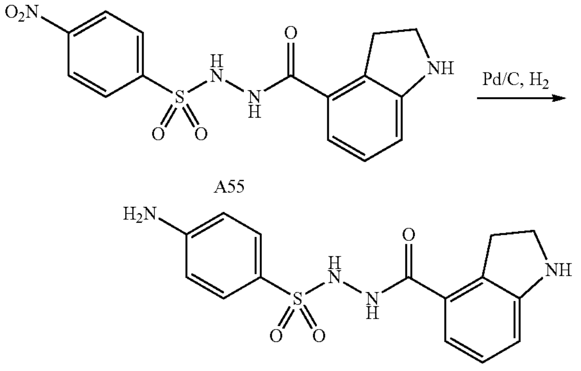

A55

Compound 29

Step 1) Synthesis of A54

To a mixture of A51 (1H-indole-4-carbohydrazide, 400 mg, 2.29 mmol, 1.0 eq) in pyridine (5 mL) was added 4-nitrobenzene-1-sulfonyl chloride (505 mg, 2.29 mmol, 1.0 eq) in pyridine (5 mL) dropwise. Then the mixture was stirred at 10° C. for 3 hrs. The above solution was poured into water (30 mL) and extracted with EA (30 mL×3). The combined organic layers were washed with brine, dried over $Na_2SO_4$ and concentrated to give A54 (N'-(1H-indole-4-carbonyl)-4-nitrobenzenesulfonohydrazide, 300 mg, crude) as a yellow solid.

Step 2) Synthesis A55

To a mixture of A54 (N'-(1H-indole-4-carbonyl)-4-nitrobenzenesulfonohydrazide, 300 mg, 0.83 mmol, 1.0 eq) in DCM (5 mL) was added TFA (1.5 mL) and $NaBH_3CN$ (157 mg, 2.49 mmol, 3.0 eq) at 10° C. Then the mixture was stirred at 10° C. for 45 min. The above solution was poured into water (30 mL) and adjusted pH=7 with sat. aq. $NaHCO_3$. The mixture was filtered and the filter cake was washed with MTBE and dried in vacuo to give A55 (N'-(indoline-4-carbonyl)-4-nitrobenzenesulfonohydrazide, 150 mg, crude) as a yellow solid.

Step 3) Synthesis of Compound 29

A mixture of A55 (N'-(indoline-4-carbonyl)-4-nitrobenzenesulfonohydrazide, 150 mg, 0.41 mmol, 1.0 eq) and Pd/C (100 mg) in MeOH (5 mL) was stirred at 10° C. for 2 hrs under $H_2$ balloon. The above solution was filtered and the filtrate was concentrated to give crude product, which was stirred in MeOH (10 mL) for 30 min. The mixture was filtered and the filter cake was dried in vacuo to give compound 29 (4-amino-N'-(indoline-4-carbonyl)benzenesulfonohydrazide, 40 mg, yield 29.1%) as a white solid.

1HNMR (DMSO-$d_6$, 400 MHz): δ 10.28 (d, J=3.6 Hz, 1H), 9.28 (d, J=3.6 Hz, 1H), 7.46 (d, J=8.4 Hz, 2H), 7.03 (t, J=8.0 Hz, 1H), 6.83 (d, J=7.2 Hz, 1H), 6.75 (d, J=7.2 Hz, 1H), 6.53 (d, J=8.8 Hz, 2H), 3.42 (t, J=8.4 Hz, 2H), 2.96 (t, J=8.4 Hz, 2H).

LCMS; Mass Calcd.: 332; MS Found: 332.8 [MS+1].

Experimental Example 1-30. Preparation of Compound 30 (4-amino-N'-(4-hydroxybenzoyl)-3-(piperazin-1-yl)benzenesulfonohydrazide)

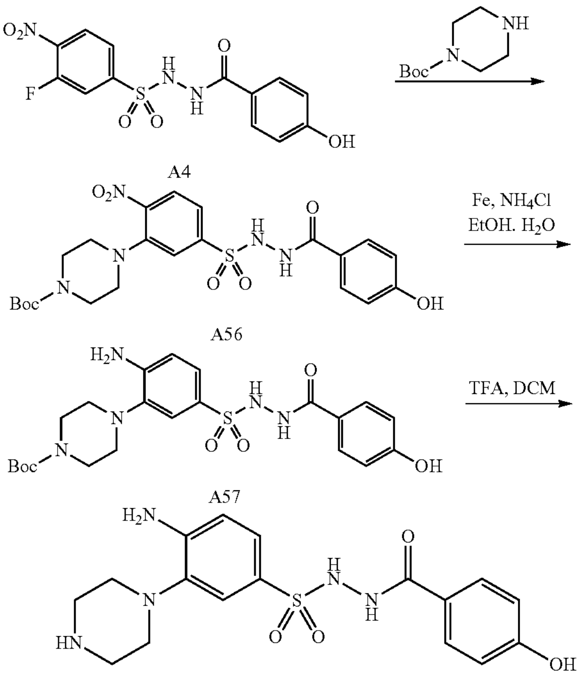

A4

A56

A57

Compound 30

Step 1) Synthesis of A56

To a mixture of A4 (3-fluoro-N'-(4-hydroxybenzoyl)-4-nitrobenzenesulfonohydrazide, 500 mg, 1.41 mmol, 1.0 eq) and $K_2CO_3$ (290 mg, 2.10 mmol, 1.5 eq) in DMF (5 mL) was added tert-butyl piperazine-1-carboxylate (315 mg, 1.69 mmol, 1.2 eq) at 10° C. Then the mixture was stirred at 10° C. for 16 hrs. The above solution was poured into water (30 mL) and extracted with EA (30 mL×3). The combined organic layers were washed with brine, dried over $Na_2SO_4$ and concentrated to give crude product, which was purified by flash column (DCM/MeOH=50/1~30/1) to give A56 (tert-butyl 4-(5-((2-(4-hydroxybenzoyl)hydrazinyl)sulfonyl)-2-nitrophenyl)piperazine-1-carboxylate, 310 mg, crude) as a yellow solid.

Step 2) Synthesis of A57

To a mixture of A56 (tert-butyl 4-(5-((2-(4-hydroxybenzoyl)hydrazinyl)sulfonyl)-2-nitrophenyl)piperazine-1-carboxylate, 250 mg, 0.48 mmol, 1.0 eq) in EtOH (3 mL) was added sat. aq. $NH_4Cl$ (3 mL) and Fe (135 mg, 2.41 mmol, 5.0 eq). Then the mixture was stirred at 85° C. for 1 hr. The above solution was filtered and the filtrate was poured into water (30 mL) and extracted with EA (30 mL×3). The combined organic layers were washed with brine, dried over $Na_2SO_4$ and concentrated to give A57 (tert-butyl 4-(2-amino-5-((2-(4-hydroxybenzoyl)hydrazinyl)sulfonyl)phenyl)piperazine-1-carboxylate, 210 mg, crude) as a yellow solid.

Step 3) Synthesis of Compound 30

To a mixture of A57 (tert-butyl 4-(2-amino-5-((2-(4-hydroxybenzoyl)hydrazinyl)sulfonyl)phenyl)piperazine-1- carboxylate, 270 mg, 0.55 mmol, 1.0 eq) in DCM (5 mL) was added TFA (0.5 mL) at 10° C. Then the mixture was stirred at 10° C. for 3 hrs. The above solution was concentrated to give crude product, which was purified by prep-HPLC and lyophilized to give crude product. The crude product was stirred in MeOH (2.5 mL) and $CH_3CN$ (2.5 mL) for 5 min. The mixture was filtered and the filter cake was washed with MeOH and dried to give compound 30 (4-amino-N'-(4-hydroxybenzoyl)-3-(piperazin-1-yl)benzenesulfonohydrazide, 20 mg, yield 9.30%) as a white solid.

1HNMR (DMSO-$d_6$, 400 MHz): δ 7.57 (d, J=8.0 Hz, 2H), 7.21-7.25 (m, 2H), 6.76 (d, J=8.0 Hz, 2H), 6.64 (d, J=8.4 Hz, 1H), 5.54 (s, 2H), 2.78 (s, 4H), 2.54 (s, 4H).

LCMS; Mass Calcd.: 391; MS Found: 392.1 [MS+1].

Experimental Example 1-31. Preparation of Compound 31 (4-amino-N'-(2,3-dihydro-1H-indene-2-carbonyl)benzenesulfonohydrazide)

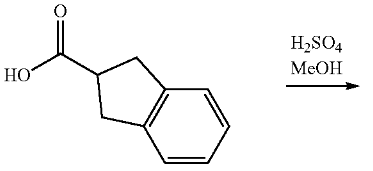

A58

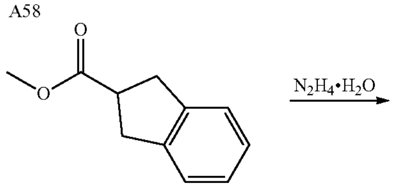

A59

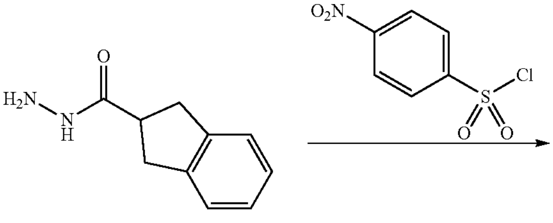

A60

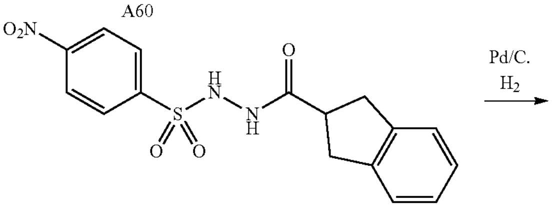

A61

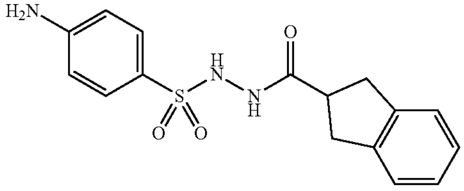

Compound 31

Step 1) Synthesis of A59

To a mixture of A58 (2,3-dihydro-1H-indene-2-carboxylic acid, 5.0 g, 30.8 mmol, 1.0 eq) in MeOH (50 mL) was added $H_2SO_4$ (5 mL) dropwise. Then the mixture was stirred at 70° C. for 12 hrs. The above solution was poured into water (60 mL) and extracted with EA (60 mL×3). The combined organic layers were washed with brine, dried over $Na_2SO_4$ and concentrated to give A59 (methyl 2,3-dihydro-1H-indene-2-carboxylate, 5.3 g, yield 97.5%) as yellow oil.

Step 2) Synthesis of A60

To a mixture of A59 (methyl 2,3-dihydro-1H-indene-2-carboxylate, 3.0 g, 17.1 mmol, 1.0 eq) in MeOH (30 mL) was added $N_2H_4·H_2O$ (8.56 g, 171 mmol, 10 eq) dropwise. Then the mixture was stirred at 80° C. for 12 hrs. The above solution was concentrated to give A60 (2,3-dihydro-1H-indene-2-carbohydrazide, 2.0 g, yield 87.5%) as a yellow solid.

1HNMR (DMSO-$d_6$, 400 MHz): δ 9.13 (s, 1H), 7.18-7.20 (m, 2H), 7.11-7.13 (m, 2H), 4.25 (br s, 2H), 3.01-3.11 (m, 5H).

Step 3) Synthesis of A61

To a mixture of A60 (2,3-dihydro-1H-indene-2-carbohydrazide, 2 g, 11.4 mmol, 1.0 eq) in pyridine (20 mL) was added 4-nitrobenzene-1-sulfonyl chloride (2.52 g, 11.4 mmol, 1.0 eq) in portions. Then the mixture was stirred at 10° C. for 2 hrs. The above solution was poured into water (100 mL) and extracted with EA (100 mL×3). The combined organic layers were washed with brine, dried over $Na_2SO_4$ and concentrated to give to give A61 (N'-(2,3-dihydro-1H-indene-2-carbonyl)-4-nitrobenzenesulfonohydrazide, 1.4 g, yield 34.1%) as a yellow solid. (TLC: DCM/MeOH=10/1, Rf=0.5)

Step 4) Synthesis of Compound 31

To a mixture of A61 (N'-(2,3-dihydro-1H-indene-2-carbonyl)-4-nitrobenzenesulfonohydrazide, 200 mg, 0.83 mmol, 1.0 eq) in MeOH (10 mL) was added Pd/C (100 mg). Then the mixture was stirred at 10° C. for 12 hrs under $H_2$ balloon. The above solution was filtered and the filtrate was purified by prep-HPLC and lyophilized to give compound 31 (4-amino-N'-(2,3-dihydro-1H-indene-2-carbonyl)benzenesulfonohydrazide, 80 mg, yield 43.6%) as a white solid.

$^1$HNMR ($CD_3OD$, 400 MHz): δ 7.55 (dd, J=6.8, 2.0 Hz, 2H), 7.07-7.12 (m, 4H), 6.65 (dd, J=6.8, 2.0 Hz, 2H), 2.92-3.03 (m, 5H).

LCMS; Mass Calcd.: 331; MS Found: 331.8 [MS+1].

Experimental Example 1-32. Preparation of Compound 32 (4-amino-N'-(isoindoline-2-carbonyl)benzenesulfonohydrazide)

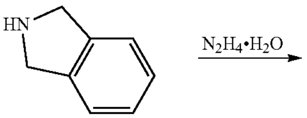

A62

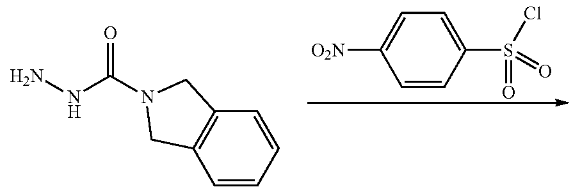

A63

-continued

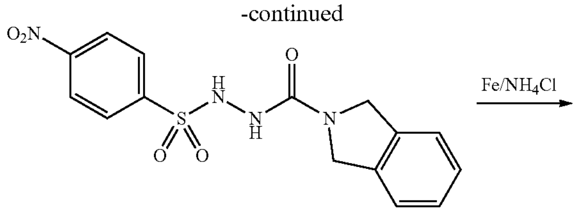

A64

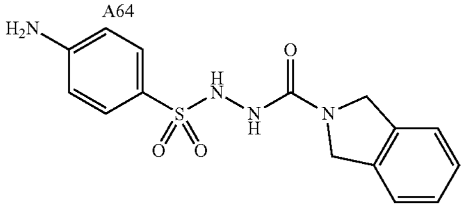

Compound 32

Step 1) Synthesis of A63

To a mixture of A62 (isoindoline, 1.00 g, 8.4 mmol, 1.0 eq) in dichloromethane (10 mL) was added triethylamine (2 mL) and 4-Nitrophenyl chloroformate (1.68 g, 8.4 mmol). The mixture was stirred at r.t for 16 hrs. The above solution was poured into water (30 mL) and extracted with dichloromethane (30 mL×3). The combined organic layers were dried over $Na_2SO_4$ and concentrated. The product was added into tetrahydrofuran (10 mL) and $N_2H_4H_2O$ (2 mL). The mixture was stirred at 60° C. for 16 hrs. The above solution was poured into water (50 mL) and extracted with ethylacetate (30 mL×3). The combined organic layers were dried over sodium sulfate ($Na_2SO_4$) and concentrated to give A63 (isoindoline-2-carbohydrazide, 600 mg, crude) as a yellow solid. (TLC: DCM/MeOH=10/1, Rf=0.6) LCMS; Mass Calcd.: 177.2; MS Found: 178.2 [MS+1].

Step 2) Synthesis of A64

To a mixture of A63 (isoindoline-2-carbohydrazide, 600 mg, 3.39 mmol, 1.0 eq) in pyridine (10 mL) was added 4-nitrobenzene-1-sulfonyl chloride (750 mg, 3.39 mmol, 1.0 eq) in pyridine (5 mL) dropwise. Then the mixture was stirred at 10° C. for 3 hrs. The above solution was poured into water (50 mL) and extracted with EA (50 mL×3). The combined organic layers were washed with 1N HCl (50 mL×2) and brine, dried over $Na_2SO_4$ and concentrated to give A64 (N'-(isoindoline-2-carbonyl)-4-nitrobenzenesulfonohydrazide, 200 mg, crude) as a yellow solid. (TLC: DCM/MeOH=20/1, Rf=0.5)

LCMS; Mass Calcd.: 362.3; MS Found: 363.1 [MS+1].

Step 3) Synthesis of Compound 32 (4-amino-N'-(isoindoline-2-carbonyl)benzenesulfonohydrazide)

To a mixture of A64 (200 mg, 0.55 mmol, 1.0 eq) in ethanol (10 mL) was added Fe (154 mg, 2.75 mmol, 5.0 eq) and sat. aq. $NH_4Cl$ (6 mL). Then the mixture was stirred at 85° C. for 3 hrs. The above solution was filtered, and the filtrate was concentrated to give crude product. The crude product was purified by prep-HPLC and lyophilized to give compound 32 (4-amino-N'-(isoindoline-2-carbonyl)benzenesulfonohydrazide, 20 mg, yield 11.0%) as a white solid.

1HNMR (DMSO-$d_6$, 400 MHz): δ 8.64 (s, 1H), 8.53 (s, 1H), 7.41-7.44 (m, 2H), 7.29-7.31 (m, 4H), 6.51-6.54 (m, 2H), 5.93 (s, 2H), 4.51 (s, 4H).

LCMS; Mass Calcd.: 332; MS Found: 333 [MS+1].

Experimental Example 1-33. Preparation of Compound 33 (N'-(4-hydroxybenzoyl)-1H-indole-2-sulfonohydrazide)

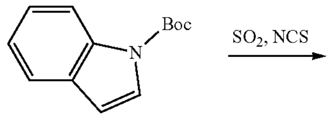

A65

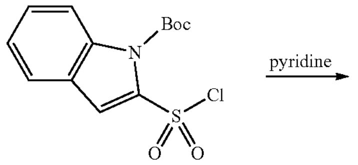

A66

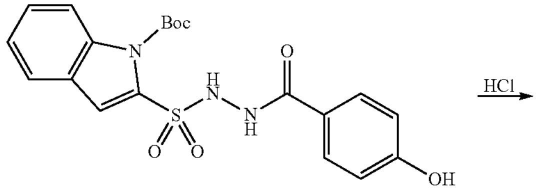

A67

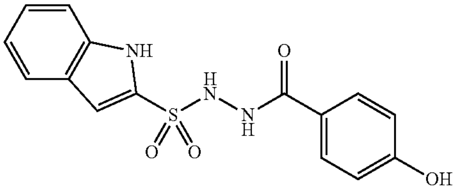

Compound 33

Step 1) Synthesis of A66

To a stirred solution of A65 (tert-butyl 1H-indole-1-carboxylate, 2.00 g, 9.2 mmol, 1.0 eq) in tetrahydrofuran (20 mL) was added dropwise n-BuLi (4.0 mL, 2.5M in hexanes, 10.0 mmol, 1.1 eq) at −70° C. After 1 hr, $SO_2$ (gas, 1 L) was slowly added at −70° C. The reaction mixture was then allowed to warm to 10° C. over a period of 2 hrs. The solvent was removed under reduced pressure. The residue was dissolved in dichloromethane (DCM, 20 mL). N-Chlorosuccinimide (NCS, 1.84 g, 13.8 mmol, 1.5 eq) was added. The mixture was stirred for 10 hrs at r.t. The mixture was washed with water (2×20 mL) and brine (2×20 mL). The organic phase was dried and concentrated. The residue was purified by column chromatography (PE/EA=30/1-5/1) to give A66 (tert-butyl 2-(chlorosulfonyl)-1H-indole-1-carboxylate, 1.0 g, yield 34.4%) as brown oil.

1HNMR ($CDCl_3$, 400 MHz): δ 8.23-8.25 (m, 1H), 7.72 (d, J=8.0 Hz, 1H), 7.69 (s, 1H), 7.56-7.60 (m, 1H), 7.35-7.39 (m, 1H), 1.75 (s, 9H).

Step 2) Synthesis of A67

To a stirred solution of 4-hydroxybenzohydrazide (481 mg, 3.17 mmol, 1.0 eq) in pyridine (10 mL) was added dropwise a solution of A66 (tert-butyl 2-(chlorosulfonyl)-1H-indole-1-carboxylate, 1.0 g, 3.17 mmol, 1.0 eq) in pyridine (5 mL) at 0° C. The mixture was stirred at r.t. for 5 hrs. The mixture was filtered. The filtrate was concentrated and purified by column chromatography to give A67 (tert-butyl 2-((2-(4-hydroxybenzoyl)hydrazinyl)sulfonyl)-1H-indole-1-carboxylate, 500 mg, yield 36.5%) as a white solid.

Step 3) Synthesis of Compound 33

To a stirred solution of A67 (500 mg, 1.16 mmol, 1.0 eq) in methanol (MeOH, 5 mL) was added 4N HCl(g)/MeOH (2 mL) at 0° C. The mixture was stirred at r.t. for 4 hrs. The mixture was concentrated, purified by prep-HPLC and lyophilized to give compound 33 (N'-(4-hydroxybenzoyl)-1H-indole-2-sulfonohydrazide, 50 mg, yield 13%) as an off-white solid.

1HNMR (DMSO-$d_6$, 400 MHz): δ 11.94 (s, 1H), 10.42 (d, J=1.6 Hz, 1H), 10.09 (s, 1H), 9.86 (d, J=2.8 Hz, 1H), 7.61-7.64 (m, 3H), 7.45-7.47 (m, 1H), 7.24-7.28 (m, 1H), 7.07-7.11 (m, 1H), 6.99 (d, J=1.2 Hz, 1H), 6.77 (d, J=8.8 Hz, 2H).

LCMS; Mass Calcd.: 341; MS Found: 342 [MS+1].

Experimental Example 1-34. Preparation of Compound 34 (4-amino-N'-(2-phenylacetyl)benzenesulfonohydrazide)

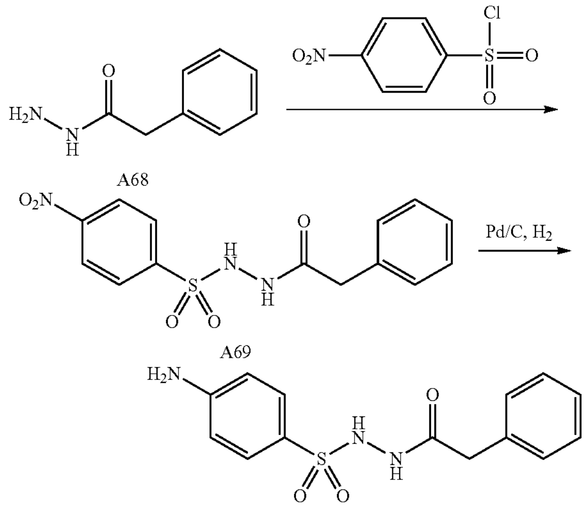

A68

A69

Compound 34

Step 1) Synthesis of A69

To a mixture of A68 (2-phenylacetohydrazide, 500 mg, 3.33 mmol, 1.0 eq) in pyridine (5 mL) was added 4-nitrobenzene-1-sulfonyl chloride (738 mg, 3.33 mmol, 1.0 eq) in pyridine (5 mL) dropwise. Then the mixture was stirred at 10° C. for 2 hrs. The above solution was poured into water (30 mL) and extracted with ethylacetate (EA, 30 mL×3). The combined organic layers were washed with brine, dried over $Na_2SO_4$ and concentrated to give crude product, which was stirred in DCM (30 mL) for 30 min. The mixture was filtered and the filter cake was dried to give A69 (4-nitro-N'-(2-phenylacetyl)benzenesulfonohydrazide, 1 g, yield 89.6%) as a yellow solid.

1HNMR (DMSO-$d_6$, 400 MHz): δ 10.50 (s, 1H), 10.37 (s, 1H), 8.22 (d, J=8.8 Hz, 2H), 7.92 (d, J=8.8 Hz, 2H), 7.21-7.29 (m, 3H), 7.10-7.12 (m, 2H), 3.30 (s, 2H).

Step 1) Synthesis of Compound 34

To a mixture of A69 (200 mg, 0.60 mmol, 1.0 eq) in MeOH (10 mL) was added Pd/C (50 mg). Then the mixture was stirred at 10° C. for 2 hrs under $H_2$ balloon. The above solution was filtered and the filtrate was concentrated. The crude product was crystallized three times from MeOH (10 mL) to give compound 34 (4-amino-N'-(2-phenylacetyl)benzenesulfonohydrazide, 20 mg, yield 10.9%) as a gray solid. (TLC: DCM/MeOH=10/1, Rf=0.3)

1HNMR (DMSO-$d_6$, 400 MHz): δ 9.87 (s, 1H), 8.77 (s, 1H), 7.40 (d, J=6.8 Hz, 2H), 7.18-7.29 (m, 3H), 7.13 (d, J=6.8 Hz, 2H), 5.74 (s, 2H), 3.37 (s, 2H).

LCMS; Mass Calcd.: 305; MS Found: 306.1 [MS+1].

Experimental Example 1-35. Preparation of Compound 35 (N'-(4-hydroxybenzoyl)-1H-indazole-3-sulfonohydrazide)

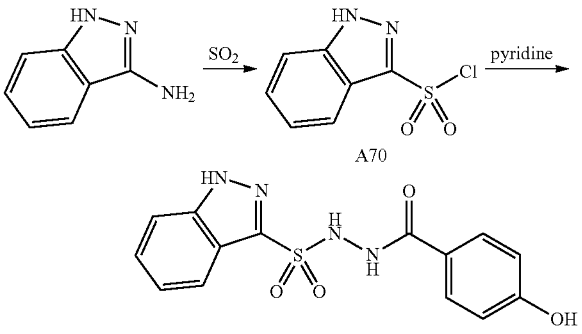

A70

Compound 35

Step 1) Synthesis of A70

To a stirred solution of 1H-indazol-3-amine (1.00 g, 7.5 mmol, 1.0 eq) in acetic acid (16 mL), con. hydrochloric acid (1.6 mL) and formic acid (1.6 mL) was added $NaNO_2$ (0.62 g, 9.0 mmol, 1.2 eq) at 0° C. The mixture was stirred for 1 hr. $SO_2$ (gas, 1 L) and $CuCl_2$ (0.38 g, 2.3 mmol, 0.3 eq) was added slowly at 0° C. The reaction mixture was warmed to 10° C. The mixture was concentrated under reduced pressure. The residue was purified by column chromatography (PE/EA=30:1-1:1) to give A70 (1H-indazole-3-sulfonyl chloride, 0.5 g, yield 30.8%) as a brown solid.

1HNMR (DMSO-$d_6$, 400 MHz): δ 14.13 (s, 2H), 7.94-7.92 (m, 1H), 7.46-7.38 (m, 2H), 7.14 (s, 1H).

Step 2) Synthesis of Compound 35 (N'-(4-hydroxybenzoyl)-1H-indazole-3-sulfonohydrazide)

To a stirred solution of 4-hydroxybenzohydrazide (225 mg, 1.48 mmol, 0.8 eq) in pyridine (5 mL) was added dropwise a solution of A70 (1H-indazole-3-sulfonyl chloride, 0.40 g, 1.85 mmol, 1.0 eq) in pyridine (5 mL) at 0° C. The mixture was stirred at r.t. for 5 hrs. The mixture was concentrated. The residue was purified by prep-HPLC and lyophilized to give compound 35 (N'-(4-hydroxybenzoyl)-1H-indazole-3-sulfonohydrazide, 60 mg, yield 9.77%) as a white solid.

1HNMR (DMSO-$d_6$, 400 MHz): δ 13.90 (s, 1H), 10.43 (s, 1H), 10.05-9.99 (m, 2H), 7.92 (d, J=8.0 Hz, 1H), 7.62 (d, J=8.4 Hz, 1H), 7.49 (d, J=8.0 Hz, 2H), 7.42 (t, J=7.0 Hz, 1H), 7.22 (t, J=7.0 Hz, 1H), 6.72 (d, J=8.0 Hz, 2H).

LCMS; Mass Calcd.: 332; MS Found: 333 [MS+1].

Experimental Example 1-36. Preparation of Compound 36 (4-amino-N'-(indoline-6-carbonyl)benzenesulfonohydrazide)

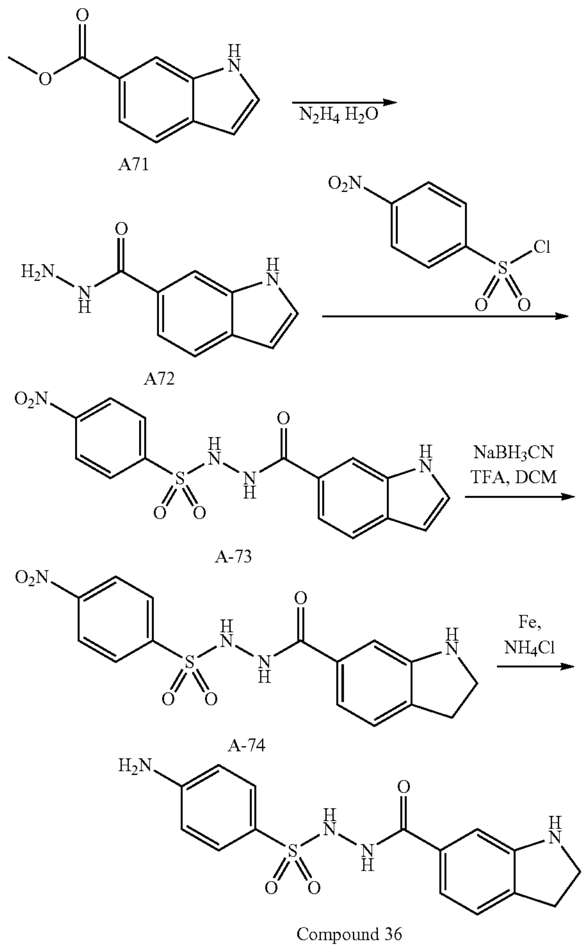

A71

A72

A-73

A-74

Compound 36

Step 1) Synthesis of A72

A mixture of A71 (methyl 1H indole-6-carboxylate, 500 mg, 2.86 mmol, 1.0 eq) and hydrazine monohydrate (10 mg) was stirred at 100° C. for 3 hrs. Then the mixture was cooled to 0° C. and filtered. The filter cake was washed with ice water and dried in vacuo to give A72 (1H-indole-6-carbohydrazide, 300 mg, yield 60.0%) as a white solid.

LCMS; Mass Calcd.: 175.18; MS Found: 176.0 [MS+1].

Step 2) Synthesis of A73

To a mixture of A72 (300 mg, 1.71 mmol, 1.0 eq) in pyridine (5 mL) and the 4-nitrobenzenesulfonyl chloride (380 mg, 1.71 mmol, 1.0 eq) was added at 0° C. Then the mixture was stirred at 10° C. for 3 hrs. The above solution was poured into water (30 mL) and extracted with EA (30 mL×3). The combined organic layers were washed with 1N HCl (30 mL×2) and brine, dried over $Na_2SO_4$ and concentrated to give crude product, which was purified by flash column (DCM/MeOH=50/1~30/1) to give A73 (N'-(1H-indole-6-carbonyl)-4-nitrobenzenesulfonohydrazide, 500 mg, yield 81.0%) as a yellow solid.

LCMS; Mass Calcd.: 360.34; MS Found: 361.1 [MS+1].

Step 3) Synthesis of A74

To a mixture of A73 (400 mg, 1.11 mmol, 1.0 eq) in DCM (15 mL) and TFA (5 mL) was added $NaBH_3CN$ (209 mg, 3.33 mmol, 3.0 eq) at 0° C. Then the mixture was stirred at 15° C. for 1 hr. The above solution was poured into ice water (30 mL) and adjusted pH=7~8 with sat. aq. $NaHCO_3$. The above solution was filtered and the filter cake was washed with PE and dried to give A74 (N'-(indoline-6-carbonyl)-4-nitrobenzenesulfonohydrazide, 200 mg crude) as a yellow solid.

LCMS; Mass Calcd.: 362.36; MS Found: 363.1 [MS+1].

Step 3) Synthesis of Compound 36

A mixture of A74 (200 mg, 0.55 mmol, 1.0 eq), $NH_4Cl$ (146 mg, 2.75 mmol, 5.0 eq), Fe (154 mg, 2.75 mmol, 5.0 eq) in $H_2O$ (10 mL) and EtOH (20 mL) was stirred at 85° C. for 2 hrs. The mixture was filtered and the filtrate was extracted with EA (20 mL×3). The combined organic layers were washed with brine, dried over $Na_2SO_4$ and concentrated. The crude product was recrystallized with methanol, the solid was lyophilized to give compound 36 (4-amino-N'-(indoline-6-carbonyl)benzenesulfonohydrazide, 60 mg, 32.7%) as a white solid.

1HNMR (DMSO-$d_6$, 400 MHz): δ 10.32 (s, 1H), 9.14 (s, 1H), 7.40 (d, J=8.4 Hz, 2H), 7.02 (d, J=7.6 Hz, 1H), 6.87 (d, J=7.2 Hz, 1H), 6.75 (s, 1H), 6.49 (d, J=8.4 Hz, 2H), 5.95 (s, 2H), 5.67 (s, 1H), 3.41 (t, J=8.2 Hz, 2H), 2.91 (t, J=8.6 Hz, 2H).

LCMS; Mass Calcd.: 332; MS Found: 333 [M+1].

Experimental Example 1-37. Preparation of Compound 37 (4-amino-N'-(indoline-3-carbonyl)benzenesulfonohydrazide)

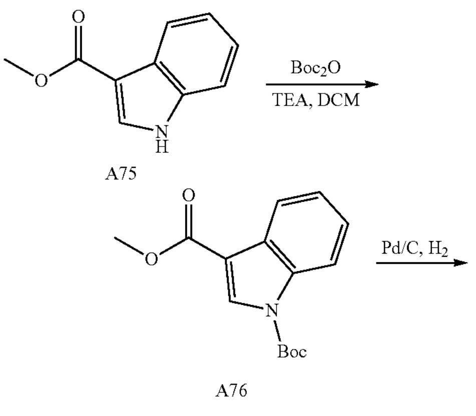

A75

A76

-continued

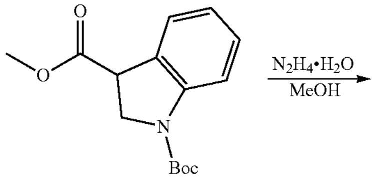

A77

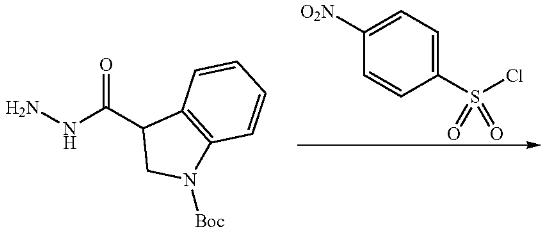

A78

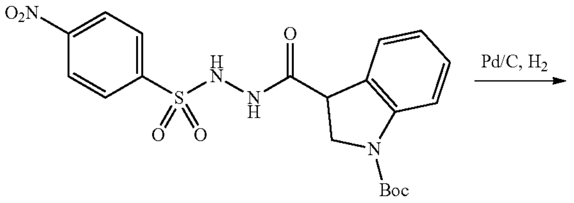

A79

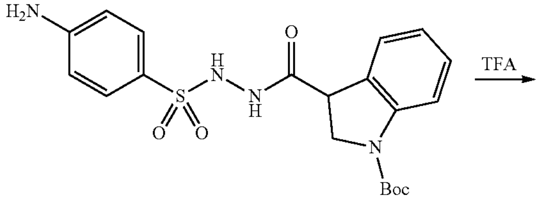

A80

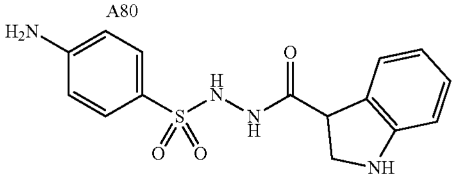

Compound 37

Step 1) Synthesis of A76

To a mixture of A75 (methyl 1H-indole-3-carboxylate, 1.00 g, 5.71 mmol, 1.0 eq) and triethylamine (TEA, 1.16 g, 11.4 mmol, 2.0 eq) in DCM (10 mL) was added $Boc_2O$ (1.37 g, 6.28 mmol, 1.1 eq) dropwise at 20° C. Then the mixture was stirred at 20° C. for 12 hrs. The above solution was poured into water (60 mL) and extracted with DCM (60 mL×3). The combined organic layers were washed with brine, dried over $Na_2SO_4$ and concentrated to give A76 (1-(tert-butyl) 3-methyl 1H-indole-1,3-dicarboxylate, 1.20 g, crude) as a yellow solid.

Step 2) Synthesis of A77

To a mixture of A76 (1.20 g, 4.36 mmol, 1.0 eq) in ethylacetate (EA, 30 mL) was added Pd/C (0.65 g) and degassed. Then the mixture was stirred at 60° C. for 12 hrs under $H_2$ (50 psi). The above solution was filtered and the filtrate was concentrated to give crude product. The crude product purified by silica gel (PE/EA=30:1~15:1) to afford A77 (1-(tert-butyl) 3-methyl indoline-1,3-dicarboxylate, 0.80 g, yield 66.2%) as a white solid.

Step 3) Synthesis of A78

To a mixture of A77 (800 mg, 2.89 mmol, 1.0 eq) in MeOH (20 mL) was added $N_2H_4 \cdot H_2O$ (1.6 mL). Then the mixture was stirred at 80° C. for 4 hrs. The reaction mixture was concentrated to give A78 (tert-butyl 3-(hydrazinecarbonyl)indoline-1-carboxylate 700 mg, yield 87.5%) as a white solid.

Step 3) Synthesis of A79

To a mixture of A78 (tert-butyl 3-(hydrazinecarbonyl) indoline-1-carboxylate, 300 mg, 1.08 mmol, 1.0 eq) in pyridine (5 mL) was added 4-nitrobenzene-1-sulfonyl chloride (0.24 g, 1.08 mmol, 1.0 eq) in portions. Then the mixture was stirred at 10° C. for 4 hrs. The above solution was poured into water (100 mL) and extracted with EA (100 mL×3). The combined organic layers were washed with brine, dried over $Na_2SO_4$ and concentrated to give A79 (tert-butyl 3-(2-((4-nitrophenyl)sulfonyl)hydrazine-1-carbonyl)indoline-1-carboxylate, 200 mg, yield 39.7%) as a yellow solid.

Step 4) Synthesis of A80

To a mixture of A79 (200 mg, 0.43 mmol, 1.0 eq) in EA (10 mL) was added Pd/C (50 mg). Then the mixture was stirred at 10° C. for 12 hrs under $H_2$ balloon. The above solution was filtered and the filtrate was concentrated to give A80 (tert-butyl 3-(2-((4-aminophenyl)sulfonyl)hydrazine-1-carbonyl)indoline-1-carboxylate, 200 mg, yield: 100%) as a yellow solid.

Step 5) Synthesis of Compound 37(4-amino-N'-(indoline-3-carbonyl)benzenesulfonohydrazide)

To a mixture of A80 (200 mg, 0.463 mmol, 1.0 eq) in DCM (5 mL) was added trifluoroacetic acid (TFA, 1 mL). Then the mixture was stirred at 10° C. for 2 hrs. The above solution was concentrated, the residue was added $H_2O$ (5 mL) and adjusted pH=9-10 with aq. $K_2CO_3$. The solution was extracted with EA (20 mL×3). The combined organic layers were washed with brine, dried over $Na_2SO_4$ and concentrated to give crude product. The crude product was purified by Prep-HPLC and lyophilized to give compound 37 (4-amino-N'-(indoline-3-carbonyl)benzenesulfonohydrazide, 30.0 mg, yield 19.6%) as an off white solid. 1HNMR ($DMSO\_d_6$, 400 MHz): δ 7.45 (d, J=8.4 Hz, 2H), 6.91-6.95 (m, 2H), 6.48-6.59 (m, 4H), 5.72 (s, 2H), 5.23 (s, 1H), 3.93 (br s, 1H), 3.49 (d, J=9.2 Hz, 2H).

LCMS; MS Found: 333.1 [MS+1].

Experimental Example 1-38. Preparation of Compound 38 (N'-(4-hydroxybenzoyl)piperidine-4-sulfonohydrazide)

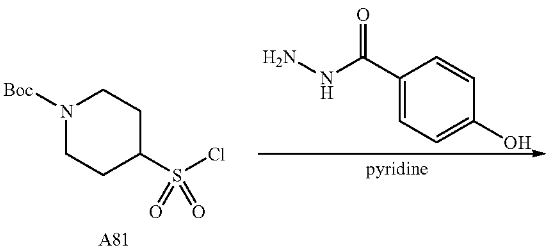

A81

-continued

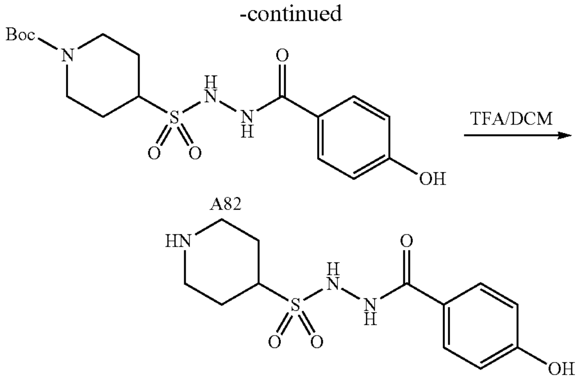

A82

Compound 38

Step 1) Synthesis of A82

To a mixture of 4-hydroxybenzohydrazide (A2, 268 mg, 1.77 mmol, 1.0 eq) in pyridine (2 mL) was added dropwise a solution of A81 (tert-butyl 4-(chlorosulfonyl)piperidine-1-carboxylate, 500 mg, 1.77 mmol, 1.0 eq) in pyridine (1 mL) at 0° C. The mixture was stirred at r.t. for 5 hrs. The above solution was filtered. The filtrate was concentrated and purified by column chromatography (DCM/MeOH=100:1-10:1) to give A82 (tert-butyl 4-((2-(4-hydroxybenzoyl)hydrazinyl)sulfonyl)piperidine-1-carboxylate, 300 mg, yield 42%) as a yellow solid.

1HNMR ($CDCl_3$, 400 MHz): δ 8.47 (br s, 1H), 7.70 (d, J=8.8 Hz, 2H), 7.30 (br s, 1H), 6.87 (d, J=8.4 Hz, 2H), 3.15-3.18 (m, 1H), 2.67-2.71 (m, 2H), 2.25 (d, J=10.8 Hz, 2H), 1.72-1.78 (m, 2H), 1.61-1.63 (m, 2H), 1.45 (s, 9H).

Step 2) Synthesis of Compound 38 (N'-(4-hydroxybenzoyl)piperidine-4-sulfonohydrazide)

To a mixture of A82 (300 mg, 0.75 mmol, 1.0 eq) in DCM (5 mL) was added TFA (1.5 mL) at 0° C. The mixture was stirred at r.t. for 4 hrs. The above solution was concentrated and purified by prep-HPLC and lyophilized to give compound 38 (N'-(4-hydroxybenzoyl)piperidine-4-sulfonohydrazide, 50 mg, yield 22%) as a yellow solid.

1HNMR (DMSO-$d_6$, 400 MHz): δ 10.40 (br s, 1H), 8.34 (s, 1H), 7.75 (d, J=8.4 Hz, 2H), 6.83 (d, J=8.8 Hz, 2H), 3.17-3.24 (m, 3H), 2.69 (t, J=12.0 Hz, 2H), 2.28 (d, J=12.0 Hz, 2H), 1.64-1.74 (m, 2H).

LCMS; Mass Calcd.: 299; MS Found: 300 [Ms+1].

Experimental Example 1-39. Preparation of Compound 39 (4-amino-N'-(indoline-6-carbonyl)-3-morpholinobenzenesulfonohydrazide)

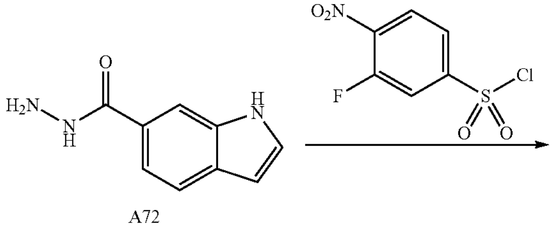

A72

-continued

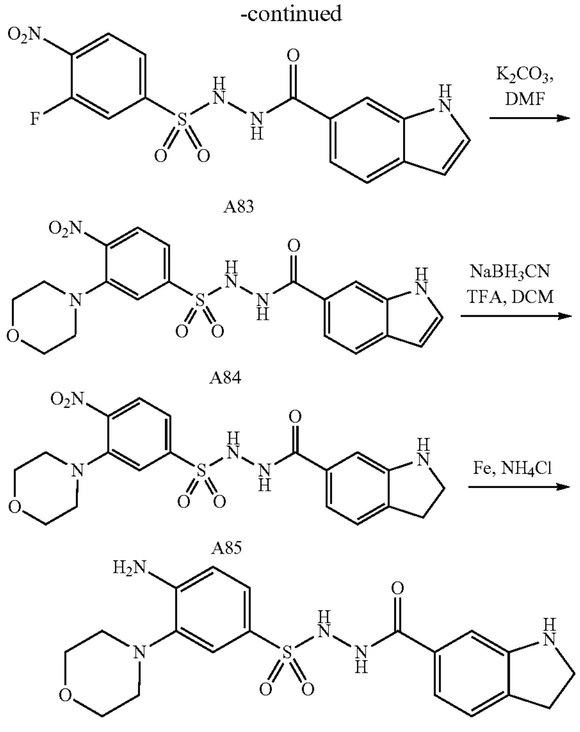

A83

A84

A85

Compound 39

Step 1) Synthesis of A83

To a mixture of A72 (1H-indole-6-carbohydrazide, 500 mg, 2.86 mmol, 1.0 eq) in pyridine (5 mL) was added 3-fluoro-4-nitrobenzene-1-sulfonyl chloride (686 mg, 2.86 mmol, 1.0 eq) in pyridine (2 mL) dropwise 0° C. Then the mixture was stirred at 10° C. for 3 hrs. The above solution was concentrated to give crude product, which was purified by column (DCM:MeOH=50:1-20:1) to give A83 (3-fluoro-N'-(1H-indole-6-carbonyl)-4-nitrobenzenesulfonohydrazide, 700 mg, yield: 64.8%) as a yellow solid.

LCMS; Mass Calcd.: 378.3; MS Found: 379.1 [Ms+1].

Step 2) Synthesis of A84

To a mixture of A83 (700 mg, 1.85 mmol, 1.0 eq) and $K_2CO_3$ (640 mg, 4.64 mmol, 2.5 eq) in DMF (7 mL) was added morpholine (193 mg, 2.22 mmol, 1.2 eq) at 10° C. Then the mixture was stirred at 25° C. for 16 hrs. The above solution was poured into water (30 mL) and extracted with EA (30 mL×3). The combined organic layers were washed brine, dried over $Na_2SO_4$ and concentrated to give A84 (N'-(1H-indole-6-carbonyl)-3-morpholino-4-nitrobenzenesulfonohydrazide, 600 mg, yield: 72.8%) as a yellow solid.

LCMS; Mass Calcd.: 445.4; MS Found: 446.1 [Ms+1].

Step 3) Synthesis of A85

To a mixture of A84 (600 mg, 1.35 mmol, 1.0 eq) in DCM (5 mL) was added TFA (1 mL) and $NaBH_3CN$ (251 mg, 4.04 mmol, 3.0 eq) at 10° C. Then the mixture was stirred at 25° C. for 4 hrs. The above solution was poured into water (30 mL) and extracted with EA (30 mL×3). The combined organic layers were washed brine, dried over $Na_2SO_4$ and concentrated to give A85 (N'-(indoline-6-carbonyl)-3-morpholino-4-nitrobenzenesulfonohydrazide, 450 mg, crude) as a yellow solid.

LCMS; Mass Calcd.: 447.4; MS Found: 448.2 [Ms+1].

Step 4) Synthesis of Compound 39 (4-amino-N'-(indoline-6-carbonyl)-3-morpholinobenzenesulfonohydrazide)

To a mixture of A85 (450 mg, 1.01 mmol, 1.0 eq) in EtOH (5 mL) was added Fe (282 mg, 5.05 mmol, 5.0 eq) and sat. aq. $NH_4Cl$ (1 mL). Then the mixture was stirred at 85° C. for 3 hrs. The above solution concentrated, then DMSO (5 mL) was added and filtered. The filtrate was purified by prep-HPLC and lyophilized to give compound 39 (4-amino-N'-(indoline-6-carbonyl)-3-morpholinobenzenesulfonohydrazide, 30 mg, yield 7.0%) as an off-white solid. 1HNMR (DMSO-$d_6$, 400 MHz): δ 10.36 (d, J=4.4 Hz, 1H), 9.21 (d, J=4.4 Hz, 1H), 7.23-7.27 (m, 2H), 7.03 (d, J=7.6 Hz, 1H), 6.89 (d, J=7.6 Hz, 1H), 6.67 (s, 1H), 6.65 (d, J=8.4 Hz, 1H), 5.63 (br s, 2H), 3.69 (t, J=4.2 Hz, 4H), 3.42 (t, J=8.6 Hz, 2H), 2.91 (t, J=8.6 Hz, 2H), 2.63 (t, J=4.2 Hz, 4H).

LCMS; Mass Calcd.: 417.1; MS Found: 418.1 [MS+1].

Experimental Example 1-40. Preparation of Compound 40 (4-amino-N'-(piperazine-1-carbonyl)benzenesulfonohydrazide)

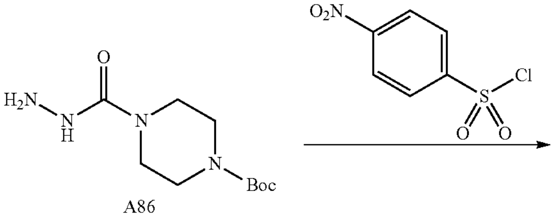

A86

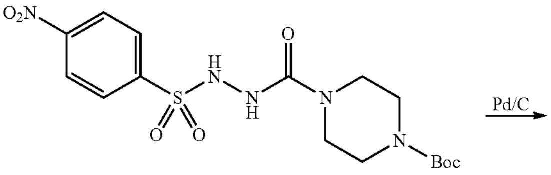

A87

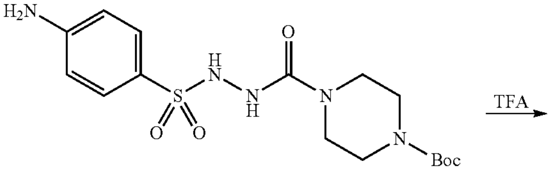

A88

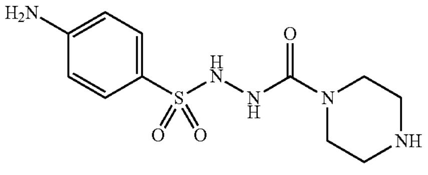

Compound 40

Step 1) Synthesis of A87

To a mixture of A86 (tert-butyl 4-(hydrazinecarbonyl) piperazine-1-carboxylate, 1.00 g, 4.09 mmol, 1.0 eq) in pyridine (10 mL) was added 4-nitrobenzene-1-sulfonyl chloride (906 mg, 4.09 mmol, 1.0 eq) in pyridine (5 mL) dropwise at 10° C. Then the mixture was stirred at 10° C. for 3 hrs. The above solution was poured into water (50 mL) and extracted with EA (50 mL×3). The combined organic layers were washed with 1N HCl (50 mL×2) and brine, dried over $Na_2SO_4$ and concentrated to give crude product. The crude product was washes with EA (5 mL), filtered and dried solid in vacuum to give A87 (tert-butyl 4-(2-((4-nitrophenyl) sulfonyl)hydrazine-1-carbonyl)piperazine-1-carboxylate, 800 mg, yield 45.5%) as a yellow solid.

1HNMR (DMSO-$d_6$, 400 MHz): δ 9.74 (s, 1H), 9.08 (s, 1H), 8.38 (d, J=8.0 Hz, 2H), 8.03 (d, J=8.4 Hz, 2H), 3.17 (br s, 8H), 1.40 (s, 9H).

Step 2) Synthesis of A88

To a mixture of A87 (400 mg, 0.93 mmol, 1.0 eq) in THF (10 mL) was added Pd/C (40 mg). Then the mixture was stirred at 10° C. for 16 hrs under $H_2$ balloon. The above solution was filtered and the filtrate was concentrated to give A88 (tert-butyl 4-(2-((4-aminophenyl)sulfonyl)hydrazine-1-carbonyl)piperazine-1-carboxylate, 350 mg, yield 94%) as a yellow solid.

Step 3) Synthesis of Compound 40 (4-amino-N'-(piperazine-1-carbonyl)benzenesulfonohydrazide)

To a mixture of A88 (150 mg, 0.37 mmol, 1.0 eq) in DCM (5 mL) was added TFA (1 mL). Then the mixture was stirred at 25° C. for 3 hrs. The above solution was concentrated to give crude product. The crude product was added MeOH (5 mL), added $K_2CO_3$ (62 mg, 0.45 mmol) and stirred at RT for 1 h. The solution was filtered and the solution was purified by prep-HPLC and lyophilized to give compound 40 (4-amino-N'-(piperazine-1-carbonyl)benzenesulfonohydrazide, 50 mg, yield 38.7%) as a white solid.

1HNMR (DMSO-$d_6$, 400 MHz): δ 8.80 (d, J=2.8 Hz, 1H), 8.28-8.32 (m, 3H), 7.38 (d, J=8.8 Hz, 2H), 6.56 (d, J=8.8 Hz, 2H), 5.98 (s, 2H), 3.22 (s, 4H), 2.69 (s, 4H).

LCMS; Mass Calcd.: 299; MS Found: 300 [MS+1].

Experimental Example 1-41. Preparation of Compound 41 (4-amino-3-morpholino-N'-(piperazine-1-carbonyl)benzenesulfonohydrazide)

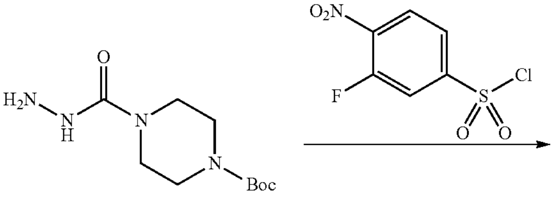

A86

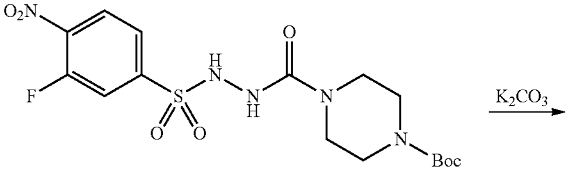

A89

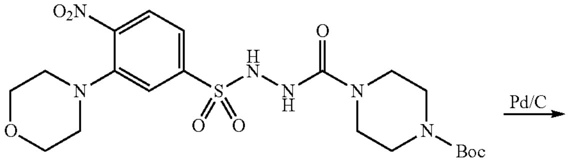

A90

-continued

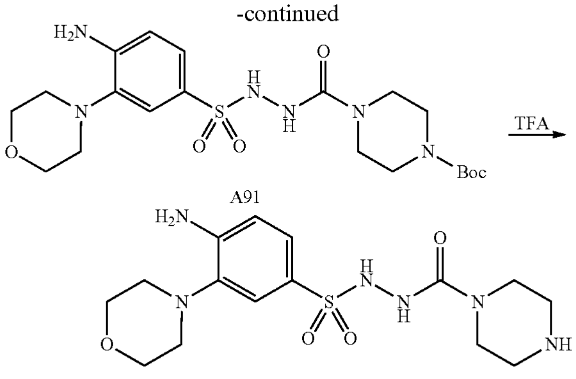

A91

Compound 41

Step 1) Synthesis of A89

To a mixture of A86 (1.50 g, 6.14 mmol, 1.0 eq) in pyridine (10 mL) was added 3-fluoro-4-nitrobenzene-1-sulfonyl chloride (1.46 g, 6.14 mmol, 1.0 eq) in pyridine (5 mL) dropwise. Then the mixture was stirred at 10° C. for 3 hrs. The above solution was poured into water (30 mL) and extracted with EA (30 mLx3). The combined organic layers were washed with 1N HCl (30 mLx2) and brine, dried over $Na_2SO_4$ and concentrated to give A89 (tert-butyl 4-(2-((3-fluoro-4-nitrophenyl)sulfonyl)hydrazine-1-carbonyl)piperazine-1-carboxylate, 1.5 g, crude) as a yellow solid.

Step 2) Synthesis of A90

To a mixture of A89 (1.50 g, 3.35 mmol, 1.0 eq) and $K_2CO_3$ (1.16 g, 8.37 mmol, 2.5 eq) in DMF (15 mL) was added morpholine (350 mg, 4.02 mmol, 1.2 eq) at 10° C. Then the mixture was stirred at 25° C. for 16 hrs. The above solution was poured into water (50 mL) and extracted with EA (30 mLx3). The combined organic layers were washed brine, dried over $Na_2SO_4$ and concentrated to give crude product, which was purified by column (DCM/MeOH=50/1-10/1) to give A90 (tert-butyl 4-(2-((3-morpholino-4-nitrophenyl)sulfonyl)hydrazine-1-carbonyl)piperazine-1-carboxylate, 700 mg, yield: 40.6%) as a yellow solid.

LCMS; Mass Calcd.: 514.55; MS Found: 516.2[MS+2].

Step 3) Synthesis of A91

To a mixture of A90 (700 mg, 1.36 mmol, 1.0 eq) in THF (10 mL) was added Pd/C (200 mg). Then the mixture was stirred at r.t for 15 min under $H_2$ (50 psi). The above solution was filtered and the filtrate was and concentrated to give A91 (tert-butyl 4-(2-((4-amino-3-morpholinophenyl)sulfonyl)hydrazine-1-carbonyl)piperazine-1-carboxylate, 300 mg, crude) as a yellow solid.

Step 4) Synthesis of Compound 41 (4-amino-3-morpholino-N'-(piperazine-1-carbonyl)benzenesulfonohydrazide)

To a mixture of A91 (200 mg, 0.41 mmol, 1.0 eq) in DCM (10 mL) was added TFA (2 mL). Then the mixture was stirred at r.t for 3 hrs. The mixture was concentrated and purified by prep-HPLC and lyophilized to give compound 41 (4-amino-3-morpholino-N'-(piperazine-1-carbonyl)benzenesulfonohydrazide, 20.0 mg, yield 12.6%) as a pink solid.

1HNMR (DMSO-$d_6$, 400 MHz): δ 8.92 (d, J=5.2 Hz, 1H), 8.69-8.75 (m, 2H), 7.23 (d, J=5.6 Hz, 2H), 6.70 (t, J=8.6 Hz, 1H), 5.68 (s, 2H), 3.78 (s, 4H), 3.39 (s, 4H), 2.98 (s, 4H), 2.76 (s, 4H).

LCMS; Mass Calcd.: 384; MS Found: 384.9 [MS+1].

Experimental Example 1-42. Preparation of Compound 42 (N'-(4-hydroxybenzoyl)-2-methylthiazole-4-sulfonohydrazide)

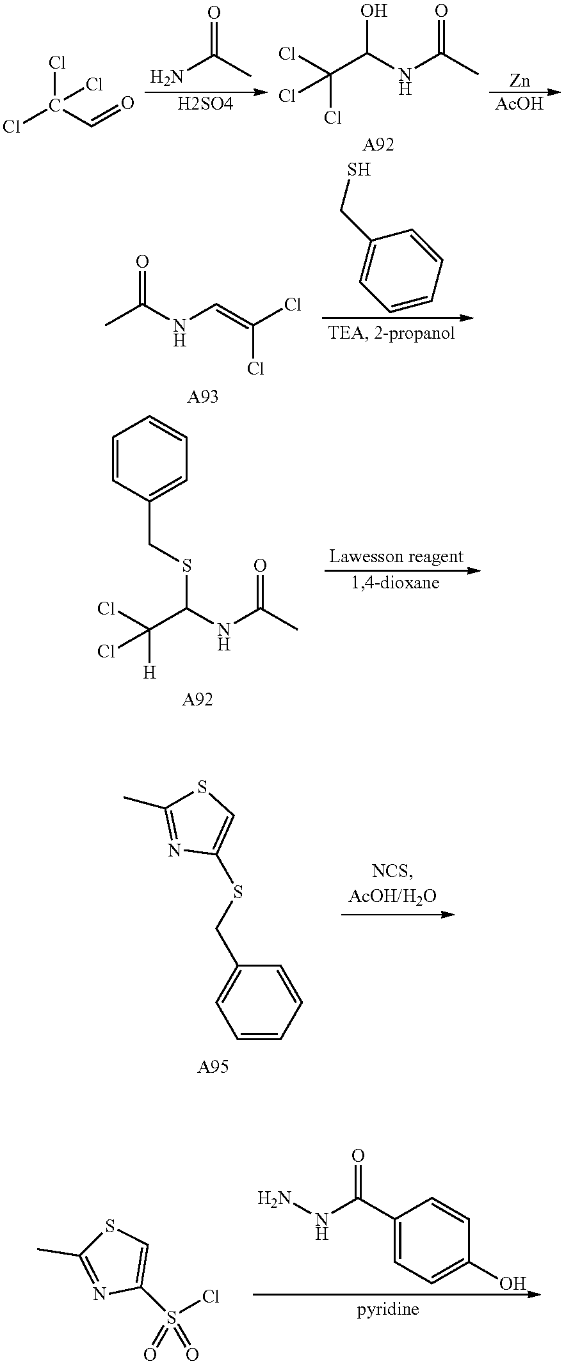

A92

A93

A92

A95

A56

-continued

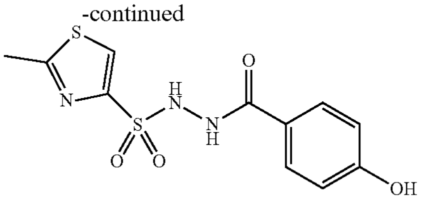

Compound 42

Step 1) Synthesis of A92

A stirred mixture of 2,2,2-trichloroacetaldehyde (20 g, 0.13 mmol), acetamide (7 g, 0.118 mmol), and concentrated sulfuric acid (1.2 g) was heated at 100° C. for 1 h. The reaction mixture crystallized upon cooling. The mixture was triturated with deionized water, filtered, washed with a large amount of water, and recrystallized from ethanol to give A92 (N-(2,2,2-trichloro-1-hydroxyethyl)acetamide, 15 g) as a white solid.

1HNMR (DMSO_$d_6$, 400 MHz): 8.72 (d, 1H), 7.64 (d, 1H), 5.74-5.70 (m, 1H), 1.92 (s, 3H).

Step 2) Synthesis of A93

Zinc dust (5 g, 78 mmol) was gradually added to a stirred suspension of A92 (8 g, 39 mmol) in glacial acetic acid (50 mL) over a period of 3 h. During the zinc addition the temperature of the reaction mixture was kept below 40° C. The reaction mixture was then stirred at room temperature for 24 h. Then the precipitated zinc salt was filtered off and washed with glacial acetic acid. The acetic acid was removed under reduced pressure. The solid residue was triturated with deionized water and recrystallized to give A93 (N-(2,2-dichlorovinyl)acetamide, 3 g) as a white solid.

1HNMR (DMSO_$d_6$, 400 MHz): 9.87 (d, 1H), 7.21 (d, 1H), 2.03 (s, 3H).

Step 3) Synthesis of A94

Benzylthiol (4 g, 32 mmol) and triethylamine (3.29 g, 32.6 mmol) were added to a stirred solution of A93 (2 g, 13 mmol) in 2-propanol (25 mL). The reaction mixture was stirred at room temperature for 48 h. Then the solvent was removed under reduced pressure and the residue was triturated with water, resulting in a crystalline solid. The crude product was purified by recrystallization from either 2-propanol or ethanol to give A94 (N-(1-(benzylthio)-2,2-dichloroethyl)acetamide, 2.5 g) as a white solid.

1HNMR (DMSO_$d_6$, 400 MHz): 8.72 (d, 1H), 7.23-7.25 (m, 5H), 6.42 (d, 1H), 5.40 (dd, 1H), 3.87 (q, 2H), 1.93 (S, 3H).

Step 4) Synthesis of A95

Lawesson reagent (7.6 g, 18.8 mmol) was added to a stirred solution of A94 (5 mmol) in toluene (30 mL). The reaction mixture was refluxed for 8 h, and then the solvent was removed under reduced pressure. The residue was triturated with 10% aqueous NaOH, adjusting to pH 9. The raw product was filtered, dried, and recrystallized from 2-propanol. Liquid products were extracted with dichloromethane to give A95 (4-(benzylthio)-2-methylthiazole, crude, 2.5 g) as a yellow oil.

1HNMR (DMSO_$d_6$, 400 MHz): 7.44 (s, 1H), 7.30-7.20 (m, 5H), 4.04 (s, 2H), 2.59 (S, 3H).

Step 5) Synthesis of A96

To a solution of A95 (crude, 1 g) in acetic acid (10 ml) was added NCS (3 g) and water (2 mL) at 0° C. The reaction mixture was stirred at room temperature overnight. The reaction mixture was triturated with 10% aqueous $NaHCO_3$ adjusting to pH=8, extracted with DCM (30 mL*3). The combined organic layers were washed with brine, dried over $Na_2SO_4$ and concentrated to give crude product. The residue was purified by passing a silica gel to give A96 (2-methylthiazole-4-sulfonyl chloride, 100 mg) as yellow oil.

1HNMR ($CDCl_3$, 400 MHz): 8.33 (s, 1H), 2.86 (S, 3H).

Step 6) Synthesis of Compound 42 (N'-(4-hydroxybenzoyl)-2-methylthiazole-4-sulfonohydrazide)

A mixture of A96 (100 mg, 0.5 mmol) and A2 (4-hydroxybenzohydrazide, 80 mg, 0.5 mmol) in Pyridine (20 mL) was stirred at 80° C. overnight. The above solution was poured into water (30 mL) and extracted with EA (30 mL*3). The combined organic layers were washed brine, dried over $Na_2SO_4$ and concentrated to give crude product. The residue was purified by prep-HPLC to give compound 42 (N'-(4-hydroxybenzoyl)-2-methylthiazole-4-sulfonohydrazide, 30 mg) as off white solid.

1HNMR (DMSO-$d_6$, 400 MHz): 10.53 (s, 1H), 10.27 (s, 1H), 10.13 (s, 1H), 8.02 (s, 1H), 7.63 (d, 2H), 6.80 (d, 2H), 2.70 (s, 3H).

LCMS; Mass Calcd.: 313.3; MS Found: 314.0 [MS+1].

Experimental Example 1-43. Preparation of Compound 43 ((1S,4S)-4-amino-N'-(4-hydroxybenzoyl)cyclohexane-1-sulfonohydrazide)

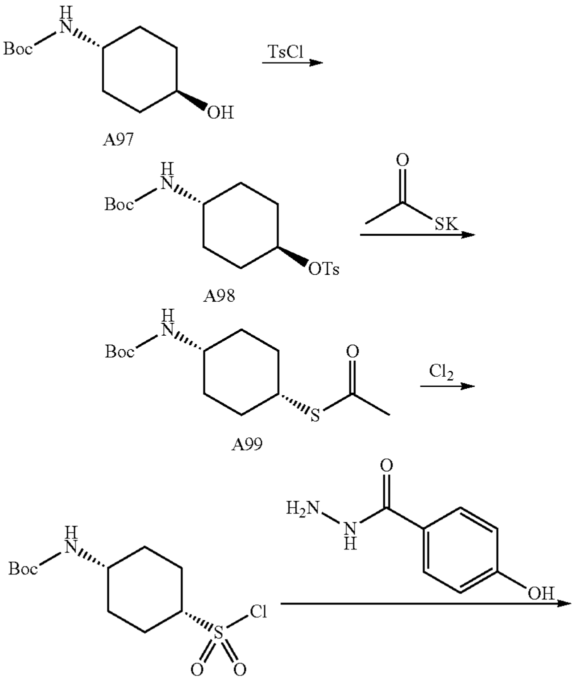

A97 A98 A99 A100

-continued

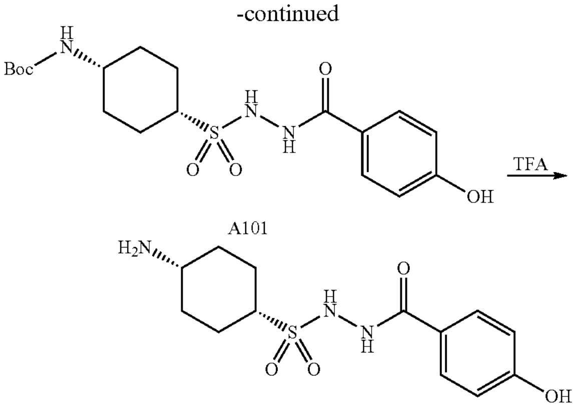

A101

Compound 43

Step 1) Synthesis of A98

To a mixture of A97 (tert-butyl ((1 r,4r)-4-hydroxycyclohexyl)carbamate, 27 g, 126 mmol, 1.0 eq) in pyridine (100 mL) was added 4-methylbenzenesulfonyl chloride (28.6 g, 151 mmol, 1.2 eq) in portions, the mixture was stirred at r.t. overnight. Pyridine was removed in vacuo, the residue was purified by column chromatography on silica gel to give A98 ((1 r,4r)-4-((tert-butoxycarbonyl)amino)cyclohexyl 4-methylbenzenesulfonate, 40 g, 86.4%) as white solid.

Step 2) Synthesis of A99

A solution of A98 (10.0 g, 27.1 mmol, 1.0 eq) in DMF (100 mL) was treated with potassium thioacetate (9.3 g, 81.3 mmol, 3.0 eq) and the reaction mixture stirred at 60° C. under nitrogen for 4 h. The reaction mixture was quenched with brine (200 mL) and extracted with EtOAc (100 mL*2). The combined organics were dried and concentrated under reduced pressure, the crude product was purified by column chromatography on silica gel to give A99 (S-((1 s,4s)-4-((tert-butoxycarbonyl)amino)cyclohexyl)ethanethioate, 3.0 g, 40.5%) as white solid.

Step 3) Synthesis of A100

To a solution of A99 (2.50 g, 9.16 mmol, 1.0 eq) in DCM (30 mL) and water (30 mL) was bubbled chlorine gas at 0° C. for 30 min. The two layers were separated, the DCM layer was washed with aq. sodium thiosulfate and brine, dried over sodium sulfate, filtered and concentrated to give crude A100 (tert-butyl ((1s,4s)-4-(chlorosulfonyl)cyclohexyl)carbamate) as brown solid.

Step 4) Synthesis of A101

A solution of 4-hydroxybenzohydrazide (A2, 2.76 g, 18.2 mmol, 2.0 eq) in pyridine (10 mL) was added a solution of A100 (crude) in DCM (5 mL) dropwise, the mixture was stirred at room temperature for 2 hours. The solvent was removed in vacuo and the crude product was purified by column chromatography on silica gel to give A101 (tert-butyl ((1 s,4s)-4-((2-(4-hydroxybenzoyl)hydrazinyl)sulfonyl)cyclohexyl)carbamate, 0.2 g, 5.3% for 2 steps) as white solid.

Step 5) Synthesis of Compound 43 ((1 s,4s)-4-amino-N'-(4-hydroxybenzoyl)cyclohexane-1-sulfonohydrazide)

A101 (200 mg, 4.2 mmol, 1.0 eq) was dissolved in a mixture of TFA (1 mL) and DCM (5 mL), stirred for 2 hours. The mixture was concentrated in vacuo and dissolved in MeOH, $NH_3$/MeOH was added to pH=9, the solvent was concentrated in vacuo, the reside was dissolved in MeOH, purified by prep-HPLC and freeze dried to give compound 43 ((1 s,4s)-4-amino-N'-(4-hydroxybenzoyl)cyclohexane-1-sulfonohydrazide, 20 mg, 13.2%) as yellow solid.

1HNMR (CD3OD, 400 MHz): δ 7.749 (d, J=8.8 Hz, 2H), 6.862 (d, J=8.4 Hz, 2H), 3.286-3.331 (m, 2H), 2.315-2.350 (m, 2H), 1.995-2.153 (m, 4H), 1.855-1.918 (m, 2H).

LCMS; MS Calcd.: 313.11; MS Found: 313.9 ([M+1]+).

Experimental Example 1-44. Preparation of Compound 44 ((1R,4R)-4-amino-N'-(4-hydroxybenzoyl)cyclohexane-1-sulfonohydrazide)

Compound 44 was synthesized as white solid (26.7% yield) in the same manner as in Experimental Example 1-45 by using tert-butyl ((1s,4s)-4-hydroxycyclohexyl)carbamate as a starting material instead of A97.

1HNMR (CD3OD, 400 MHz): δ 7.750 (d, J=8.8 Hz, 2H), 6.868 (d, J=8.4 Ha, 2H), 3.042-3.174 (m, 2H), 2.567 (d, J=12.4 Hz, 2H), 2.180 (d, J=12.4 Hz, 2H), 1.680-1.784 (m, 2H), 1.410-1.514 (m, 2H).

LCMS; MS Calcd.: 313.11; MS Found: 313.9 ([M+1]+).

Experimental Example 1-45. Preparation of Compound 45 (4-((2-(4-hydroxybenzoyl)hydrazinyl)sulfonyl)-5-methylfuran-2-carboxylic acid)

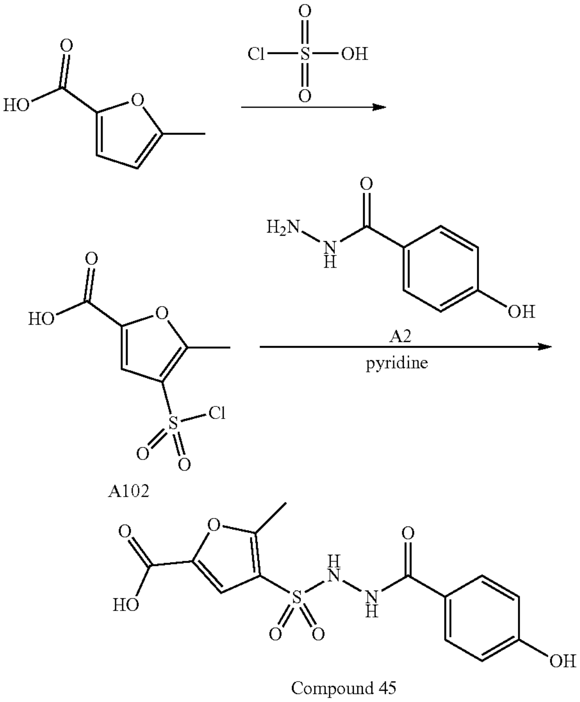

A102

Compound 45

Step 1) Synthesis of A102

A stirred mixture of 5-methylfuran-2-carboxylic acid (10 g, 80 mmol), chlorosulfonic acid (30 mL) was stirred at 50° C. for 3 h before quenching with ice-water. The aqueous layer was extracted with DCM, and the combined organic extracts were washed with brine, dried over anhydrous sodium sulfate, and concentrated in vacuo to give compound A102 (14 g) as a yellow solid.

1HNMR (DMSO_$d_6$, 400 MHz): 13.95 (s, 1H), 6.97 (s, 1H), 2.50 (s, 3H).

Step 2) Synthesis of Compound 45 (4-((2-(4-hydroxybenzoyl)hydrazinyl)sulfonyl)-5-methylfuran-2-carboxylic acid)

A mixture of Compound A102 (5 g, 22.3 mmol) and Compound A2 (3.4 g, 22.3 mmol) in Pyridine (50 mL) was stirred at 60° C. overnight. The above solution was poured into water (30 mL) and extracted with EA (30 mL*3). The combined organic layers were washed brine, dried over $Na_2SO_4$ and concentrated to give crude product. The residue was purified by prep-HPLC to give compound 45 (4-((2-(4-hydroxybenzoyl)hydrazinyl)sulfonyl)-5-methylfuran-2-carboxylic acid, 1.3 g) as yellow solid.

1HNMR (DMSO-$d_6$, 400 MHz): 13.5 (brs, 1H), 10.47 (s, 1H), 10.14 (s, 1H), 10.03 (s, 1H), 7.63 (d, 2H), 7.18 (s, 1H), 6.79 (s, 2H), 3.17 (s, 3H)

Experimental Example 1-46. Preparation of Compound 46 (N'-(4-hydroxybenzoyl)pyrrolidine-3-sulfonohydrazide)

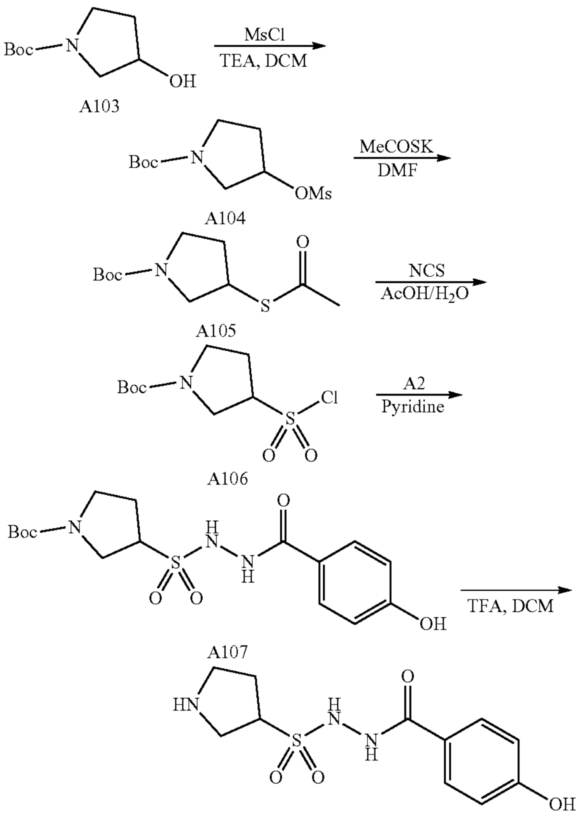

A103
A104
A105
A106
A107
Compound 46

Step 1) Synthesis of A104

To a stirred solution of A103 (5.00 g, 26.7 mmol, 1.0 eq) and TEA (5.40 g, 53.4 mmol, 2.0 eq) in DCM (50 mL) was added dropwise methane sulfonyl chloride (4.59 g, 40.1 mmol, 1.5 eq) at 0° C. The mixture was stirred at r.t. for 2 hrs. The mixture was quenched by $H_2O$ (100 mL) and extracted with DCM (100 mL×2). The combined organic layers were washed with brine (100 mL), dried, concentrated. The residue was purified by column chromatography (PE/EA=100:1-10:1) to give A104 (5.0 g, yield 70.6%) as yellow oil. (PE/EA=10:1, Rf=0.6)

Step 2) Synthesis of A105

A mixture of A104 (5.00 g, 18.9 mmol, 1.0 eq) and potassium thioacetate (4.30 g, 37.7 mmol, 2.0 eq) in DMF (50 mL) was stirred at 70° C. for 16 hrs. The mixture was treated with $H_2O$ (200 mL) and extracted with EA (200 mL×2). The combined organic layers were washed with $H_2O$ (100 mL×3), brine (100 mL), dried, concentrated. The residue was purified by column chromatography (PE/EA=50:1-5:1) to give A105 (2.0 g, yield 43.4%) as a brown solid.

Step 3) Synthesis of A106

To a stirred solution of A105 (2.00 g, 8.16 mmol, 1.0 eq) in acetic acid (AcOH 30 mL) and $H_2O$ (30 mL) was added N-chlorosuccinimide (5.45 g, 40.8 mmol, 5.0 eq). The mixture was stirred at r.t. for 16 hrs. The mixture was concentrated and purified by column chromatography (PE/EA=50:1-1:1) to give A106 (1.0 g, yield 45.6%) as yellow oil. (PE/EA=3:1, Rf=0.5)

1HNMR (CDCl3, 400 MHz): δ 4.28-4.31 (m, 1H), 4.00-4.02 (m, 1H), 3.85-3.95 (m, 1H), 3.66-3.75 (m, 1H), 3.52-3.58 (m, 1H), 2.63 (br s, 1H), 2.44-2.54 (m, 1H), 1.49 (s, 9H).

Step 4) Synthesis of A107

To a stirred solution of 4-hydroxybenzohydrazide (0.56 g, 3.71 mmol, 1.0 eq) in pyridinium (30 mL) was added dropwise a solution of A106 (1.00 g, 3.71 mmol, 1.0 eq) in pyridinium (10 mL) at 0° C. The mixture was stirred at r.t. for 6 hrs. The mixture was concentrated and purified by column chromatography (DCM/MeOH=100:1-10:1) to give A107 (0.50 g, yield 34.9%) as yellow oil. (DCM/MeOH=10:1, Rf=0.4)

Step 5) Synthesis of Compound 46 (N'-(4-hydroxybenzoyl)pyrrolidine-3-sulfonohydrazide)

To a mixture of A107 (500 mg, 1.30 mmol, 1.0 eq) in DCM (10 mL) was added TFA (4 mL) at 0° C. The mixture was stirred at r.t. for 4 hrs. The above solution was concentrated and purified by prep-HPLC and lyophilized to give compound 46 (N'-(4-hydroxybenzoyl)pyrrolidine-3-sulfonohydrazide, 30 mg, yield 7.0%) as a light yellow solid. (TLC: N/A)

1HNMR (DMSO-$d_6$, 400 MHz): δ 10.47 (br s, 2H), 8.25 (s, 1H), 7.75 (d, J=8.4 Hz, 2H), 6.83 (d, J=8.8 Hz, 2H), 3.67-3.72 (m, 1H), 3.19-3.21 (m, 2H), 2.89-2.91 (m, 1H), 2.83-2.85 (m, 1H), 2.07-2.10 (m, 2H).

Experimental Example 1-47. Preparation of Compound 47 (N'-(4-hydroxybenzoyl)-1H-pyrrolo[2,3-b]pyridine-2-sulfonohydrazide)

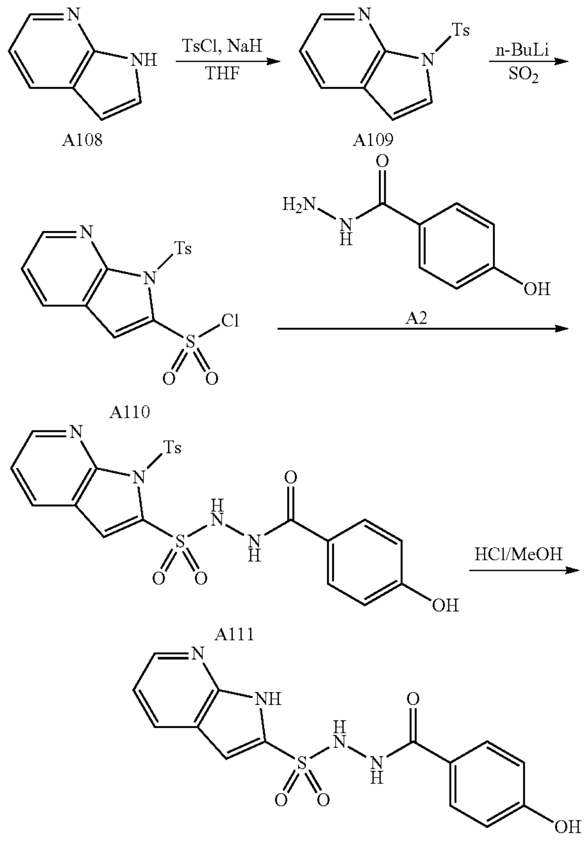

A108 A109 A110 A111

Compound 47

Step 1) Synthesis of A109

To a mixture of 1H-pyrrolo[2,3-b]pyridine (A108, 6.00 g, 50.8 mmol, 1.0 eq) in THF (60 mL) was added NaH (2.44 g (60% w/w), 60.9 mmol, 1.2 eq) at 0° C. and stirred for 1 hr at 0° C. Then the solution was added TsCl (9.65 g, 50.8 mmol, 1.0 eq) in THF (20 mL) dropwise. The solution was stirred for 16 hrs. The above solution was poured into water (200 mL) and extracted with EA (100 mL×3). The combined organic layers were dried over $Na_2SO_4$ and concentrated to give crude product, which was washed with PE (30 mL) for 1 hr, filtered and collected solid. The solid was dried in vacuo to give A109 (11.0 g, yield 79.5%) as a white solid. (TLC: N/A)

*LCMS; Mass Calcd.: 272.32; MS Found: 273.1 [MS+1].

Step 2) Synthesis of A110

To a mixture of A109 (2.00 g, 7.35 mmol, 1.0 eq) in THF (20 mL) was added n-BuLi (3.24 mL, 8.08 mmol, 1.1 eq) dropwise at −76° C. The mixture was stirred at −76° C. for 1 hr. Then the mixture was stirred at −76° C. to 10° C. for 1 hr under $SO_2$ balloon and the solution was concentrated. The residue in DCM (30 mL) was added NCS (1.58 g, 11.7 mmol, 1.6 eq) at 20° C., then the mixture was stirred at 20° C. for 1 hr. The above solution was poured into water (50 mL) and extracted with DCM (50 mL×3). The combined organic layers were dried over $Na_2SO_4$ and concentrated to give A110 (1.30 g, yield 47.8%) as a yellow solid. LCMS; Mass Calcd.: 370.82; MS Found: 371.0 [MS+1].

Step 3) Synthesis of A111

To a mixture of A110 (1.30 g, 3.51 mmol, 1.0 eq) in pyridine (10 mL) was added 4-hydroxybenzohydrazide (A2, 587 mg, 3.86 mmol, 1.1 eq) in pyridine (5 mL) dropwise at 10° C. Then the mixture was stirred at 10° C. for 3 hrs. The above solution was poured into water (50 mL) and extracted with EA (50 mL×3). The combined organic layers were washed with 1N HCl (50 mL×2) and brine (50 mL), dried over $Na_2SO_4$ and concentrated to give crude product. The crude product was washes with EA (5 mL), filtered and dried solid in vacuum to give A111 (600 mg, yield 35.3%) as a yellow solid. (TLC: N/A)

LCMS; Mass Calcd.: 486.51; MS Found: 487.1 [MS+1].

Step 4) Synthesis of Compound 47 (N'-(4-hydroxybenzoyl)-1H-pyrrolo[2,3-b]pyridine-2-sulfonohydrazide)

To a mixture of A111 (350 mg, 0.71 mmol, 1.0 eq) in MeOH (6 mL) was added con. HCl (2 mL). Then the mixture was stirred at 60° C. for 3 hrs. The above solution was concentrated, and the crude product was purified by prep-HPLC and lyophilized to give compound 47 (N'-(4-hydroxybenzoyl)-1H-pyrrolo[2,3-b]pyridine-2-sulfonohydrazide, 20 mg, yield 8.36%) as a white solid. (TLC: N/A)

1HNMR (DMSO-$d_6$, 400 MHz): δ 12.61 (s, 1H), 10.45 (s, 1H), 10.11 (br s, 1H), 9.90 (d, J=2 Hz, 1H), 8.40-8.42 (m, 1H), 8.08-8.10 (m, 1H), 7.62 (d, J=8.8 Hz, 2H), 7.16-7.19 (m, 1H), 7.13 (s, 1H), 6.77 (d, J=8.8 Hz, 2H).

LCMS; Mass Calcd.: 332; MS Found: 333 [MS+1].

Experimental Example 1-48. Preparation of Compound 48 (4-hydroxy-N'-(4-methoxybenzyl)benzohydrazide)

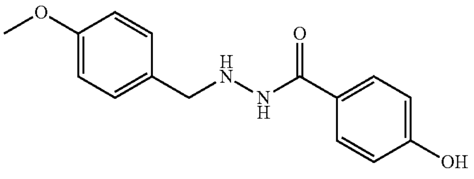 [SMILES: COc1ccc(CNNC(=O)c2ccc(O)cc2)cc1]

Compound 48 is obtained by the same preparation method as in Experimental Example 1-19 using 1-(bromomethyl)-4-methoxybenzene instead of 1-(bromomethyl)-4-nitrobenzene.

Experimental Example 1-49. Preparation of Compound 49 (N'-(4-aminobenzyl)-2,3-dihydro-1H-indene-2-carbohydrazide)

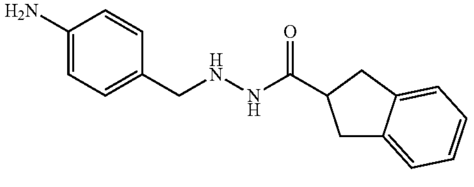 [SMILES: Nc1ccc(CNNC(=O)C2Cc3ccccc3C2)cc1]

Compound 49 is obtained by the same preparation method as in Experimental Example 1-19 using A60 (2,3-dihydro-1H-indene-2-carbohydrazide) as a starting material instead of A2.

Experimental Example 1-50. Preparation of Compound 50 (4-amino-N-(2-(4-hydroxyphenyl)-2-oxoethyl)-3-morpholinobenzenesulfonamide)

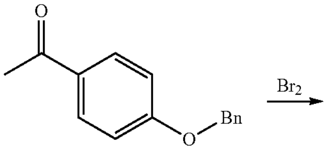

A22

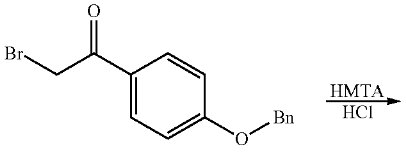

A23

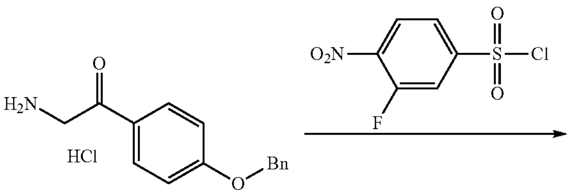

A24

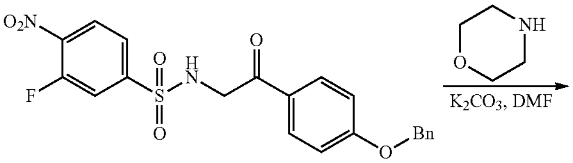

A112

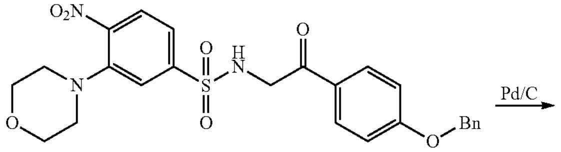

A113

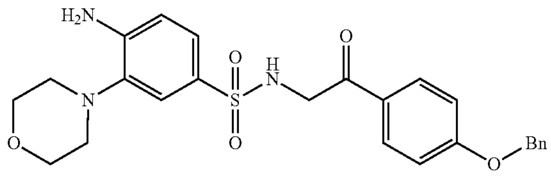

50

Compound 50 is obtained by a preparation method similar to that in Experimental Example 1-12 using 3-fluoro-4-nitrobenzenesulfonyl chloride instead of 4-nitrobenzene-1-sulfonyl chloride in Step 3 of Experimental Example 1-12.

Experimental Example 1-51. Preparation of Compound 51 (3,5-diamino-N-(2-(4-hydroxyphenyl)-2-oxoethyl)benzenesulfonamide)

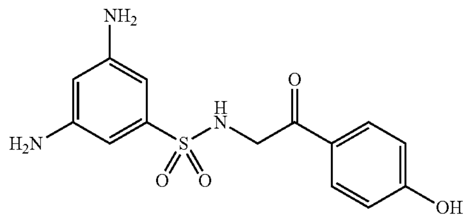 [SMILES: Nc1cc(N)cc(S(=O)(=O)NCC(=O)c2ccc(O)cc2)c1]

Compound 51 is obtained by a preparation method similar to that in Experimental Example 1-12 using 3,5-dinitrobenzenesulfonyl chloride (A20) instead of 4-nitrobenzene-1-sulfonyl chloride in Step 3 of Experimental Example 1-12.

Experimental Example 1-52. Preparation of Compound 52 (2-((4-aminophenyl)sulfonyl)-N'-(3-hydroxyphenyl)hydrazine-1-carboxamide)

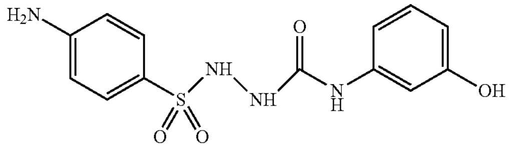 [SMILES: Nc1ccc(S(=O)(=O)NNC(=O)Nc2cccc(O)c2)cc1]

Compound 52 is obtained by the same preparation method as in Experimental Example 1-27 using 3-isocyanatophenol instead of isocyanatobenzene in Step 3 of Experimental Example 1-27.

Experimental Example 1-53. Preparation of Compound 53 (2-((4-amino-3-morpholinophenyl)sulfonyl)-N-phenylhydrazine-1-carboxamide)

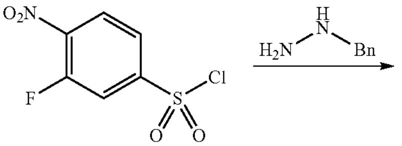

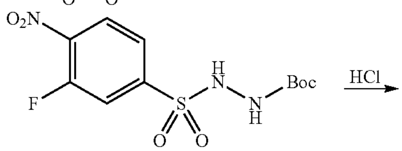

A114

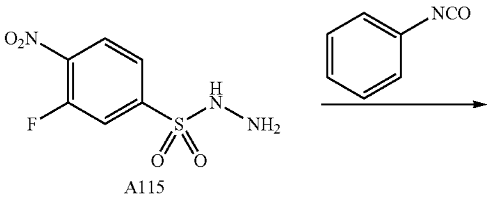

A115

-continued

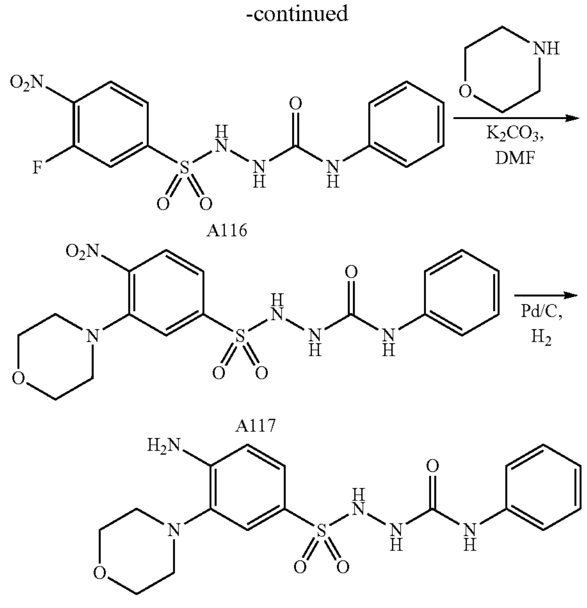

A116

A117

Compound 52

Compound 53 is obtained by a preparation method similar to that in Experimental Example 1-27 using 3-fluoro-4-nitrobenzenesulfonyl chloride as a starting material instead of 4-nitrobenzenesulfonyl chloride.

Experimental Example 1-54. Preparation of Compound 54 (4-hydroxy-N-(((4-methoxyphenyl)sulfonyl)methyl)benzamide)

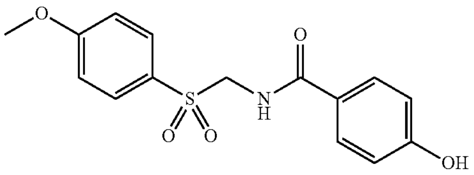 [SMILES: COc1ccc(S(=O)(=O)CNC(=O)c2ccc(O)cc2)cc1]

Compound 54 is obtained by the same preparation method as in Experimental Example 1-16 using 4-methoxybenzenethiol instead of 4-nitrobenzenethiol.

Experimental Example 1-55. Preparation of Compound 55 (N-(((4-aminophenyl)sulfonyl)methyl)-[1,1'-biphenyl]-4-carboxamide)

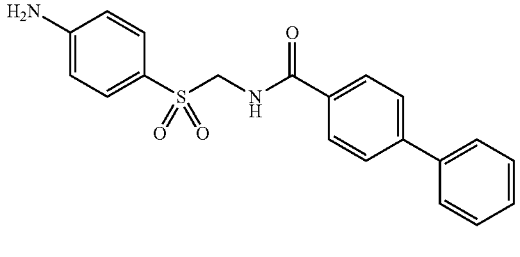 [SMILES: Nc1ccc(S(=O)(=O)CNC(=O)c2ccc(-c3ccccc3)cc2)cc1]

Compound 55 is obtained by a preparation method similar to that in Experimental Example 1-16 using [1,1'-biphenyl]-4-carboxamide as a starting material instead of an intermediate A28 of Experimental Example 1-16.

Example 2. Binding Assay Experiment

Example 2-1 Confirmation of Whether Muscle Actin is Arg/N-Degron Pathway Substrate A L6 cell line, which is a rat muscle-derived cell, was cultured using a DMEM medium containing 10% FBS and 1% streptomycin/penicillin in an incubator in which 5% carbon dioxide was maintained, and cells were aliquoted into a 12-well plate after the culture. The cells were additionally cultured for 24 hours so as to be completely attached to the surface of the plate. To confirm whether MG132 increased UBR1 binding, cells were collected after treatment with MG132 (10 uM) alone for 24 hours. To extract proteins from the collected cells, 50 uL of a lysis buffer (20 mM Tris, pH 7.4, 150 mM NaCl, 1% Triton-X-100, 2 mM NaF, 2 mM EDTA, 2 mM b-glycerophosphate, 5 mM sodium orthovanadate, 1 mM PMSF, leupeptin, aprotenin) was injected into each sample, and the cells were lysed. A sample buffer was added to each sample based on the measured total protein concentration, and the mixture was reacted at 100° C. for 5 minutes. After 5 uL was taken from the completely reacted sample and aliquoted into each well of an acrylamide gel, an immunoblotting method was performed, and the experimental results are illustrated in [FIG. 1]. For the immunoblotting method, a representative experiment was schematized from three or more independent experiments.

Referring to FIG. 1, it was confirmed that the levels of ACTA1, ACTC1, and ACTG2 were increased by MG132 compared to a control. Further, it was confirmed that the levels of ACTA1 and ACTG2 were increased when a UBR protein was knocked down. That is, it could be confirmed that muscle actin is an Arg/N-degron pathway substrate.

Example 2-2 Confirmation of Inhibition of R-nsP4 Degradation by In Vitro Transcription/Translation Method A TnT® Quick Coupled Transcription/Translation System kit was used to confirm the R-nsP4 expression of the compounds. After a pre-mix was made using Transcend Biotin-Lysyl-tRNA, methionine, bestatin, a TnTquick Master mix and a DHFR-Ub-R-nsP4 plasmid, the pre-mix was mixed with a compound (1 uM). After each sample was reacted at 30° C. for 40 minutes, a 5×SDS loading dye was added thereto. After the resulting mixture was reacted at 95° C. for 2 minutes, 5 uL was taken and aliquoted into each well of an acrylamide gel, and then an immunoblotting method was performed, and the experimental results are illustrated in [FIG. 2]. For an in vitro transcription/translation method, a representative experiment was schematized from three or more independent experiments.

Figure 2:
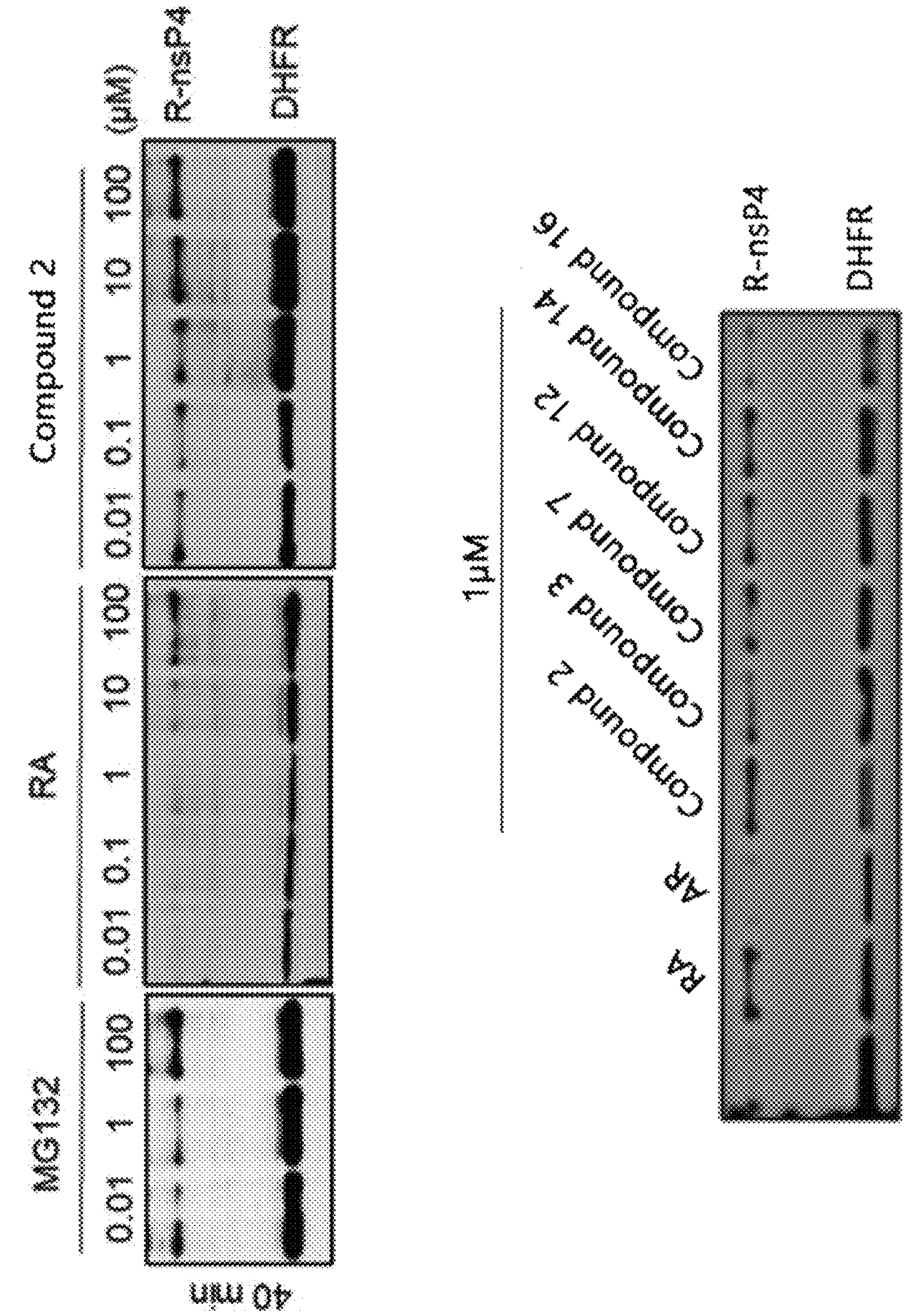
FIG. 2 illustrates the experimental results of confirming whether the degradation of R-nsp4, which should be degraded by allowing a compound (Compounds 2, 3, 7, 12, 14, and 16) to bind to UBR1, is suppressed using an in vitro transcription/translation method.

Referring to FIG. 2, it can be confirmed that the level of R-nsP4 is increased by Compound 2, Compound 3, Compound 7, Compound 12, Compound 14, and Compound 16 compared to the control. That is, it could be confirmed that in the case of treatment with the compound according to the present invention, the R-nsP4 level was increased by binding to UBR1.

Example 2-3 Evaluation of Inhibition of Intracellular RGS4 Degradation by Transfection A L6 cell line, which is a rat muscle-derived cell, was cultured using a DMEM medium containing 10% FBS and 1% streptomycin/penicillin in an incubator in which 5% carbon dioxide was maintained. In order to measure the UBR1 binding strength according to the treatment with a representative compound selected from the present compounds, cells were aliquoted into a 6-well plate. The cells were additionally cultured for 24 hours so as to be completely attached to the surface of the plate. Opti-MEM, Lipofectamine, and an RGS4plasmid was reacted for transfection. After the reaction was completed, the cells are treated such that DNA was expressed intracellularly. Cells were collected after treatment with a compound (5 uM) alone for 24 hours to confirm whether the compound increased UBR1 binding after 24 hours. To extract proteins from the collected cells, 50 uL of a lysis buffer (20 mM Tris, pH 7.4, 150 mM NaCl, 1% Triton-X-100, 2 mM NaF, 2 mM EDTA, 2 mM b-glycerophosphate, 5 mM sodium orthovanadate, 1 mM PMSF, leupeptin, aprotenin) was injected into each sample, and the cells were lysed. A sample buffer was added to each sample based on the measured total protein concentration, and the mixture was reacted at 100° C. for 5 minutes. After 5 uL was taken from the completely reacted sample and aliquoted into each well of an acrylamide gel, an immunoblotting method was performed, and the experimental results are illustrated in [FIG. 3]. For the immunoblotting method, a representative experiment was schematized from three or more independent experiments.

Figure 3:
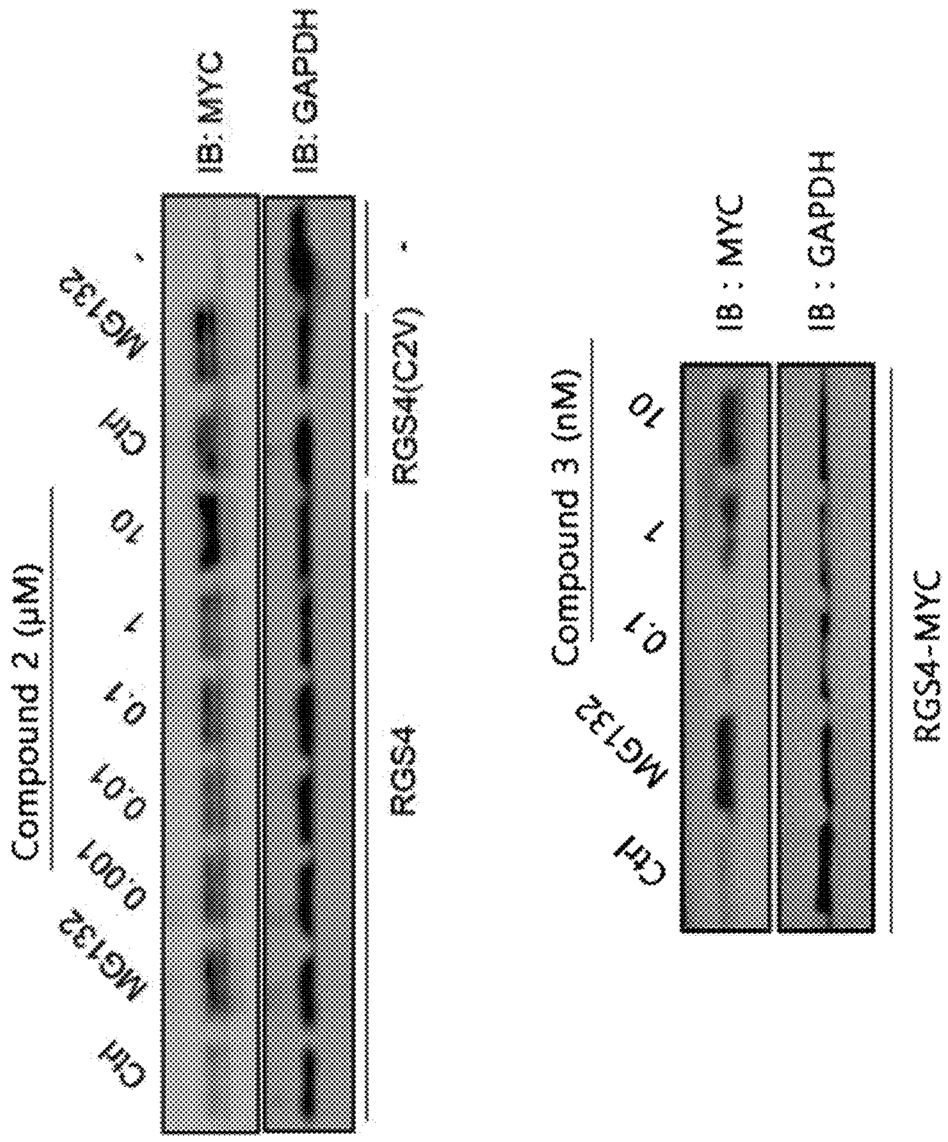
FIG. 3 illustrates the experimental results of confirming whether the degradation of RGS4, which is a substrate of UBR proteins in embryonic renal cells and should be degraded by allowing a compound (Compounds 2 and 3) to bind to UBR1, is suppressed using an immunoblotting method.

Referring to FIG. 3, it could be confirmed that the level of RGS4 was increased by Compound 2 and Compound 3 compared to the control. That is, it could be confirmed that in the case of treatment with the compound according to the present invention, the level of RGS4 was further increased by binding to UBR1.

Example 2-4 Evaluation of Inhibition of Muscle Cell Actin Degradation by Immunoblotting To evaluate the actin degradation of compounds in muscle cells, a L6 cell line, which is a rat muscle-derived cell, was cultured using a DMEM medium containing 10% FBS and 1% streptomycin/penicillin in an incubator in which 5% carbon dioxide was maintained. In order to measure the UBR1 binding strength according to the treatment with a representative compound selected from the present compounds, cells were aliquoted into a 12-well plate. The cells were additionally cultured for 24 hours so as to be completely attached to the surface of the plate. Cells were collected after treatment with a compound (5 uM) alone for 24 hours to confirm whether the compound increased UBR1 binding. To extract proteins from the collected cells, 50 uL of a lysis buffer (20 mM Tris, pH 7.4, 150 mM NaCl, 1% Triton-X-100, 2 mM NaF, 2 mM EDTA, 2 mM b-glycerophosphate, 5 mM sodium orthovanadate, 1 mM PMSF, leupeptin, aprotenin) was injected into each sample, and the cells were lysed. A sample buffer was added to each sample based on the measured total protein concentration, and the mixture was reacted at 100° C. for 5 minutes. After 5 uL was taken from the completely reacted sample and aliquoted into each well of an acrylamide gel, an immunoblotting method was performed, and the experimental results were illustrated in [FIG. 4], [FIG. 5], [FIG. 6], [FIG. 7], [FIG. 8], and [FIG. 9]. For the immunoblotting method, a representative experiment was schematized from three or more independent experiments.

Figure 4:
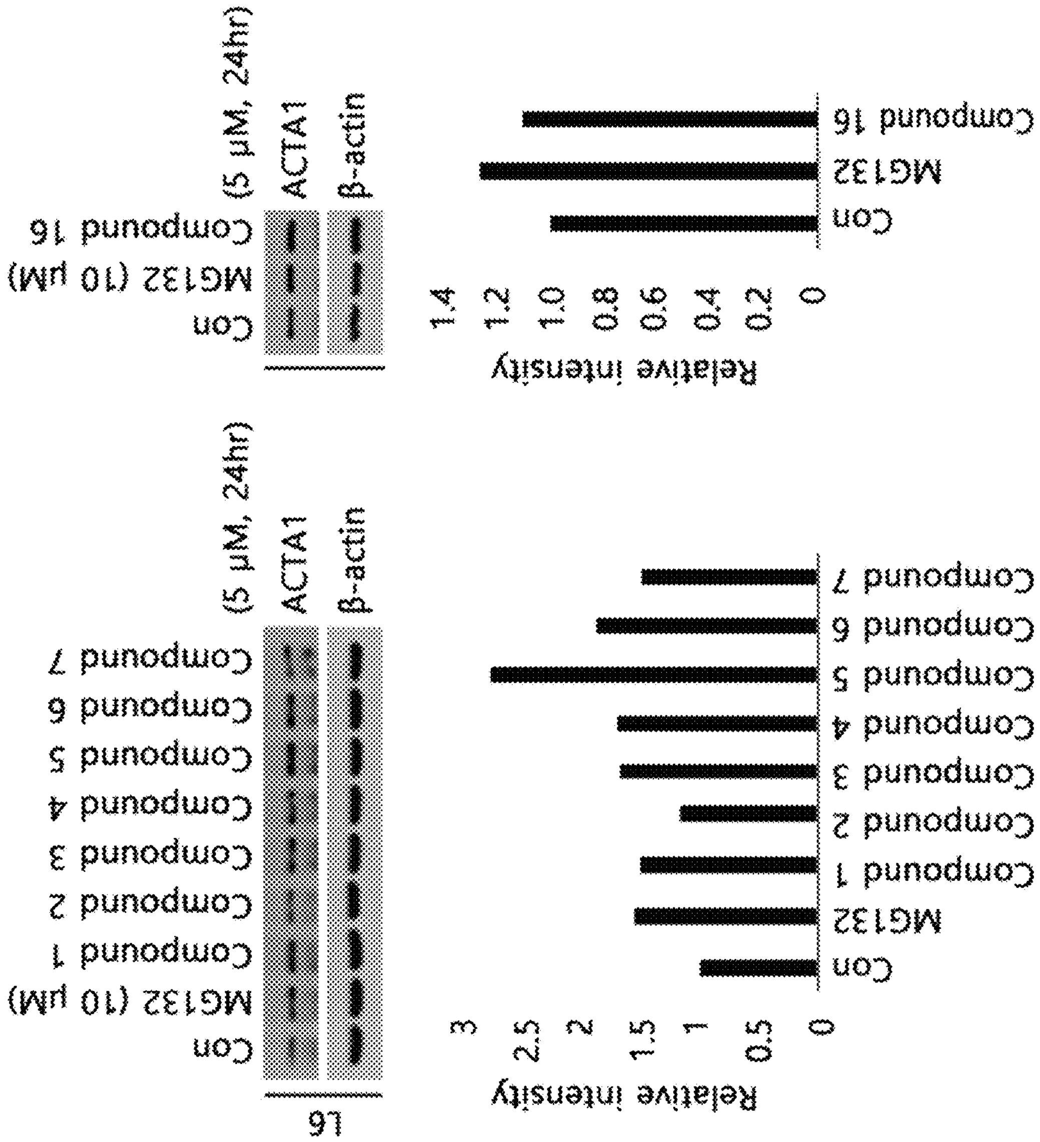
FIG. 4 illustrates the experimental results of confirming whether a compound (Compounds 1, 2, 3, 4, 5, 6, 7, and 16) suppresses the degradation of actin, which is a substrate of UBR proteins in muscle cells, using an immunoblotting method.
Figure 5:
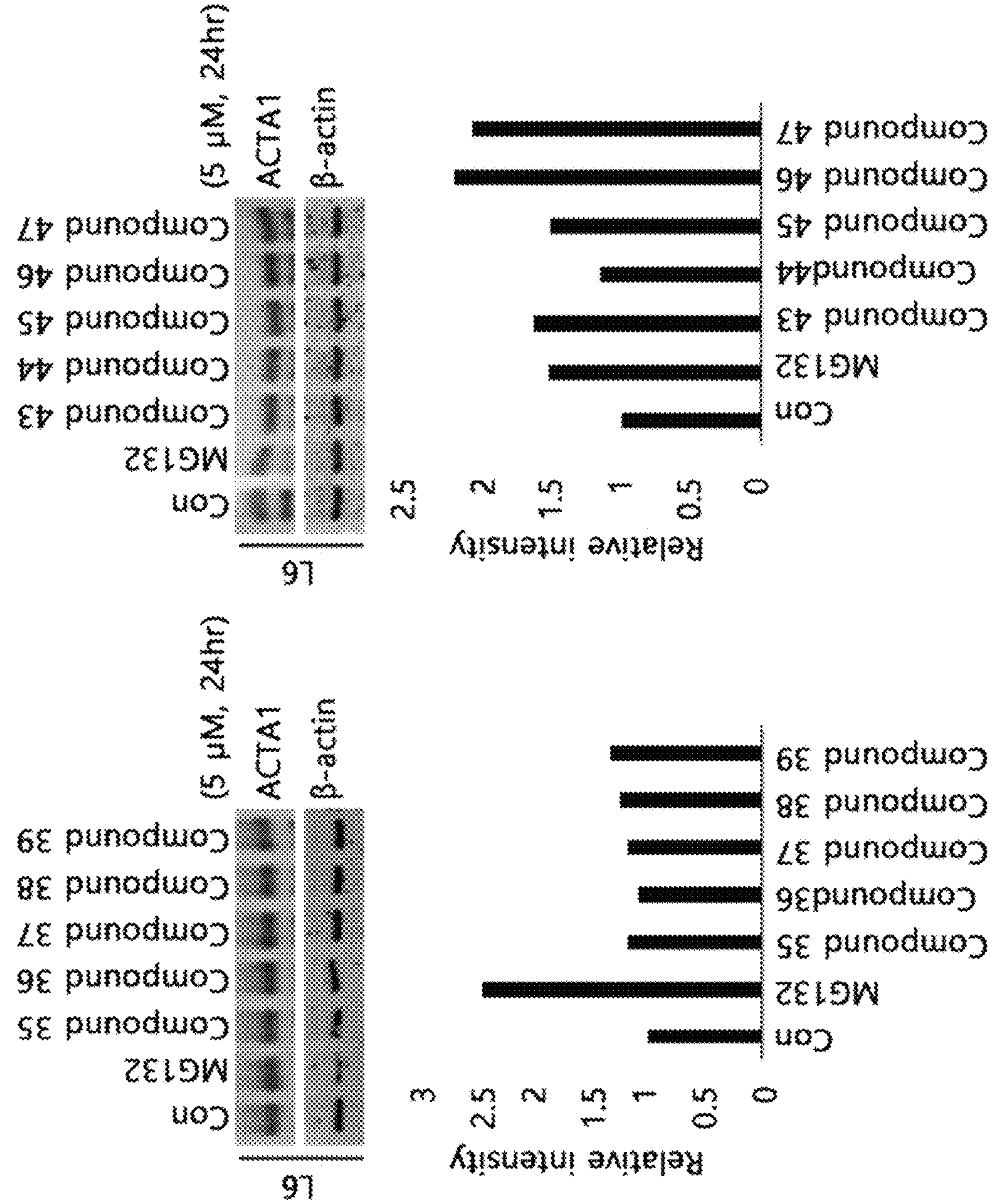
FIG. 5 illustrates the experimental results of confirming whether a compound (Compounds 35, 36, 37, 38, 39, 43, 44, 45, 46, and 47) suppresses the degradation of actin in muscle cells using an immunoblotting method.

Referring to FIGS. 4 and 5, it can be confirmed that the level of ACTA1 is further increased by Compound 1, Compound 2, Compound 3, Compound 4, Compound 5, Compound 6, Compound 7, Compound 16, Compound 35, Compound 36, Compound 37, Compound 38, Compound 39, Compound 43, Compound 44, Compound 45, Compound 46, and Compound 47 compared to the control. That is, it could be confirmed that in the case of treatment with the compound according to the present invention, the degradation of an intramuscular protein ACTA1 was inhibited by binding to UBR1.

Figure 6:
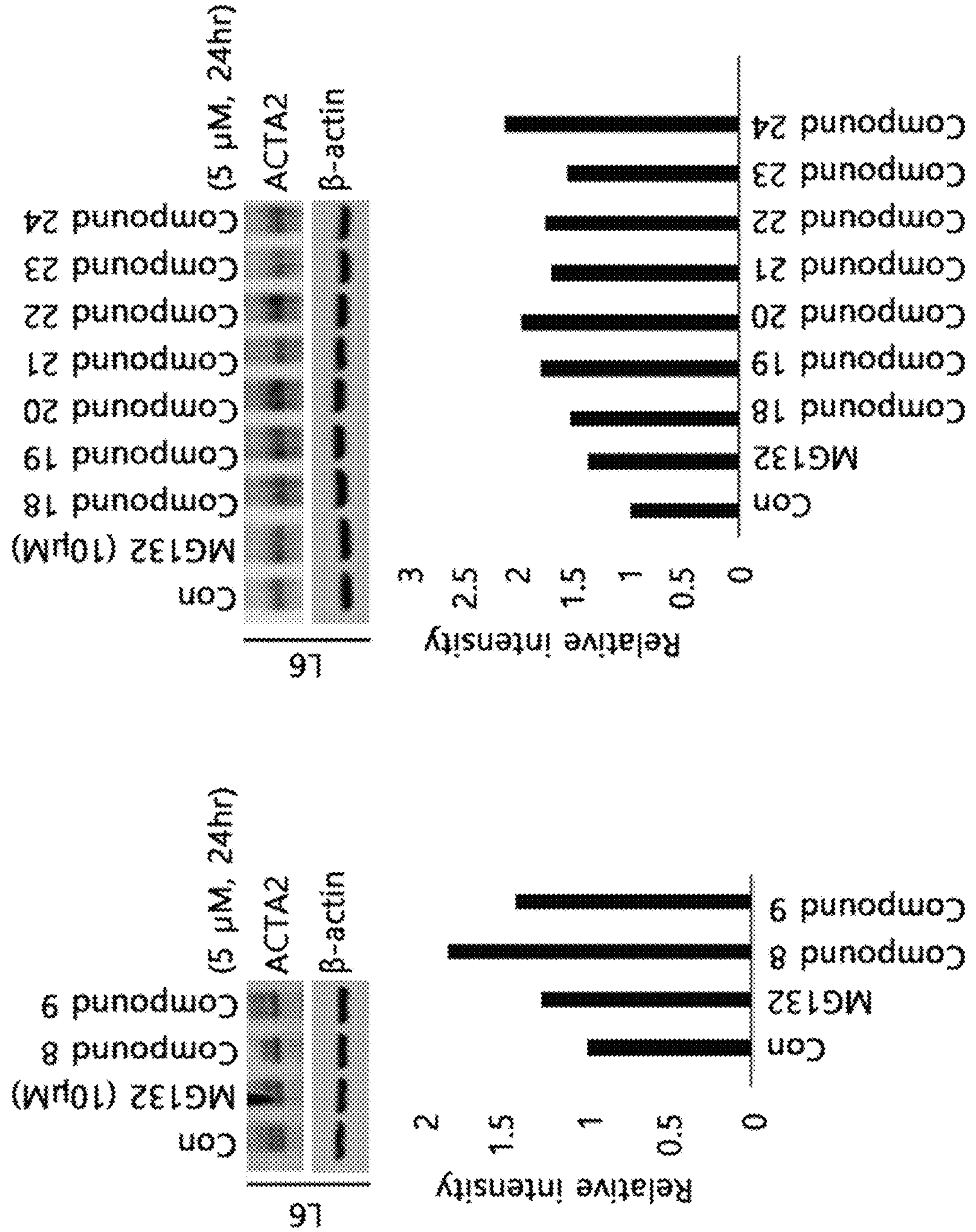
FIG. 6 illustrates the experimental results of confirming whether a compound (Compounds 8, 9, 18, 19, 20, 21, 22, 23, and 24) suppresses the degradation of actin in muscle cells using an immunoblotting method.
Figure 7:
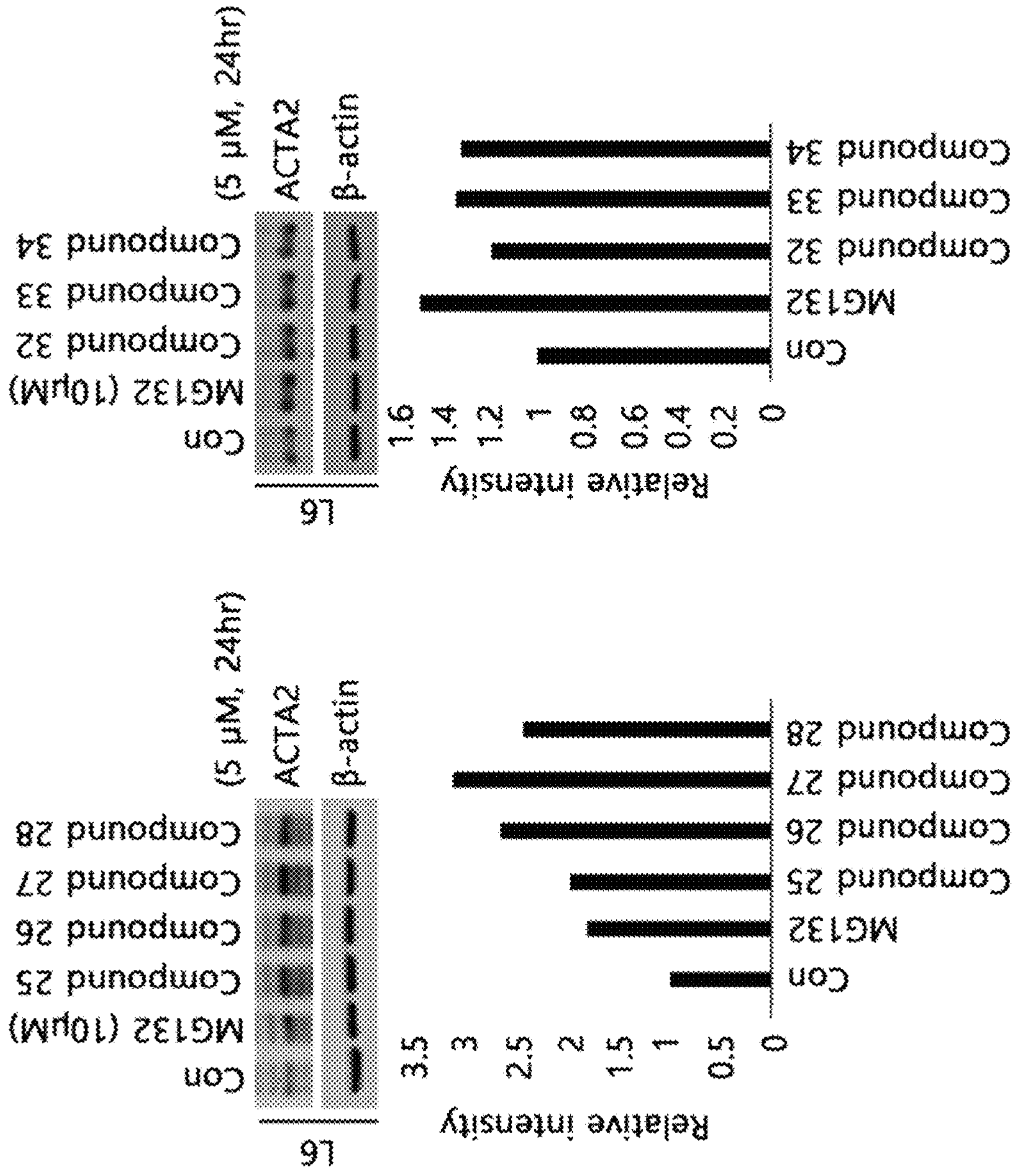
FIG. 7 illustrates the experimental results of confirming whether a compound (Compounds 25, 26, 27, 28, 32, 33, and 34) suppresses the degradation of actin in muscle cells using an immunoblotting method.

Referring to FIGS. 6 and 7, it can be confirmed that the level of ACTA2 is further increased by Compound 8, Compound 9, Compound 18, Compound 19, Compound 20, Compound 21, Compound 22, Compound 23, Compound 24, Compound 25, Compound 26, Compound 27, Compound 28, Compound 32, Compound 33, and Compound 34 compared to the control. That is, it could be confirmed that in the case of treatment with the compound according to the present invention, the degradation of an intramuscular protein ACTA2 was inhibited by binding to UBR1.

Figure 8:
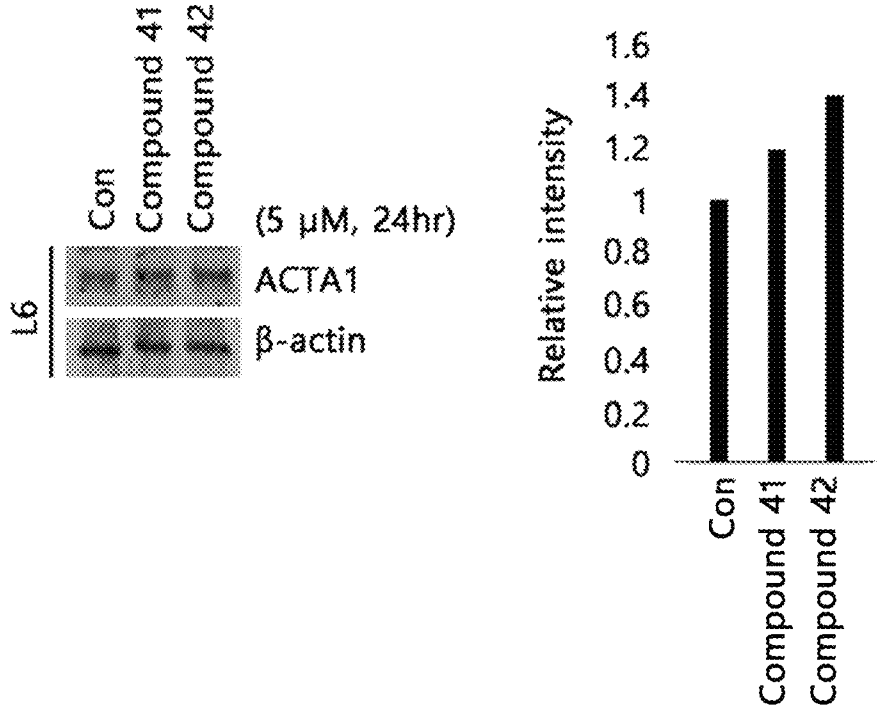
FIG. 8 illustrates the experimental results of confirming whether a compound (Compounds 41 and 42) suppresses the degradation of actin in muscle cells using an immunoblotting method.

Referring to FIG. 8, it can be confirmed that the level of ACTC1 is further increased by Compound 41 and Compound 42 compared to the control. That is, it could be confirmed that in the case of treatment with the compound according to the present invention, the degradation of an intramuscular protein ACTC1 was inhibited by binding to UBR1.

Figure 9:
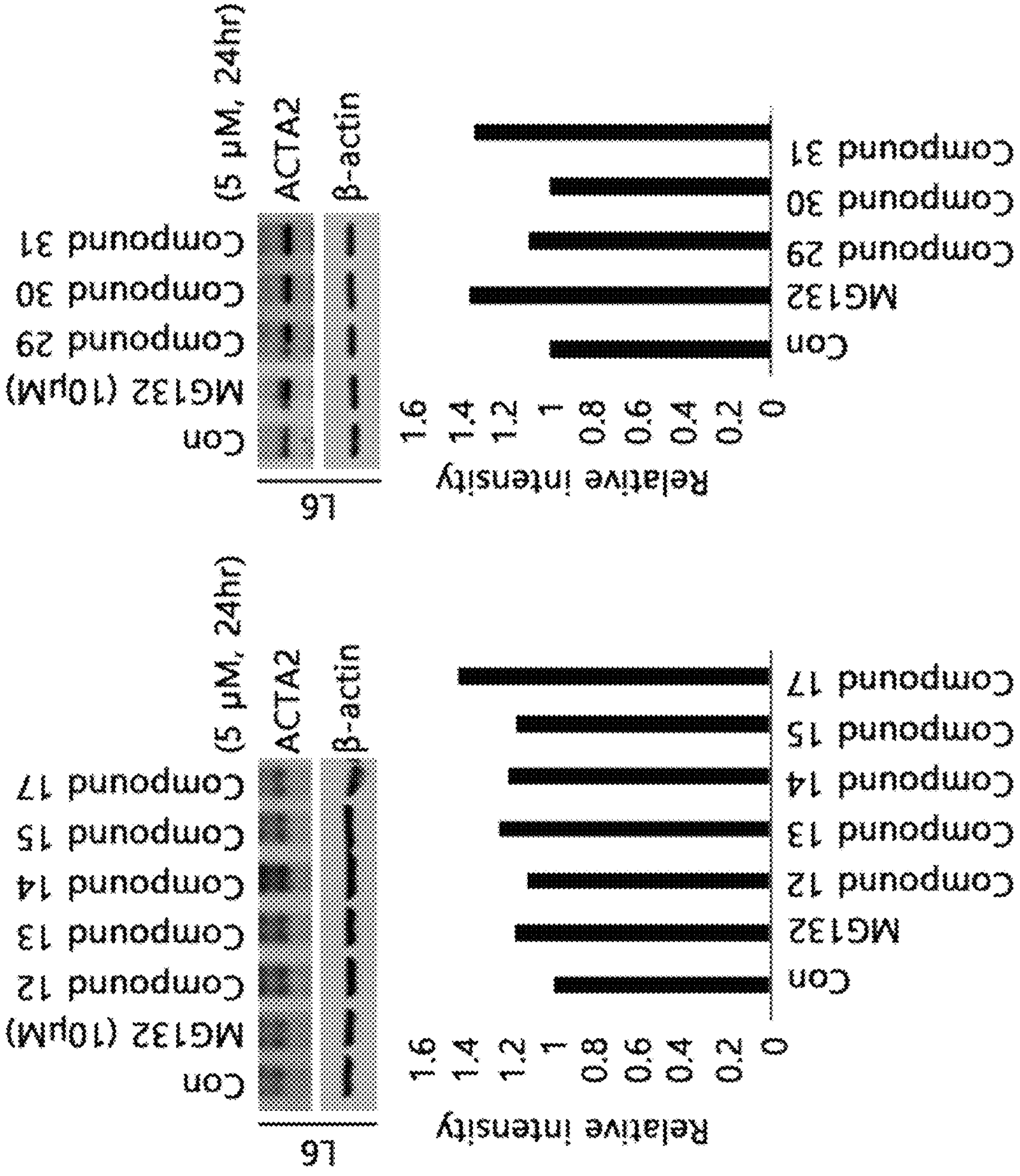
FIG. 9 illustrates the experimental results of confirming whether a compound (Compounds 12, 13, 14, 15, 17, 29, 30, and 31) suppresses the degradation of actin in muscle cells using an immunoblotting method.

Referring to FIG. 9, it could be confirmed that the level of ACTG2 was further increased by Compound 12, Compound 13, Compound 14, Compound 15, Compound 17, Compound 29, Compound 30, and Compound 31 compared to the control. That is, it could be confirmed that in the case of treatment with the compound according to the present invention, the degradation of an intramuscular protein ACTG2 was inhibited by binding to UBR1.

Example 2-5 Evaluation of UBR Box Domain Binding Strength by Immunoprecipitation Analysis To evaluate the binding strength of the compounds to UBR1, UBR2, UBR3 and UBR5 through the UBR box domain, a L6 cell line, which is a rat muscle-derived cell, was cultured using a DMEM medium containing 10% FBS and 1% streptomycin/penicillin in an incubator in which 5% carbon dioxide was maintained. In order to measure the UBR1 binding strength according to the treatment with a representative compound selected from the present compounds, cells were aliquoted into a 100 pi dish. The cells were additionally cultured for 24 hours so as to be completely attached to the surface of the plate. In order to confirm whether the compound increased UBR1 binding, cells are treated with a compound (5 uM), the proteasome inhibitor MG132 (10 uM), or a positive control (5 uM) alone for 24 hours, and then the cells were collected. To extract proteins from the collected cells, 50 uL of a lysis buffer (20 mM Tris, pH 7.4, 150 mM NaCl, 1% Triton-X-100, 2 mM NaF, 2 mM EDTA, 2 mM b-glycerophosphate, 5 mM sodium orthovanadate, 1 mM PMSF, leupeptin, aprotenin) was injected into each sample, and the cells were lysed. Each sample was reacted with a UBR1 antibody for 16 hours based on the measured total protein concentration, and then reacted with Protein A/G beads for 3 hours. A sample buffer was added to the completely reacted sample and the resulting mixture was reacted at 100° C. for 5 minutes. After 20 uL was taken from the completely reacted sample and aliquoted into each well of an acrylamide gel, an immunoblotting method was performed, and the experimental results are illustrated in [FIG. 10] and [FIG. 11]. For the immunoblotting method, a representative experiment was schematized from three or more independent experiments.

Figure 10:
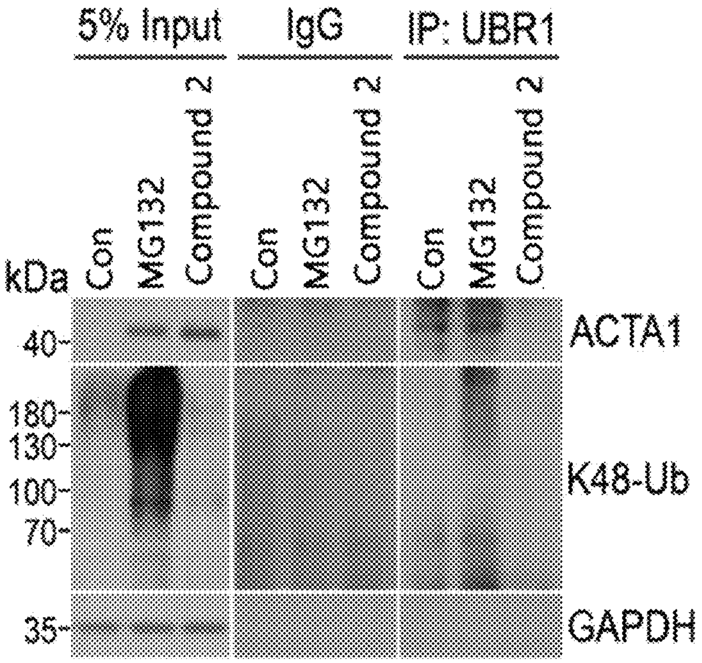
FIGS. 10 and 11 illustrate the experimental results confirming the efficacy of a compound (Compound 2) binding to UBRs 1, 2, 3, and 5 in cells using an immunoblotting method.
Figure 10:
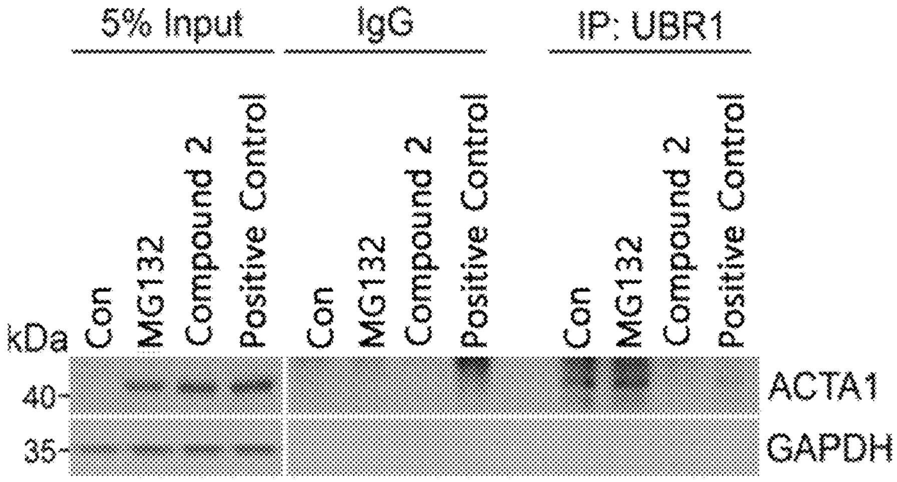
Figure 11:
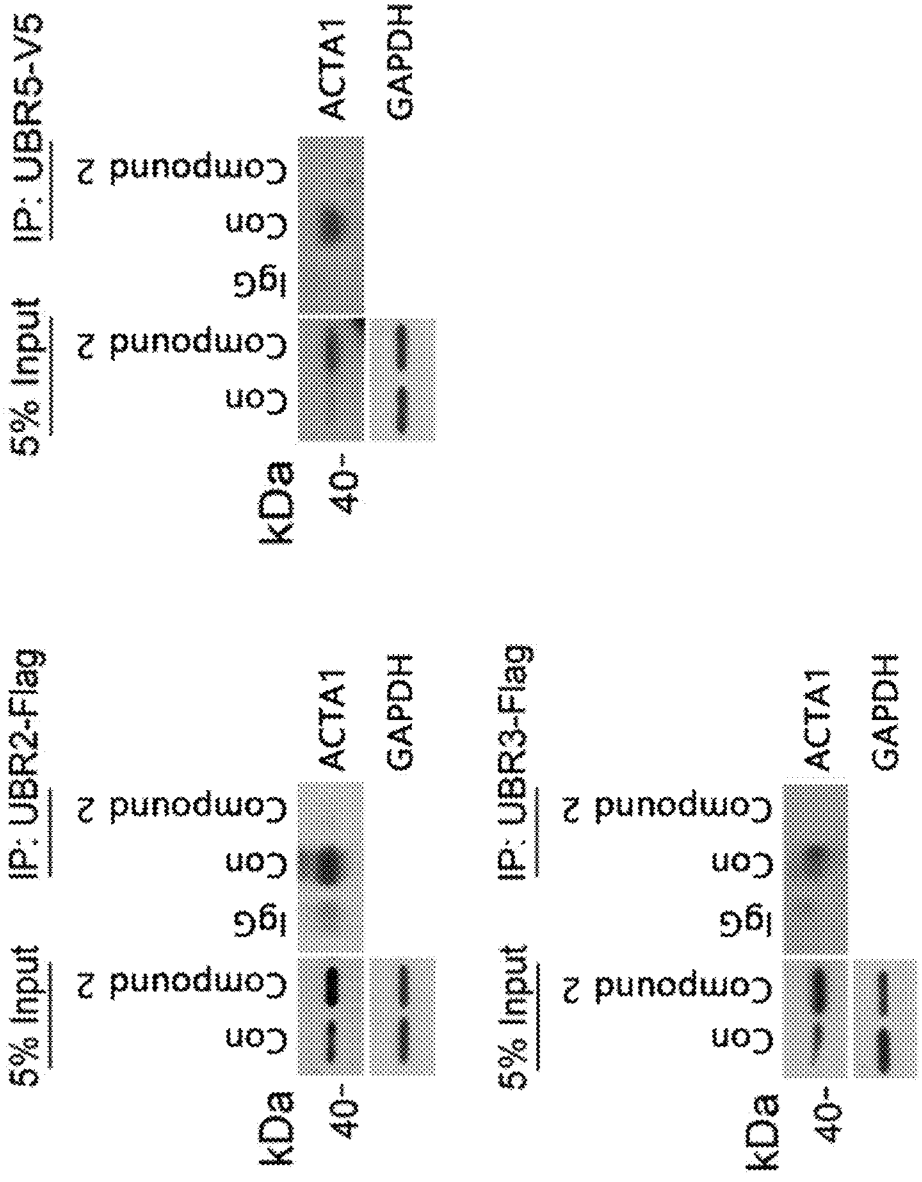
Figure 12:
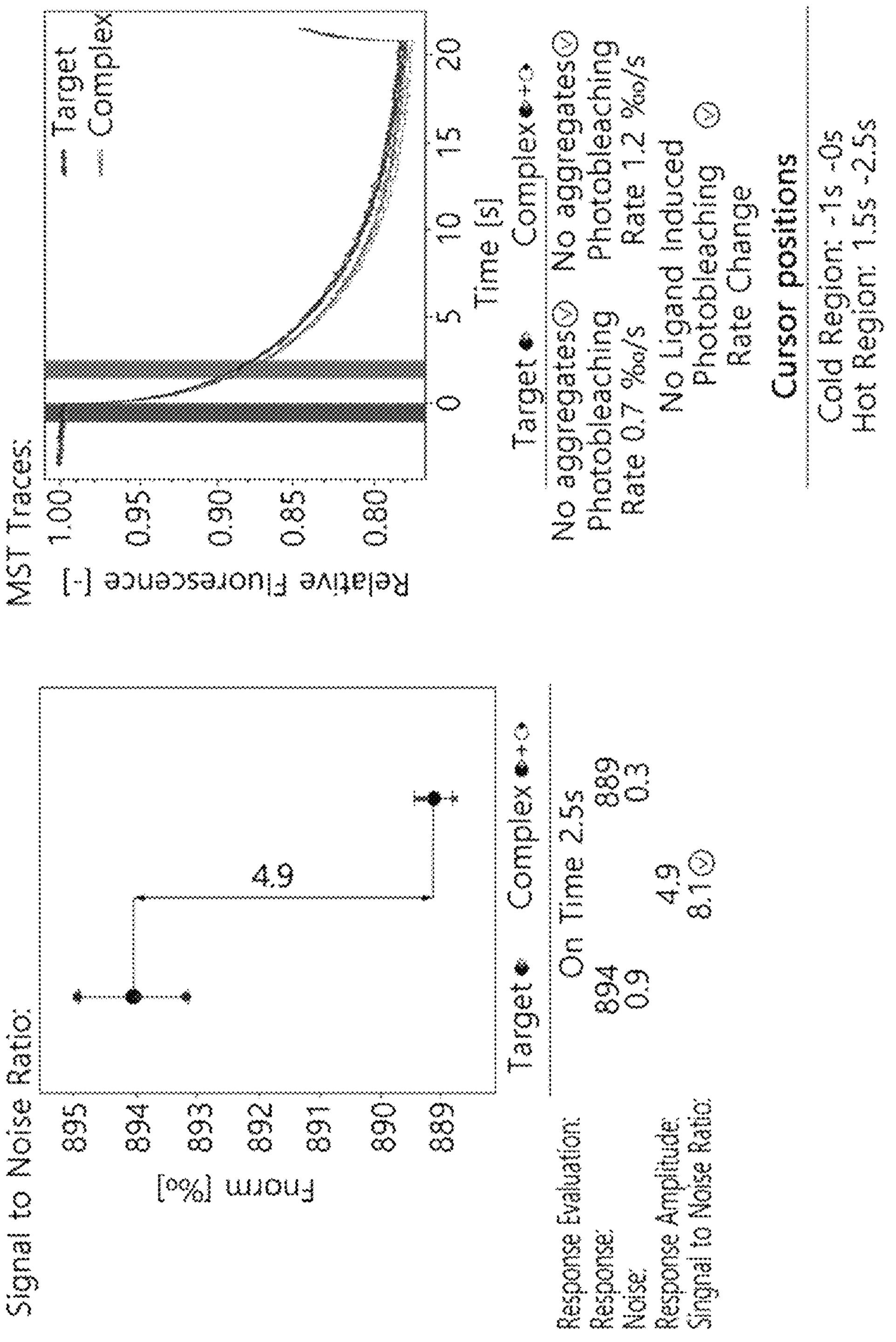
FIGS. 12, 13, 14, 15, 16, 17, 18 and 19 illustrates the microscale thermophoresis (MST) experimental results of confirming whether a compound (Compounds 1, 2, 5, 8, 9, 11, 12, and 13) binds to UBR1.
Figure 13:
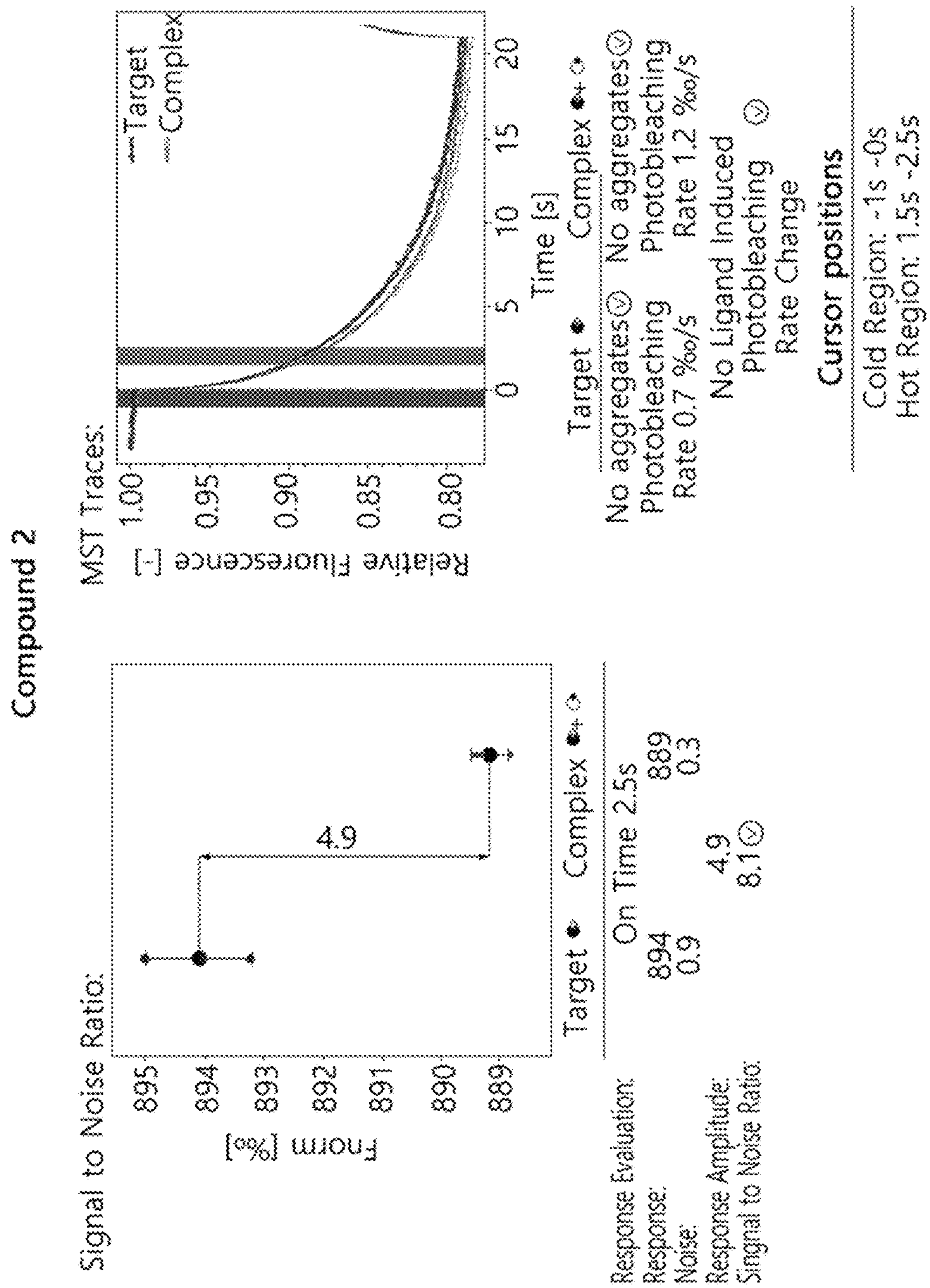
Figure 14:
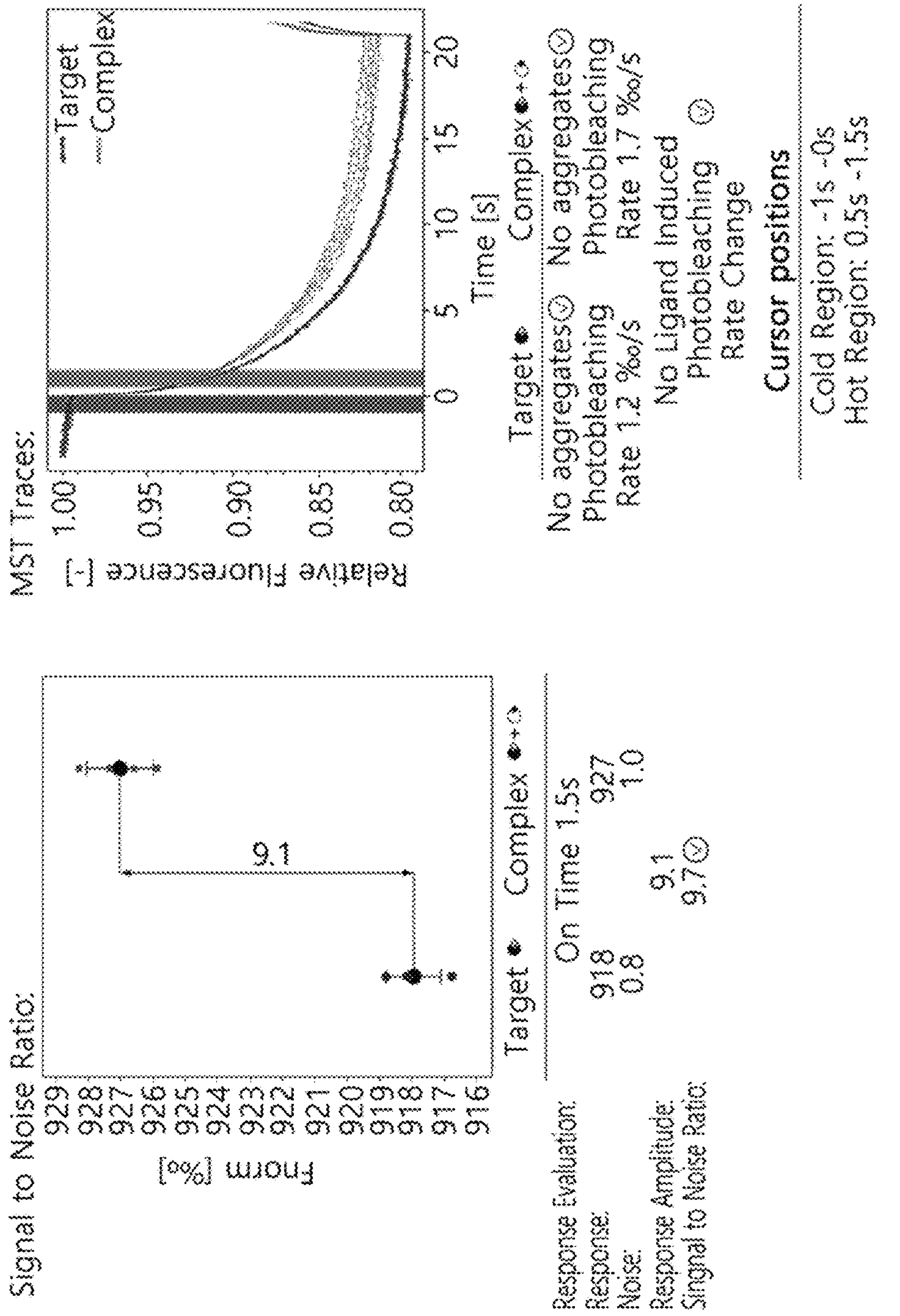
Figure 15:
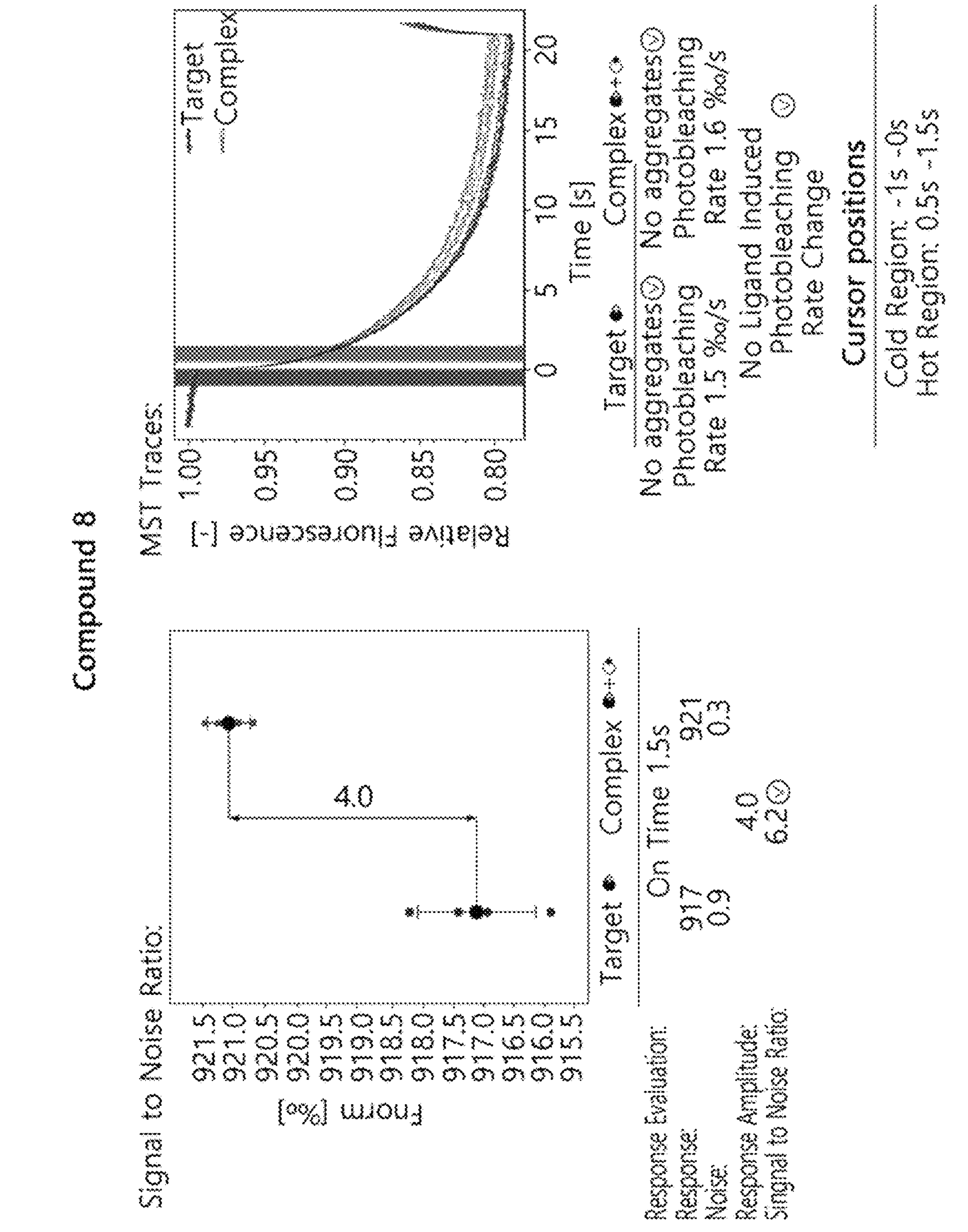
Figure 16:
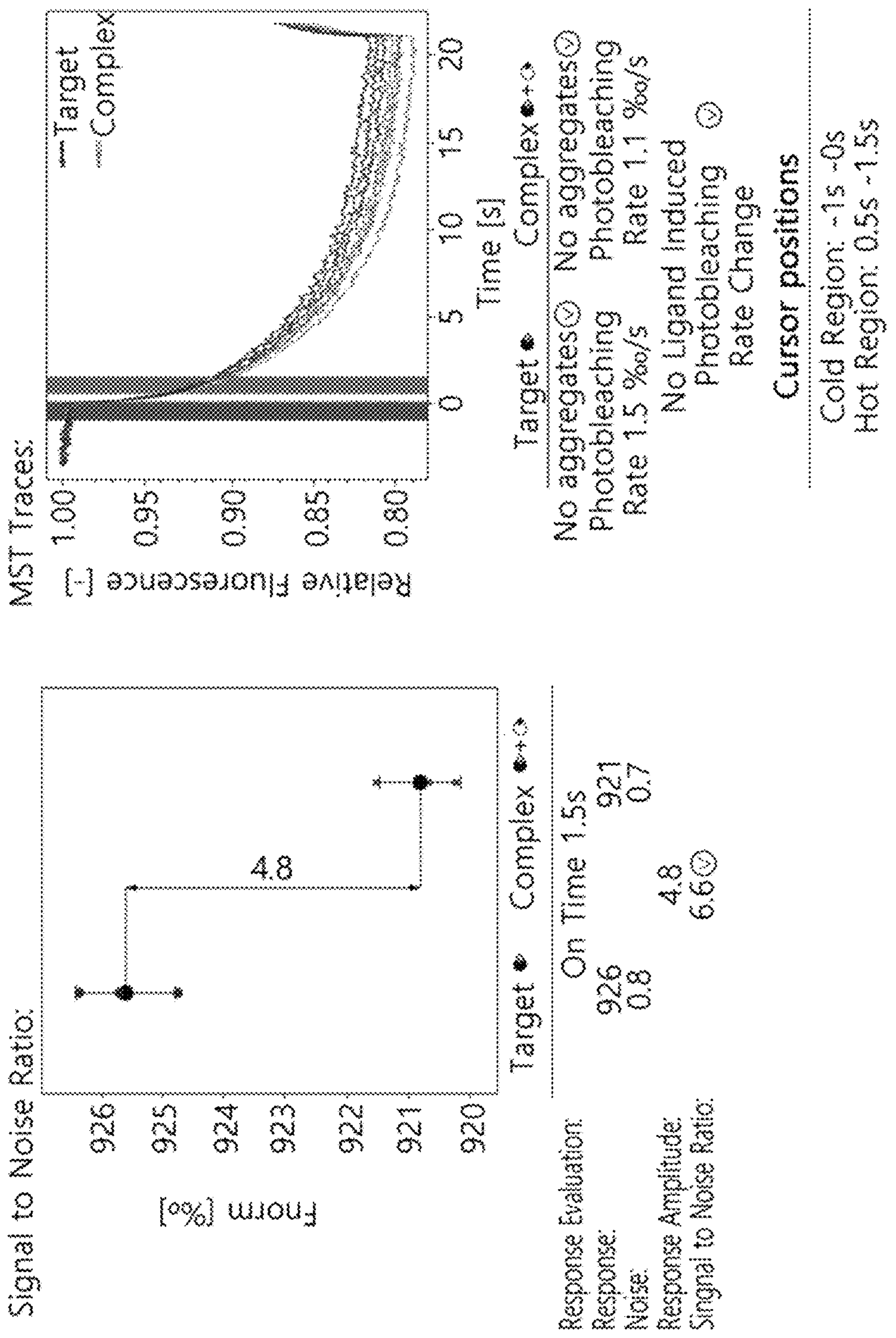
Figure 17:
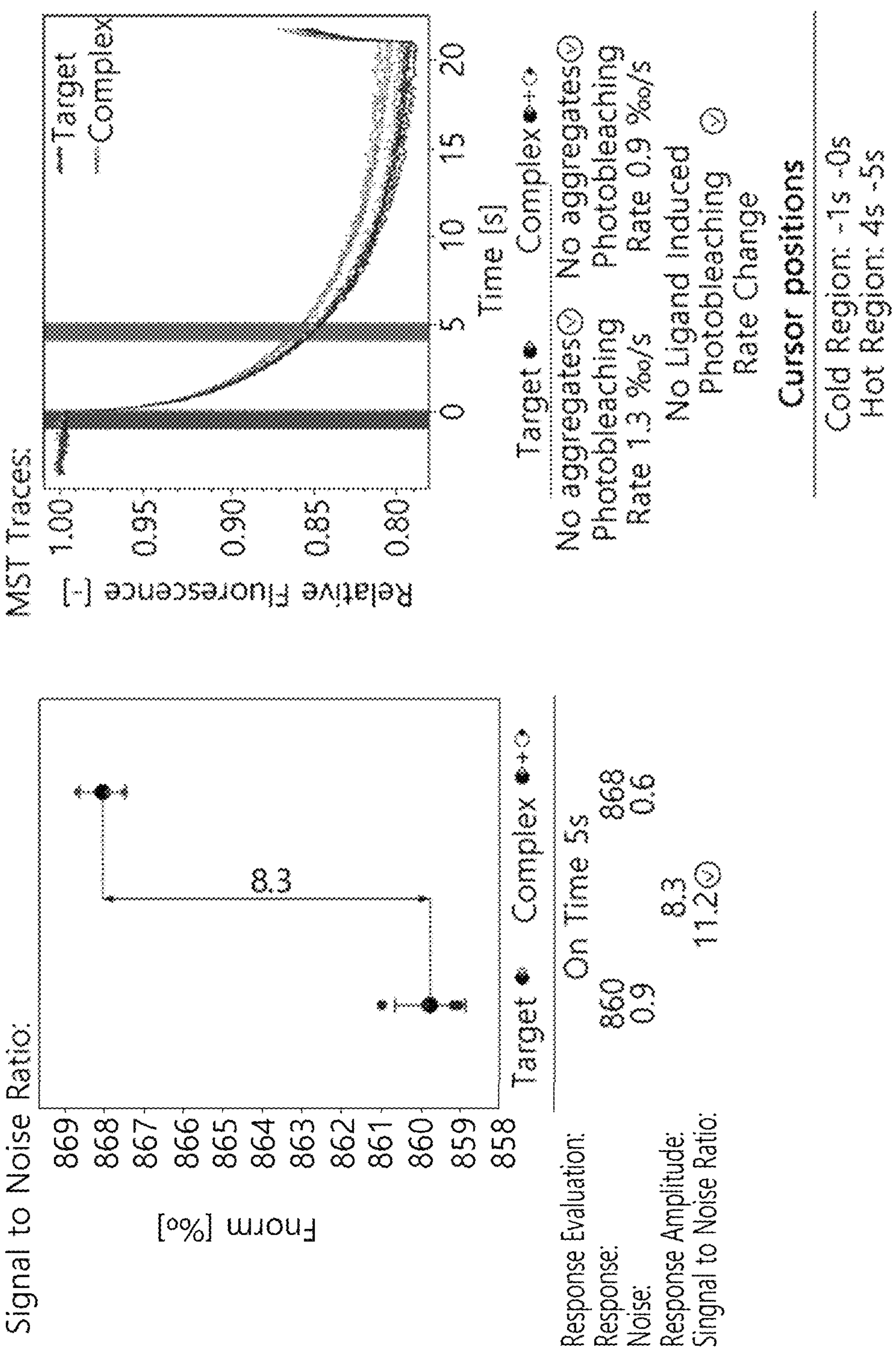
Figure 18:
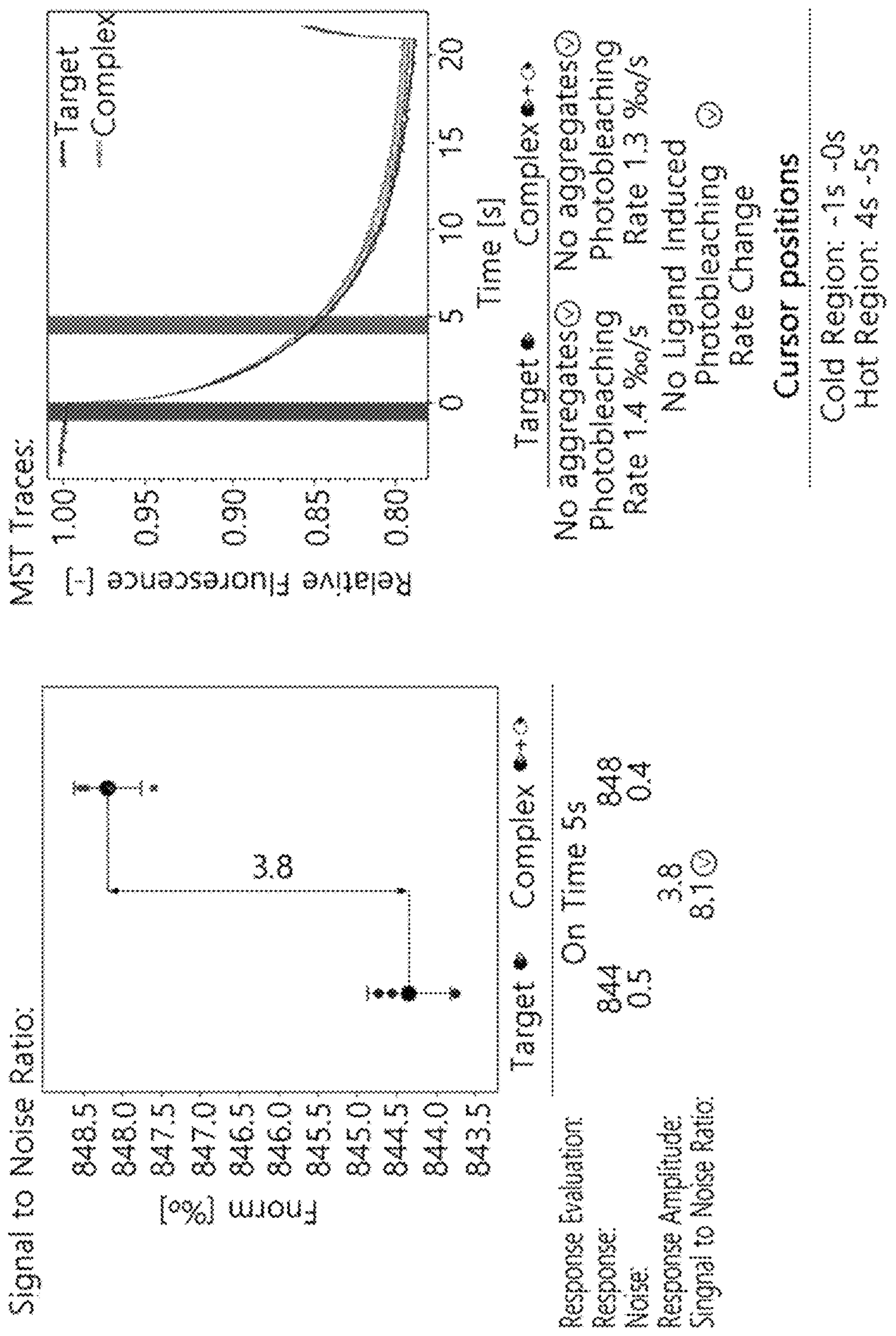
Figure 19:
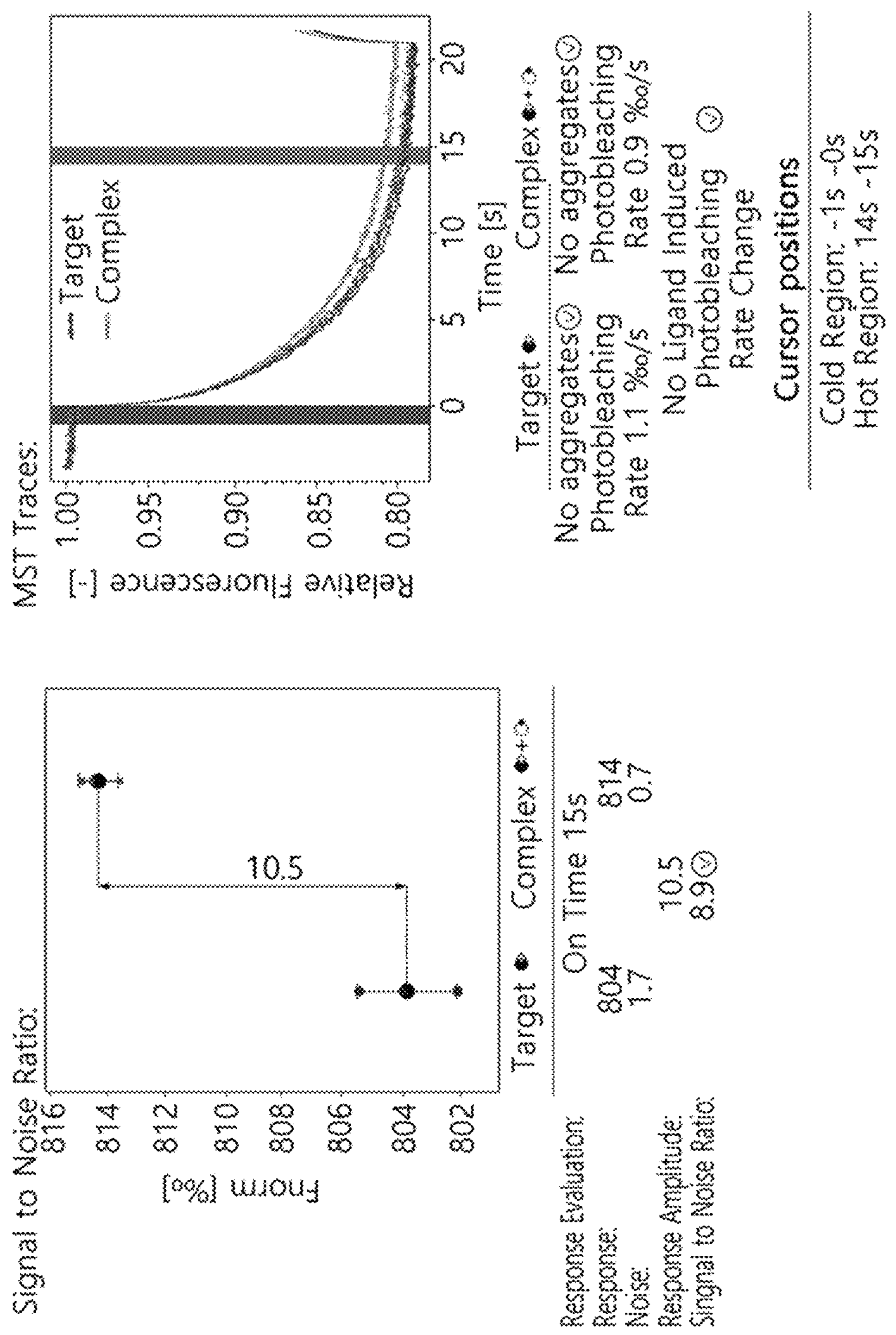

Referring to FIGS. 10 and 11, it can be confirmed that Compound 2, which is a compound according to the present invention, actually binds to the UBR box domain of the UBR proteins by the result showing that the binding strength of ACTA1, UBR2 and ACTA1, UBR3 and ACTA1, UBR5 and ACTA1 were reduced when the cells were treated with the compound, similarly to the positive control. Whereas the binding strength between UBR1 and a substrate ACTA1 was maintained when the cells were treated with the DMSO control group and a proteasome inhibitor MG132 used as a negative control.

That is, it could be confirmed that in the case of treatment with the compound according to the present invention, the degradation of an intramuscular protein ACTG2 was inhibited by binding to UBR1, UBR2, UBR3, or UBR5.

Example 2-6 Evaluation of UBR Box Domain Binding Strength by MST

1) Preparation of UBR1 Protein

A Gln97-Pro168 portion corresponding to the UBR box of Human UBR1 (UniProt ID: Q81WV7) was cloned into a modified expression vector, and then expressed in *E. coli*. After affinity chromatography was used, a tag was removed by a protease, and then Gly-His-Met was added to the N-terminal. After ion chromatography was performed, a final UBR box protein of a UBR1 was purified using gel filtration chromatography in a buffer composition of 10 mM NaCl, 20 mM Tris-HCl, 2 mM beta-mercaptoethanol, and pH 7.5.

2) UBR1 UBR Box Protein Labeling

A dye of the Monolith protein labeling kit RED-NHS 2nd generation (Cat #MO-L011) has an NHS-ester group that forms a covalent bond with primary amines (lysine residues). This dye is optimized for a Monolith-series device equipped with a RED detector. A purified UBR1 UBR box protein was labeled according to the presented protocol using this kit.

3) Measurement of Presence or Absence of Binding Between UBR1 and Ligand Using MST Thermophoresis refers to a phenomenon in which particles move due to a temperature gradient. Particles present in a high temperature region have greater kinetic energy than particles present in a low temperature region, and more frequently collide with surrounding particles with greater energy. As a result, particles move from the high temperature region to the low temperature region.

Thermophoresis of proteins is typically different from that of protein-ligand complexes. This is because the binding of the ligand changes its size, electric charge, and solvation energy. Furthermore, MST may detect changes in the solvent entropy of protein molecules caused by ligand binding even though the ligand binding does not significantly change the size and electric charge of the protein. Therefore, the binding of the UBR1 UBR box protein and the ligand compound was measured using MST, and it was confirmed that the presented ligand binds to the UBR1 UBR box (see FIGS. 12 to 19).

What is claimed is:

1. A compound or a salt thereof, wherein the compound is selected from the group consisting of:

4-amino-N'-(4-hydroxybenzoyl)benzenesulfonohydrazide;

4-amino-N'-(4-hydroxybenzoyl)-3-morpholinobenzenesulfonohydrazide;

N'-(4-hydroxybenzoyl)-2-oxoindoline-5-sulfonohydrazide;

N'-(4-hydroxybenzoyl) indoline-5-sulfonohydrazide;

N'—([1,1'-biphenyl]-4-carbonyl)-4-aminobenzenesulfonohydrazide;

N'—([1,1'-biphenyl]-3-carbonyl)-4-aminobenzenesulfonohydrazide;

3-amino-N'-(4-hydroxybenzoyl)benzenesulfonohydrazide;

4-(1-aminoethyl)-N'-(4-hydroxybenzoyl)benzenesulfonohydrazide;

3,5-diamino-N'-(4-hydroxybenzoyl)benzenesulfonohydrazide;

N'-(4-hydroxybenzoyl)-4-((2-hydroxyethyl)amino)benzenesulfonohydrazide;

N'-(4-hydroxybenzoyl)-4-methoxybenzenesulfonohydrazide;

4-((2-(4-hydroxybenzoyl)hydrazinyl)sulfonyl)benzimidamide;

4-((2-(4-hydroxybenzoyl)hydrazinyl)sulfonyl)benzamide;

6-amino-N'-(4-hydroxybenzoyl)-[1,1'-biphenyl]-3-sulfonohydrazide;

4-(2-((4-aminophenyl)sulfonyl)hydrazine-1-carbonyl)benzamide;

4-amino-N'-(1H-indole-3-carbonyl)benzenesulfonohydrazide;

4-amino-N'-(4-hydroxybenzoyl)-3-(pyrrolidin-1-yl)benzenesulfonohydrazide;

N'-(4-hydroxybenzoyl)-4-nitro-3-(pyrrolidin-1-yl)benzenesulfonohydrazide;

4-amino-N'-(4-hydroxybenzoyl)-3-(piperidin-1-yl)benzenesulfonohydrazide;

N'-(4-hydroxybenzoyl)-1H-pyrazole-4-sulfonohydrazide;

N'-(4-hydroxybenzoyl) indoline-4-sulfonohydrazide;

N'-(4-hydroxybenzoyl)-1H-indole-4-sulfonohydrazide;

4-amino-N'-(1H-indole-4-carbonyl)-3-morpholinobenzenesulfonohydrazide;

4-amino-N'-(indoline-4-carbonyl)benzenesulfonohydrazide;

4-amino-N'-(4-hydroxybenzoyl)-3-(piperazin-1-yl)benzenesulfonohydrazide;

4-amino-N'-(2,3-dihydro-1H-indene-2-carbonyl)benzenesulfonohydrazide;

4-amino-N'-(isoindoline-2-carbonyl)benzenesulfonohydrazide;

N'-(4-hydroxybenzoyl)-1H-indole-2-sulfonohydrazide;

4-amino-N'-(2-phenylacetyl)benzenesulfonohydrazide;

N'-(4-hydroxybenzoyl)-1H-indazole-3-sulfonohydrazide;

4-amino-N'-(indoline-6-carbonyl)benzenesulfonohydrazide;

4-amino-N'-(indoline-3-carbonyl)benzenesulfonohydrazide;

N'-(4-hydroxybenzoyl) piperidine-4-sulfonohydrazide;

4-amino-N'-(indoline-6-carbonyl)-3-morpholinobenzenesulfonohydrazide;

4-amino-N'-(piperazine-1-carbonyl)benzenesulfonohydrazide;

4-amino-3-morpholino-N'-(piperazine-1-carbonyl)benzenesulfonohydrazide;

N'-(4-hydroxybenzoyl)-2-methylthiazole-4-sulfonohydrazide;

(1S,4S)-4-amino-N'-(4-hydroxybenzoyl)cyclohexane-1-sulfonohydrazide;

(1R,4R)-4-amino-N'-(4-hydroxybenzoyl)cyclohexane-1-sulfonohydrazide;

4-((2-(4-hydroxybenzoyl) hydrazinyl) sulfonyl)-5-methylfuran-2-carboxylic acid;

N'-(4-hydroxybenzoyl) pyrrolidine-3-sulfonohydrazide;

N'-(4-hydroxybenzoyl)-1H-pyrrolo[2,3-b]pyridine-2-sulfonohydrazide;

2-((4-aminophenyl) sulfonyl)-N-(3-hydroxyphenyl) hydrazine-1-carboxamide;

and 2-((4-amino-3-morpholinophenyl) sulfonyl)-N-phenylhydrazine-1-carboxamide.

2. The compound or the salt thereof of claim 1, wherein the compound is selected from the group consisting of:

4-amino-N'-(4-hydroxybenzoyl)benzenesulfonohydrazide;

4-amino-N'-(4-hydroxybenzoyl)-3-morpholinobenzenesulfonohydrazide; and 4-amino-N'-(1H-indole-4-carbonyl)-3-morpholinobenzenesulfonohydrazide.

3. A pharmaceutical composition comprising the compound of claim 1 or pharmaceutically acceptable salt thereof, and an excipient.

4. A method for treating UBR related disease, the method comprising:

administering to a subject in need thereof a therapeutically effective amount of a pharmaceutical composition comprising a compound or a salt thereof, wherein the compound has the structure of formula 1-1:

[formula 1-1]

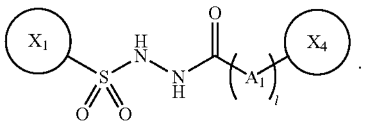

wherein $X_1$ is an optionally substituted with one or more $R_2$ or unsubstituted phenyl, cycloalkyl or heterocyclyl;

each $R_2$ is independently selected from alkyl, alkoxy, amino, aminoalkyl, —$NO_2$, =O, —$NHC_2H_4OH$, —C(=NH)$NH_2$, —C(=O)$NH_2$, —C(=O)$NHCH_3$, —C(=O)OH, phenyl or heterocycloalkyl;

$X_4$ is an optionally substituted with one or more $R_3$ or unsubstituted phenyl, cycloalkyl or heterocylyl;

each $R_3$ is independently selected from alkyl, alkoxy, amino, halo, hydroxyl, alkylamino, dialkylamino, —$NO_2$, —CONR'R", —$CO_2$R', —NHCOR', phenyl or heterocycloalkyl;

each R' and R" is independently-H or alkyl;

$A_1$ is $CH_2$ or NH; and

I is an integer of 0 or 1.

5. The method of claim 4, wherein the UBR related disease is selected from muscle loss caused by muscular dystrophy, muscle wasting diseases mediated by muscle loss or degradation, diseases caused by excessive protein degradation, Johanson-Blizzard syndrome, obstructive urinary tract disease, autoimmune pancreatitis, or Usher syndrome.

6. The method of claim 5, wherein the muscle loss caused by muscular dystrophy is Becker, Congenital, Duchenne, Distal, Emery-Dreifuss, Facioscapulohumeral, Limb-girdle, myotonic, or oculopharyngeal.

7. The method of claim 5, wherein the muscle wasting diseases mediated by muscle loss or degradation is sarcopenia or cancer cachexia.

8. The method of claim 5, wherein the muscle wasting diseases caused by excessive protein degradation is liposarcoma, or cystic fibrosis.

9. The method of claim 5, wherein the obstructive urinary tract disease is urethral obstruction sequence.

10. A method for binding a compound or a salt thereof to a UBR box domain in a subject, the method comprising:

administering a composition comprising the compound or the salt thereof, wherein the compound has the structure of formula 1-1:

[formula 1-1]

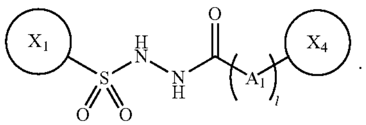

wherein the $X_1$ is an optionally substituted with one or more $R_2$ or unsubstituted phenyl, cycloalkyl or heterocyclyl;

each $R_2$ is independently selected from alkyl, alkoxy, amino, aminoalkyl, —$NO_2$, =O, —$NHC_2H_4OH$, —C(=NH)$NH_2$, —C(=O)$NH_2$, —C(=O)$NHCH_3$, —C(=O)OH, phenyl or heterocycloalkyl;

$X_4$ is an optionally substituted with one or more $R_3$ or unsubstituted phenyl, cycloalkyl or heterocylyl;

each $R_3$ is independently selected from alkyl, alkoxy, amino, halo, hydroxyl, alkylamino, dialkylamino, —$NO_2$, —CONR'R", —$CO_2$R', —NHCOR', phenyl or heterocycloalkyl;

each R' and R" is independently-H or alkyl;

A1 is $CH_2$ or NH; and

I is an integer of 0 or 1.

* * * * *